(12) United States Patent
Navarre et al.

(10) Patent No.: US 11,319,313 B2
(45) Date of Patent: May 3, 2022

(54) CRYSTALLINE FORMS OF DEUTERIUM-ENRICHED PIOGLITAZONE

(71) Applicant: Poxel SA, Lyons (FR)

(72) Inventors: Laure Françoise Valérie Navarre, Lyons (FR); Emeline Gardette, Lyons (FR); Sébastien Bolze, Massieux (FR); Sheila DeWitt, Auburn, NH (US); Vincent Jacques, Somerville, MA (US)

(73) Assignee: Poxel SA, Lyons (FR)

(*) Notice: Subject to any disclaimer, the term of this patent is extended or adjusted under 35 U.S.C. 154(b) by 0 days.

(21) Appl. No.: 17/314,538

(22) Filed: May 7, 2021

(65) Prior Publication Data

US 2021/0403464 A1 Dec. 30, 2021

Related U.S. Application Data

(60) Provisional application No. 63/046,304, filed on Jun. 30, 2020, provisional application No. 63/046,309, filed on Jun. 30, 2020.

(51) Int. Cl.
*C07D 417/12* (2006.01)
*A61K 9/14* (2006.01)
*C07B 59/00* (2006.01)

(52) U.S. Cl.
CPC .......... *C07D 417/12* (2013.01); *A61K 9/14* (2013.01); *C07B 59/002* (2013.01); *C07B 2200/05* (2013.01); *C07B 2200/13* (2013.01)

(58) Field of Classification Search
CPC .......... C07D 417/12; A61K 9/14; C07B 59/00
See application file for complete search history.

(56) References Cited

U.S. PATENT DOCUMENTS

| | | | |
|---|---|---|---|
| 4,421,865 A | 12/1983 | Shen | |
| 4,687,777 A | 8/1987 | Meguro et al. | |
| 5,134,127 A | 7/1992 | Stella et al. | |
| 5,149,820 A | 9/1992 | Borretzen et al. | |
| 5,441,971 A | 8/1995 | Sohda et al. | |
| 6,191,154 B1 | 2/2001 | Landreth et al. | |
| 6,221,335 B1 | 4/2001 | Foster | |
| 6,334,997 B1 | 1/2002 | Foster et al. | |
| 6,432,993 B1 | 8/2002 | Fujita et al. | |
| 6,440,710 B1 | 8/2002 | Keinan et al. | |
| 6,603,008 B1 | 8/2003 | Ando et al. | |
| 6,706,746 B2 | 3/2004 | Fujita et al. | |
| 7,135,485 B2* | 11/2006 | Wizel | C07D 417/12 514/342 |
| 7,517,990 B2 | 4/2009 | Ito et al. | |
| 8,067,450 B2 | 11/2011 | Colca et al. | |
| 8,236,786 B2 | 8/2012 | Finch et al. | |
| 8,263,631 B2 | 9/2012 | Fujiwara et al. | |
| 8,389,556 B2 | 3/2013 | Colca et al. | |
| 8,722,710 B2 | 5/2014 | Czarnik | |
| 8,969,581 B2 | 3/2015 | DeWitt | |
| 9,123,444 B2 | 9/2015 | Subramaniam et al. | |
| 9,416,117 B2 | 8/2016 | DeWitt | |
| 9,782,395 B2 | 10/2017 | Garcia Collazo et al. | |
| 9,833,445 B2 | 12/2017 | DeWitt | |
| 9,925,175 B2 | 3/2018 | Czarnik | |
| 10,188,639 B2 | 1/2019 | DeWitt et al. | |
| 2003/0181494 A1 | 9/2003 | Neogi et al. | |
| 2004/0253180 A1 | 12/2004 | Foster et al. | |
| 2007/0082929 A1 | 4/2007 | Gant et al. | |
| 2007/0197695 A1 | 8/2007 | Potyen et al. | |
| 2009/0028868 A1 | 1/2009 | Fujiwara et al. | |
| 2009/0076093 A1 | 3/2009 | Czarnik | |
| 2009/0082405 A1* | 3/2009 | Czarnik | A61K 31/4439 514/342 |
| 2012/0015982 A1 | 1/2012 | Colca et al. | |
| 2014/0221369 A1 | 8/2014 | DeWitt | |
| 2014/0243377 A1 | 8/2014 | Czarnik | |
| 2014/0275180 A1 | 9/2014 | DeWitt | |
| 2015/0284346 A1 | 10/2015 | DeWitt | |
| 2016/0331737 A1 | 11/2016 | DeWitt et al. | |
| 2016/0354355 A1 | 12/2016 | Czarnik | |
| 2017/0049762 A1 | 2/2017 | DeWitt | |
| 2018/0117026 A1 | 5/2018 | DeWitt et al. | |
| 2018/0118730 A1 | 5/2018 | DeWitt et al. | |
| 2018/0125827 A1 | 5/2018 | DeWitt et al. | |
| 2018/0125834 A1 | 5/2018 | DeWitt et al. | |
| 2018/0133204 A1 | 5/2018 | DeWitt | |
| 2019/0269665 A1 | 9/2019 | DeWitt et al. | |

(Continued)

FOREIGN PATENT DOCUMENTS

| EP | 1628646 B1 | 7/2010 |
|---|---|---|
| WO | 92/018501 A1 | 10/1992 |
| WO | 1995/26325 A2 | 10/1995 |

(Continued)

OTHER PUBLICATIONS

S. V. Patil et al., Improved compressibility, flowability, dissolution and bioavailability of pioglitazone hydrochloride by emulsion solvent diffusion with additives, Pharmazie, 67, 215-223. (Year: 2012).*
Kahn, et al., "Unraveling the mechanism of action of thiazolidinediones," J. Clin. Invest. 2000, 106, 1305-1307.
Norris, et al., "Muscle-specific PPAR?-deficient mice develop increased adiposity and insulin resistance but respond to thiazolidinediones," J. Clin Invest 2003, 112, 608-618.
Lehmann, et al., "An Antidiabetic Thiazolidinedione is a High Affinity Ligand for Peroxisome Proliferator-activated Receptor ? (PPAR?)*," J Biol Chem 1995, 270, 12953-12956, Nat Med 2013, 19, 557-566.

(Continued)

*Primary Examiner* — Michael G. Hartley
*Assistant Examiner* — Jagadishwar R Samala
(74) *Attorney, Agent, or Firm* — Goodwin Procter LLP

(57) ABSTRACT

Provided herein are crystalline forms of deuterium-enriched (R)-pioglitazone and compositions thereof. Also provided herein are methods of using the crystalline forms of deuterium-enriched (R)-pioglitazone and compositions thereof.

14 Claims, 23 Drawing Sheets

(56) References Cited

U.S. PATENT DOCUMENTS

2020/0179360 A1 6/2020 Czarnik

FOREIGN PATENT DOCUMENTS

| WO | 1999/018081 A1 | 4/1999 |
|---|---|---|
| WO | 2003/033494 A1 | 4/2003 |
| WO | WO-2003026586 A2 | 4/2003 |
| WO | 2003/059271 A2 | 7/2003 |
| WO | WO-2003026586 A3 | 10/2003 |
| WO | 2004/073622 A2 | 9/2004 |
| WO | 2005/058827 A1 | 6/2005 |
| WO | 2006/064826 A1 | 6/2006 |
| WO | 2006/083781 A1 | 8/2006 |
| WO | 2006/126673 A1 | 11/2006 |
| WO | 2007/007656 A1 | 1/2007 |
| WO | 2007/100027 A1 | 9/2007 |
| WO | 2007/109024 A2 | 9/2007 |
| WO | 2007/136129 A1 | 11/2007 |
| WO | 2008/099944 A1 | 8/2008 |
| WO | 2009/038681 A1 | 3/2009 |
| WO | 2010/015818 A1 | 2/2010 |
| WO | 2010/150014 A1 | 12/2010 |
| WO | 2011/017244 A1 | 2/2011 |
| WO | 2011/065420 A1 | 6/2011 |
| WO | 2011/098799 A2 | 8/2011 |
| WO | 2011/098801 A1 | 8/2011 |
| WO | 2011/100685 A2 | 8/2011 |
| WO | 2011/133441 A2 | 10/2011 |
| WO | 2013/011402 A1 | 1/2013 |
| WO | 2013/056232 A2 | 4/2013 |
| WO | 2013/134626 A1 | 9/2013 |
| WO | 2014/121036 A1 | 8/2014 |
| WO | 2014/152843 A1 | 9/2014 |
| WO | 2015/109037 A1 | 7/2015 |
| WO | 2016153948 A1 | 9/2016 |

OTHER PUBLICATIONS

Wang, et al., "Peroxisome Prolifterator-Activated Receptor ? and Its Role in Adipocyte Homeostatis and Thiazolidinedione-Mediated Insulin Sensitation," Mol Cell Biol 2018, 38, e00677-17.

Ahmadian, et al., "PPAR? signaling and metabolism: the good, the bad and the future," Nat Med 2013, 19, 557-66.

Zhang et al., A Newly Discovered Racemic Compound of Pioglitazone Hydrochloride Is More Stable than the Commercial Conglomerate, Jan. 21, 2019, pp. 414-417.

Czarnik, et al., "Characterizing the non-PPAR? Mitochondrial Function Modulation & Anti-inflammatory Activity of Thiazolidinedione (TZD) Enantiomers using Deuterium," Discovery of DRX-065, Aug. 24, 2016, pp. 1-30.

Klussmann, et al., "Rationalization and Prediction of Solution Enantiomeric Excess in Ternary Phase Systems," Angew. Chem. Int. Ed. 2006, 45, pp. 7985-7989.

Coquerel, "Solubility of chiral species as function of the enantiomeric excess," 2015 Royal Pharmaceutical Society, Journal of Pharmacy and Pharmacology, 67, pp. 869-878.

Srisanga, et al., "Racemic Compound, Conglomerate, or Solid Solution: Phase Diagram Screening of Chiral Compounds," 2010 American Chemical Society, pp. 1808-1812.

PCT/US2010/150014 International Search Report dated Aug. 24, 2010.

PCT/US2010/015818 International Search Report dated Oct. 11, 2009.

Jacques, et al., "Safety, Tolerability and Pharmacokinetics of DRX-065, the Stabilized, Preferred R-Stereoisomer of Pioglitazone: A Mitochondrial Function Modulator for Nonalcoholic Steatohepatitis (NASH) without the PPAR? Agonism and Related Side Effects of Pioglitazone," Abstract Poster, Hepatology 2018, vol. 68 Issue S1 (Oct. 1, 2018), 964A.

Bolze, et al, "Phase 1 Study of PXL065 Confirms Dose-Proportionality & Stabilization of the Preferred Stereoisomer (R-Pioglitazone) for the Treatment of NASH," Hepatology 2019, Abstract Poster, vol. 70 Issue S1 (Oct. 1, 2019), 1264A-1265A.

Bolze, et al., "Phase 1b Study of PXL065 (Deuterium-Stabilized R-Pioglitazone), a Novel NASH Candidate, Predicts 15mg Equivalent to 45mg Actos®," Abstract Poster, Hepatology 2020, vol. 72 Issue S1 (Oct. 1, 2020), 1055A-1056A.

Bharatam et al., "Rapid Racemization in Thiazolidinediones: A Quantum Chemical Study", J. Phys. Chem. A., 108:3784-3788 (2004).

Buteau, K., "Deuterated Drugs: Unexpectedly Nonobvious?", 10 J. High Tech. L. 22 (2009) (53 pages).

Cabrero et al., "Peroxisome Proliferator-Activated Receptors and the Control of Inflammation", Current Drug Target-Inflammation & Allergy, 1(3):243-248 (2002) (Abstract).

Chen et al., "Insulin Resistance and Metabolic Derangements in Obese Mice are Ameliorated by a Novel Peroxisome Proliferator-activated Receptor g-sparing Thiazolidinedione", J. Biol. Chem., 287(28):23537-23548 (2012).

Colca et al., "Identification of a Mitochondrial Target of Thiazolidinedione Insulin Sensitizers (mTOT)—Relationship to Newly Identified Mitochondrial Pyruvate Carrier Proteins", PLOS One, 8(5)e61551:1-10 (2013).

Colca et al., "Identification of a Novel Mitochondrial Protein ("mitoNEET") Cross-linked Specifically by a Thiazolidinedione Photoprobe," Am. J. Physiol. Endocrinol. Metab. (2004) vol. 286, No. 2, pp. E252-E260.

Divakaruni et al., " Thiazolidinediones are Acute, Specific Inhibitors of the Mitochondrial Pyruvate Carrier," Proc Natl Acad Sci USA, (2013), 110(14):5422-7.

Federal Register "Examination guidelines" p. 1-34, Sep. 1, 2010.

Fisher et al., "The complexities inherent in attempts to decrease drug clearance by blocking sites of CYP-mediated metabolism", Curr. Opin. Drug Disc. Dev., 9(1):101-109 (2006).

Foster, A., "Deuterium Isotope Effects in the Metabolism of Drugs and Xenobiotics: Implications for Drug Design", Adv. Drug Res., 14:2-40(1985).

Foster, "Deuterium Isotope Effects in Studies of Drug Metabolism," Trends Pharmacol Sci, (1984), 5:524-7.

Harbeson et al., "Deuterium in Drug Discovery and Development", Annual Reports in Med Chem, 46:403-417 (2011).

Hutt et al., "The Chiral Switch: The Development of Single Enantiomer Drugs from Racemates", ACTA Facult. Pharm. Univ. Comenianae, 50:7-23 (2003).

PCT/US2014/014083 International Search Report and Written Opinion dated May 16, 2014 (12 pages).

PCT/US2014/027943 International Search Report and Written Opinion dated Jul. 10, 2014 (15 pages).

Jaakkola et al., "Pioglitazone is Metabolized by CYP2C8 and CYP3A4 in vitro. Potential for Interactions with CYP2C8 Inhibitors," Basic Clin Phamacol Toxicol, (2006), 99(1):44-51.

Jaakkola et al., "Montelukast and Zafirlukast do not Affect the Pharmacokinetics of the CYP2C8 Substrate Pioglitazone," Eur J Clin Pharmacol, (2006), 62(7):503-9.

Jamali et al., "Investigation of racemisation of the enantiomers of glitazone drug compounds at different pH using chiral HPLC and chiral CE", J. Pharm and Biomed Anal., 46:82-87 (2008).

Kaufman et al., "Deuterium Enrichment of Vitamin A at the C20 Position Slows the Formation of Detrimental Vitamin A Dimers in Wild-type Rodents", J Biol. Chem., 286(10):7958-7965 (2011).

Kushner, D.J. et al. "Pharmacological Uses and Perspectives of Heavy Water and Deuterated Compounds," Canadian Journal of Physiology and Pharmacology, 1999, 77(2), 79-88.

Maltais et al., "In Vitro and In Vivo Isotope Effects with Hepatitis C Protease Inhibitors: Enhanced Plasma Exposure of Deuterated Teleprevir versus Teleprevir in Rats", J. Med. Chem. (2009) vol. 52, pp. 7993-8001.

Mislow et al., "A Note on Steric Isotope Effects. Conformational Kinetic Isotope Effects in the Racemization of 9,10-Dihydro-4,5-Dimethylphenanthrene", J. Am. Chem. Soc. 85:1199-1200 (1963).

Motani et al., "INT131: A Selective Modulator of PPARg", J. Mol. Biol., 386:1301-1311 (2009).

(56) References Cited

OTHER PUBLICATIONS

Nassar et al., "Improving the decision-making process in the structural modification of drug candidates: enhancing metabolic stability", Drug Discovery Today, 9(23):1020-1028 (2004).
Nelson et al., "The Use of Deuterium Isotope Effects to Probe the Active Site Properties, Mechanism of Cytochrome P450-Catalyzed Reactions, and Mechanisms of Metabolically Dependent Toxicity", Drug Metabolism and Disposition, 31(12):1481-1498 (2003).
Parks et al., "Differential Activity of Rosiglitazone Enantiomers at PPARg", Bioorg. & Medicinal Chem. Letters, 8:3657-3658 (1998).
Pfutzner et al., "Pioglitazone: update on an oral antidiabetic drug with antiatherosclerotic effects", Expert Opin. Pharmacother., 8(12):1985-1998 (2007).
Shao et al., "Derivatives of tramadol for increased duration of effect", Bioorg. Med. Chem. Lett. 16:691-694 (2006).
Shao, L. & Hewitt, M.C. "The Kinetic Isotope Effect in the Search for Deuterated Drugs," Drug News & Perspectives, 2010, vol. 23, No. 6, pp. 398-404.
Sohda et al., "Studies on Antidiabetic Agents. XII.1) Synthesis and Activity of the metabolites of (±)-5-[p-[2-(5-Ethyl-2-pyridyl)ethoxy]benzyl]2,4-thiazolidinedione (Pioglitazone)", Chem. Pharm. Bull., 43(12):2168-2172 (1995).
Stedman and Barclay, "Review Article: Comparison of the Pharmacokinetics, Acid Suppression and Efficacy of Proton Pump Inhibitors," Aliment Pharmacol Ther, (2000), 14(8):963-78.
Wade, D., "Deuterium isotope effects on noncovalent interactions between molecules", Chemico-Biological Interactions, 117 p. 191-217 (1999).
Wiberg, K., "The Deuterium Isotope Effect", Chem. Rev., 55(4):713-743 (1955).
Yamamoto et al., "Synthesis and Configurational Stability of (S)- and (R)-Deuteriothalidomides", Chem. Pharm. Bull. 58(1):1110-112 (2010).
Yarnell, A., "Heavy-Hydrogen Drugs Turn Heads, Again", Chemical & Engineering News, 87(25):136-39 (2009).
Zhu Y. et al., "Deuterated Clopidogrel Analogues as a New Generation of Antiplatelet Agents", ACS Med. Chem. Lett. 2013, vol. 4, Issue 3, pp. 349-352.
Baillie, T., "The Use of Stable Isotopes in Pharmacological Research", Pharmacological Reviews, 33(2):81-132 (1981).
Browne, T., "Stable Isotope Techniques in Early Drug Development: An Economic Evaluation", J Clin Pharmacol, 38:213-220 (1998).
Cherrah et al., "Study of Deuterium Isotope Effects on Protein Binding by Gas Chromatography/Mass Spectrometry. Caffeine and Deuterated Isotopomers", Biomedical and Environmental Mass Spectrometry, 14:653-657 (1987).
Dyck et al., "Effects of Deuterium Substitution on the Catabolism of ß-Phenylethylamine: An In Vivo Study", J Neurochem, 46(2):399-404 (1986).
Gouyette, A., "Synthesis of Deuterium-labelled Elliptinium and its Use in Metabolic Studies", Biomedical and Environmental Mass Spectrometry, 15:243-247 (1988).
Haskins, N. J. "The Application of Stable Isotopes in Biomedical Research," Biomedical Mass Spectrometry, 9 (7), 1982, 269-277.
Honma et al., "The Metabolism of Roxatidine Acetate Hydrochloride", Drug Metabolism and Disposition, 15(4):551-559 (1987).
Pieniaszek, Jr., et al., "Moricizine Bioavailability via Simultaneous, Dual, Stable Isotope Administration: Bioequivalence Implications", J Clin Pharmacol, 39:817-825 (1999).
Tonn et al. "Simultaneous Analysis of Diphenhydramine and a Stable Isotope Analog (2H10)Diphenhydramine Using Capillary Gas Chromatography with Mass Selective Detection in Biological Fluids from Chronically Instrumented Pregnant Ewes," Biological Mass Spectrometry, 22 (11) 1993, 633-642.
Wolen, R. L. "The application of stable isotopes to studies of drug bioavailability and bioequivalence," J. Clin. Pharm. (1986) vol. 26, pp. 419-424.

Aithal et al., "Randomized, Placebo-Controlled Trial of Pioglitazone in Nondiabetic Subjects with Nonalcoholic Steatohepatitis," Gastroenterology (2008), vol. 135, pp. 1176-1184.
Boettcher et al., "Meta-analysis: Pioglitazone Improves Liver Histology and Fibrosis in Patients with Non-Alcoholic Steatohepatitis," Aliment Pharmacol Ther, vol. 35, pp. 66-75 (2012).
Federico, et al., "Focus on emerging drugs for the treatment of patients with non-alcoholic fatty liver disease," World Journal of Gastroenterology (2014), vol. 20, pp. 16841-16857.
Kawaguchi et al., "Pioglitazone prevents hepatic steatosis, fibrosis, and enzyme-altered lesions in rat liver cirrhosis induced by a choline-deficient L-amino acid-defined diet," Biochemical and Biophysical Research Communications, (2004), vol. 315, pp. 187-195.
Kawai et al., "Hydrogen-Rich Water Prevents Progression of Non-alcoholic Steatohepatitis and Accompanying Hepatocarcinogenesis in Mice," Hepatology (2012), vol. 56, pp. 912-921.
Leclercq et al., "Intrahepatic insulin resistance in a murine model of steatohepatitis: effect of PPARg agonist pioglitazone," Laboratory Investigation (2007), vol. 87, pp. 56-65.
Lin et al., "Dose effect of thiazolidinedione on cancer risk in type 2 diabetes mellitus patients: a six-year population-based cohort study," Journal of Clinical Pharmacy and Therapeutics (2014), vol. 39, pp. 354-360.
Lutchman et al., "The Effects of Discontinuing Pioglitazone in Patients with Nonalcoholic Steatohepatitis," Hepatology (2007) vol. 46, pp. 424-429.
Sanyal et al., "Pioglitazone, Vitamin E, or Placebo for Nonalcoholic Steatohepatitis," The New England Journal of Medicine, (2010) vol. 362, pp. 1675-1685.
Sanyal et al., "A Pilot Study of Vitamin E Versus Vitamin E and Pioglitazone for the Treatment of Nonalcoholic Steatohepatitis," Clinical Gastroenterology and Hepatology (2004), vol. 2, pp. 1107-1115.
Uto et al., "The peroxisome proliferator-activated receptor-g agonist, pioglitazone, inhibits fat accumulation and fibrosis in the livers of rats fed a choline-deficient, L-amino acid-defined diet," Hepatology Research (2005), vol. 32, pp. 235-242.
Van Wagner et al., "The role of insulin-sensitizing agents in the treatment of nonalcoholic steatohepatitis," Ther Adv Gastroenterol (2011) vol. 4, pp. 249-263.
Zhang et al., "Thiazolidinediones Improve Hepatic Fibrosis in Rats with Non-Alcoholic Steatohepatitis by Activating the Adenosine Monophosphate-Activated Protein Kinase Signalling Pathway," Clinical and Experimental Pharmacology and Physiology, vol. 39, pp. 1026-1033 (2012).
Tilg and Moschen, "Evolving Therapies for Non-Alcoholic Steatohepatitis," Expert Opin Drug Discov, (2014), (6):687-96.
Lomonaco et al., "Nonalcoholic Fatty Liver Disease: Current Issues and Novel Treatment Approaches," Drugs, vol. 73, pp. 1-14 (2013).
Smith et al., "Non-Alcoholic Fatty Liver Disease," Critical Reviews in Clinical Laboratory Sciences, vol. 48, pp. 97-113 (2011).
Dorwald, "Side Reactions in Organic Synthesis," Wiley, pp. IX of preface pp. 1-15 (2005).
Woo, H.Y, et al., "Rescue therapy with adefovir in decompensated liver cirrhosis patients with lamivudine-resistant hepatitis B virus", Clinical and Molecular Hepatology, 2014, vol. 20, pp. 168-176.
Peng, S., et al., "An Updated Meta-Analysis of Randomized Controlled Trials Assessing the Effect of Sorafenib in Advanced Hepatocellular Carcinoma", PLOS One, 2014, vol. 9, No. 12, pp. e112530.
Farlow, M. R., et al., "Comparing Clinical Profiles in Alzheimer's Disease and Parkinson's Disease Dementia", Dementia and Geriatric Cognitive Disorders Extra, 2013, vol. 3, pp. 281-290.
Griebeler, M.L., et al., "Pharmacologic interventions for painful diabetic neuropathy: An umbrella systematic review and comparative effectiveness network meta-analysis", Annals of Internal Medicine, 2014, vol. 161, No. 9, pp. 639-649.
Zhou, C. et al., "Discovery of 5-aryloxy-2,4-thiazolidinediones as potent GPR40 agonists", Bioorg. Med. Chem. Lett. 2010, vol. 20, No. 3, pp. 1298-1301.
Christiansen, E. et al., "Identification of a Potent and Selective Free Fatty Acid Receptor 1 (FFA1/GPR40) Agonist with Favorable Physicochemical and in Vitro ADME Properties", J. Med Chem. (2011) vol. 54, No. 19, pp. 6691-6703.

(56) References Cited

OTHER PUBLICATIONS

PCT/US2015/011493 International Search Report and Written Opinion dated Mar. 6, 2015 (9 pages).
Hardy, T. et al. "Nonalcoholic fatty liver disease: new treatments," Curr. Opin. Gastroenterology (2015) vol. 31, No. 3, pp. 175-183.
Chalasani et al., "The Diagnosis and Management of Non-Alcoholic Fatty Liver Disease: Practice Guideline by the American Gastroenterological Association, American Association for the Study of Liver Diseases, and American College of Gastroenterology," Gastroenterology (2012), vol. 142, No. 7, pp. 1592-1609.
Cusi, K. et al. "Long-Term Pioglitazone Treatment for Patients With Nonalcoholic Steatohepatitis and Prediabetes or Type 2 Diabetes Mellitus: A Randomized, Controlled Trial," Ann. Intern. Med. published online at doi: 10.7326/M15-1774. Published in final form as Ann. Intern. Med. (2016) vol. 165, No. 5, p. 305-315.
Tanis, S. P. et al. "Synthesis and Biological Activity of Metabolites of the Antidiabetic, Antihyperglycemic Agent Pioglitazone," J Med. Chem. (1996) vol. 39, pp. 5053-5063.
Leoni, A. et al., "Novel thiazole derivatives: a patent review (2008-2012. Part 2)," Expert Opin. Ther. Patents (2014), vol. 24, No. 7, pp. 759-777.
Jorden, D., "World Alzheimer Day: French Doctor Denounces Routine Alzheimer Medications," dated Dec. 20, 2015. Downloaded from the Internet at URL: https://zcomm.org/znetarticle/world-alzheimer-day-french-doctor-denounces-routine-alzheimer-medications/ (4 pages).
Landreth, G. et al., "PPARg Agonists as Therapeutics for the Treament of Alzheimer's Disease," Neurotherapeutics: J. Am. Soc. Exper. NeuroTherapeutics (2008), vol. 5, No. 3, pp. 481-489.
Polyzos, S. A. and Mantzoros, C. S. "Adiponectin as a target for the treament of nonalcoholic steatohepatitis with thiazolidinediones: A systematic review," Metabolism, Clinical and Experimental (2016), vol. 65, No. 9, pp. 1297-1306.
World Health Organization "The ICD-10 Classification of Mental and Behavioural Disorders: Diagnostic criteria for research," Geneva (1993).
Venkatesh, S. and Lipper, R. A., "Role of the Development Scientist in Compound Lead Selection and Optimization," J Pharm. Sci. (2000), vol. 89, No. 2, pp. 145-154.
Mandard, S. and Patsouris, D., "Nuclear Control of the Inflammatory Response in Mammals by Peroxisome Proliferator-Activated Receptors," PPAR Research (2013) Article ID 613864, DOI: 10.1155/2013/613864. (23 pages).
Binda, C. et al., "Molecular Insights into Human Monoamine Oxidase B Inhibition by the Glitazone Antidiabetes Drugs," ACS Med Chem. Lett. (2012), vol. 3, pp. 39-42.
Chalasani et al., "The Diagnosis and Management of Non-Alcoholic Fatly Liver Disease: Practice Guideline by the American Association for the Study of Liver Diseases, American College of Gastroenterology, and the American Gastroenterological Association," Hepatology (2012), vol. 55, No. 6, pp. 2005-2023.
Promrat et al., "A Pilot Study of Pioglitazone Treatment for Nonalcoholic Steatohepatitis," Hepatology (2004), vol. 39, pp. 188-196.
Shadid et al. "Effect of pioglitazone on biochemical indices of non-alcoholic fatty liver disease in upper body obesity," Clinical Gastroenterology and Hepatology, 2003, 1:384-387.
EP 19203107, Supplementary European Search Report, dated Sep. 29, 2020.
Binda, et al., "Molecular insights into human monoamine oxidase B inhibition by the glitazone antidiabetes drugs." ACS medicinal chemistry letters 3, No. 1 (2012): pp. 39-42.
Mehtää, et al., "Pioglitazone use and risk of bladder cancer: a systematic literature review and meta-analysis of observational studies." Diabetology international 10, No. 1 (2019): pp. 24-36.
Tachibana, et al., "The role of PPARs in cancer." pp. 1-15, PPAR research 2008 (2008).
Tafuri et al., "Effect of Pioglitazone on the Course of New-Onset Type 1 Diabetes Mellitus", Journal of Clinical Research in Pediatric Endocrinology, vol. 5, No. 4, Jan. 1, 2013 (Jan. 1, 2013), pp. 236-239, XP55730567, ISSN: 1308-5727, DOI: 10.4274/Jcrpe.981.

Zardi et al., "Hepatic PPARs: Their Role in Liver Physiology, Fibrosis and Treatment", Current Medicinal Chemistry, 2013, 20,, Jan. 1, 2013 (Jan. 1, 2013), pp. 3370-3396, XP55730602.
Shah et al., "Metformin and Pioglitazone in Polycystic Ovarian Syndrome: A Comparative Study", The Journal of Obstetrics and Gynecology of India, vol. 62, No. 5, Oct. 1, 2012 (Oct. 1, 2012), pp. 551-556, XP055730931.
Paz-Filho et al., "Leptin therapy, insulin sensitivity, and glucose homeostasis", Indian J Endocrinol Metab. Dec. 2012; 16(Suppl 3): S549-S555., Jan. 1, 2012 (Jan. 1, 2012), pages S549-S555.
Li et al., "Twelve Weeks of Pioglitazone Therapy Significantly Attenuates Dysmetabolism and Reduces Inflammation in Continuous Ambulatory Peritoneal Dialysis Patients—a Randomized Crossover Trial", Perit Dial Int. Sep.-Oct. 2012; 32(5): 507-515, Jan. 1, 2012 (Jan. 1, 2012), pp. 507-515.
Anonymous: "Thiazolidinedione—Wikipedia", Jan. 1, 2013 (Jan. 1, 2013), XP055730935.
LeBrasseur, et al.," I hiazolidinediones can rapidly activate AMP-activation protein kinase in mammalian tissues," Am. J. Physiol. Endocrinol. Metab. 2006, 291, E175-81.
Feinstein, et al., "Receptor-independent actions of PPAR thiazolidinedione agonists: Is mitochondrial function the key?" Biochem. Pharmacol 2005, 70, 177-188.
Bender, et al., "The mitochondrial pyruvate carrier in health and disease: To carry or not to carry?" Biochim. Biophys. Acta—Mol Cell Res, 2016, 1863, 2436-2442.
Brunmair, et al., "Thiazolidinediones, Like Metformin, Inhibit Respiratory Complex I," Diabetes 2004, 53, 1052-1059.
Jacques, et al., "Deuterium-Stabilized (R)-Pioglitazone (PXL065) Is Responsible for Pioglitazone Efficacy in NASH yet Exhibits Little to No PPAR? Activity," Hepatol. Commun. Apr. 10, 2021 doi.org/10.1002/hep4.1723.
U.S. Appl. No. 12/233,751, filed Sep. 19, 2008, Czarnik, Anthony W.
U.S. Appl. No. 16/531,812, filed Aug. 5, 2019, Czarnik, Anthony W.
U.S. Appl. No. 17/166,588, filed Feb. 3, 2021, Czarnik, Anthony W.
U.S. Appl. No. 14/272,761, filed May 8, 2014, Czarnik, Anthony W.
U.S. Appl. No. 15/088,472, filed Apr. 1, 2016, Czarnik, Anthony W.
U.S. Appl. No. 15/917,983, filed Mar. 12, 2018, Czarnik, Anthony W.
U.S. Appl. No. 15/109,533, filed Oct. 7, 2016, Dewitt, Sheila et al.
U.S. Appl. No. 16/211,488, filed Dec. 6, 2018, Dewitt, Sheila et al.
Pirali et al., "Applications of Deuterium in Medicinal Chemistry" Journal of Medicinal Chemistry, 62(11), pp. 5276-5297 (2019).
PCT/IB2021/000661 International Search Report and Written Opinion dated Nov. 23, 2021 (15 pages).
S. DeWitt et al., "DRX-065: A Novel Mitochondrial Modulator for NASH" DeuterX, AASLD Oral Presentation, Boston, MA, Nov. 2016, pp. 1-52.
S. DeWitt et al., "DRX-065: The Deuterated (R)-Enantiomer of Pioglitazone as a Nonalcoholic Steatohepatitis (NASH) drug candidate: Results from Diet-Induced Rodent NASH Models and Phase I" MEDI 317, ACS National Meeting, Boston, MA, Aug. 21, 2018, pp. 1-34.
V. Jacques et al., "Safety, Tolerability & PK of PXL065*, the Stabilized R-Stereoisomer of Pioglitazone: A Mitochondrial Function Modulator for NASH without PPARγ Agonism & Related Side Effects" Poster, AASLD, San Francisco, CA, Nov. 2018.
J. Singh., "Therapeutic efficacy potential of PXL770—a novel direct AMPK-activator and PXL065—deuterium-stabilized R pioglitazone-for X-linked adrenoleukodystrophy" virtual Oral Presentation, ALP Connect Nov. 13, 2020, pp. 1-22.
S. Bozec., "Mitochondrial Targeted Therapeutics" Presentation at virtual meeting, Mitochondria-Targeted Drug Development Summit, Apr. 29, 2021, pp. 1-25.
D. E. Moller., "Poxel Mid-to-Late-Stage Metabolic Pipeline" Nash Summit, Boston, MA, May 2020, pp. 1-32.
S. DeWitt., "DRX-065: A Novel Mitochondrial Modulator" Oral Presentation, NASH-TAG, Park City, UT, Jan. 2018, pp. 1-23.
V. Jacques et al., "DRX-065: A Novel Mitochondrial Modulator for NASH, Pharmacokinetic (PK) Results & Modeling from Phase I Study" Poster, NASH-TAG, Park City, UT, Jan. 2018.

(56) References Cited

OTHER PUBLICATIONS

S. DeWitt et al.,"PXL065, Pioglitazone (pio), and Thiazolidinediones (TZDs): Unraveling Pio's superior efficacy for NASH and role of stereoisomers" NASH-TAG, Park City, UT, Jan. 4, 2019, pp. 1-21.
S.C. Cheetham et al., "Efficacy of DRX-065, the stabilized R-enantiomer of pioglitazone (pio), in choline-deficient (CD) and methionine/choline-deficient (MCD) diet mouse models of nonalcoholic steatohepatitis (NASH)" Poster, AASLD, Boston, MA, Nov. 2016.

* cited by examiner

CRYSTALLINE FORMS OF DEUTERIUM-ENRICHED PIOGLITAZONE

RELATED APPLICATIONS

This application claims the benefit of and priority to U.S. Provisional Patent Application Ser. No. 63/046,304, filed Jun. 30, 2020, and U.S. Provisional Patent Application Ser. No. 63/046,309, filed Jun. 30, 2020, the contents of each of which are hereby incorporated by reference in their entirety.

BACKGROUND

Thiazolidinediones (TZDs) are antidiabetic drugs that sensitize the body to insulin. These compounds were empirically discovered to be agonists of peroxisome proliferator-activated-receptors (PPARs), including PPAR-γ (PPARγ), a ligand-activated nuclear receptor that drives broad transcriptional programs associated with adipogenesis, lipid metabolism, innate immune function, and metabolic homeostasis (see, e.g., J. Clin. Invest. 2000, 106, 1305-1307, Trends Endocrinol. Metab. 2012, 23, 205-215). As such, the antidiabetic mechanism of action of TZDs has up to now been attributed to binding to, and activation of, PPARγ (see, e.g., J Biol Chem 1995, 270, 12953-12956, Nat Med 2013, 19, 557-566).

Therapeutics that modulate PPARs have been commercialized for treating medical disorders, such as metabolic disorders. One such example is the TZD, pioglitazone hydrochloride, which has been approved by the United States Food and Drug Administration as an adjunct to diet and exercise to improve glycemic control in adults with type 2 diabetes mellitus in multiple clinical settings. Pioglitazone hydrochloride is marketed under the registered trademark ACTOS® and the prescribing information for ACTOS® explains that pioglitazone is an agonist of PPARγ. PPARγ-related adverse side effects of ACTOS® have been reported including, for example, weight gain, edema and increased incidence of bone fracture.

However, emerging genetic and pharmacologic evidence suggests that TZDs exert many of their beneficial effects independently of PPARγ activation (see Biochem. Pharmacol. 2005, 70, 177-188). For instance, liver and skeletal muscle remain responsive to TZDs despite tissue-specific deletion of PPARγ (see J Clin Invest 2003, 112, 608-618, J Biol Chem 2012, 287, 23537-23548), and the whole-body insulin sensitizing effect of rosiglitazone persists upon PPARγ deletion in mature adipocytes (see Mol Cell Biol 2018, 38, e00677-17). Pharmacologic evidence also suggests TZDs have PPARγ-independent effects. They can acutely alter metabolic homeostasis on a timescale that is likely too rapid to be driven by broad gene expression changes (see Am. J. Physiol. Endocrinol. Metab. 2006, 291, E175-81), and several in vitro and in vivo experiments have shown that rank-order affinity for PPARγ does not always correlate with efficacy (see Biochem. Pharmacol. 2005, 70, 177-188). Pioglitazone and other TZDs have also been shown to have anti-inflammatory activity, which seems to be, at least in part, mediated by a mechanism not involving PPARs (Curr. Drug Targets Inflamm. Allergy 2002, 1, 243-248).

Recent work shows that most of the PPARγ-independent effects of TZDs could be attributed to inhibition of the mitochondrial pyruvate carrier (MPC), an inner mitochondrial membrane transporter responsible for the uptake of glucose-derived pyruvate from the cytoplasm into the mitochondrial matrix (see Biochim. Biophys. Acta-Mol Cell Res, 2016, 1863, 2436-2442). TZDs are acute, specific inhibitors of MPC activity at clinically relevant concentrations (see Proc. Natl. Acad. Sci. USA, 2013, 110, 5422-5427). TZDs also inhibit mitochondrial complex I (see Diabetes 2004, 53, 1052-1059), though at higher and perhaps supraphysiological concentrations relative to the effect on the MPC. Despite pioglitazone decades of use in humans with T2DM, the repertoire of targets for pioglitazone and its exact mechanism of action is only now beginning to be unraveled.

All TZDs, including pioglitazone, are a mixture of enantiomers and are characterized by the presence of a chiral center. This chiral center is prone to rapid, non-enzymatic inversion of configuration. Thus, the instability of the chiral center has prevented exploitation of the potential for differentiated pharmacology between the enantiomers of TZDs. For example, while the left-handed, or (S)-enantiomer, of rosiglitazone was identified as the most potent PPARγ agonist, (S)-rosiglitazone rapidly equilibrated to create a 1:1 mixture of (R)- and (S)-rosiglitazone, preventing further in vivo characterization of the enantiomers (see Bioorg. Med. Chem. Lett., 1998, 8, 3657-8). Furthermore, the anti-inflammatory effects of pioglitazone were shown to be uniquely associated with the (R)-enantiomer in a rat model of chronic obstructive pulmonary disease. This was achieved only after stabilization of the enantiomers in an acidic solution, followed by immediate intranasal dosing, which limited inversion during the time course of the study (see international patent application WO2010015818A1).

Due to the increasing number of patients suffering from disorders such as those mentioned above, and the limitations of existing therapies, such as adverse side effects, there is a need for new therapeutic agents for treating medical disorders in which modulation of PPARγ, anti-inflammatory, and/or MPC activity are predicted to be beneficial.

The use of deuterium-enriched enantiomers of pioglitazone to treat such medical disorders has gained significant interest, as it is believed that they may provide additional therapeutic efficacy and reduce the rate and severity of side effects compared to pioglitazone. Recently, the characterization of the unique pharmacological and pharmacokinetic properties of the deuterium-enriched (R) and/or (S)-enantiomers of pioglitazone has been reported (see Hepatol. Commun. 2021, April 10 doi.org/10.1002/hep4.1723). Preclinical studies demonstrated that (R)-pioglitazone retains the efficacy of pioglitazone in nonalcoholic steatohepatitis (NASH), including reduced hepatic triglycerides, free fatty acids, cholesterol, steatosis, inflammation, hepatocyte enlargement, and fibrosis. Although both enantiomers inhibit MPC, deuterium-enriched (R)-pioglitazone (PXL065) shows limited to no PPARγ activity, whereas (S)-pioglitazone appears responsible for the PPARγ activity and associated weight gain. Both enantiomers reduce plasma glucose and hepatic fibrosis to the same extent as pioglitazone in preclinical mouse models. In a phase 1a clinical study, the safety and tolerability of PXL065 (7.5, 22.5, 30 mg) was demonstrated as well as preferential exposure to the (R)-enantiomer in comparison to 45 mg Actos®. These results concluded that PXL065 at a dose lower than 22.5 mg is predicted to exhibit efficacy for NASH equal to, or greater than, 45 mg pioglitazone without the potentially detrimental weight gain and edema.

Developing solid forms of these deuterium-enriched pioglitazone enantiomers, however, that provide the physico-chemical properties necessary to manufacture a commercial drug product with the required efficacy remains a significant challenge. This is due to the unpredictability in the outcome of solid form screenings for any given compound and the subsequent unpredictability of the physicochemical properties of any solid forms discovered. Thus, there is a need for new solid forms of deuterium-enriched pioglitazone derivatives that achieve the required physicochemical properties necessary to provide superior efficacy over pioglitazone.

SUMMARY

In one aspect, the invention provides salt forms (e.g., crystalline salt forms) of deuterium-enriched (R)-pioglitazone (PXL065).

In various embodiments of the invention, a deuterium chloride salt of a deuterium-enriched compound of formula (I):

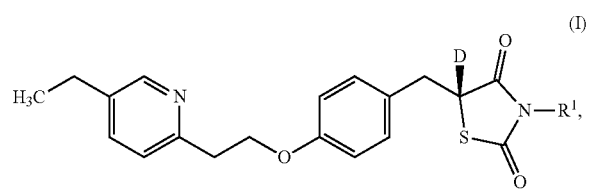

(I)

wherein $R^1$ is H or D, provided that the total deuterium abundance in the compound of formula (I) is about 1.3 to about 4.

In various embodiments of the invention, a crystalline deuterium chloride salt of a deuterium-enriched compound of formula (I)

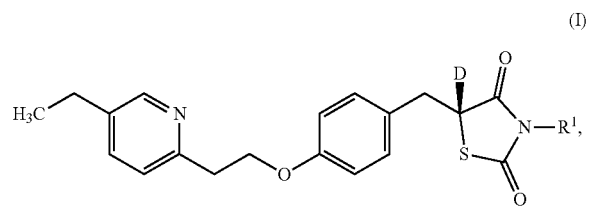

(I)

wherein $R^1$ is H or D, provided that the total deuterium abundance in the compound of formula (I) is about 1.3 to about 4, and wherein the crystalline deuterium chloride salt is characterized by an X-ray powder diffraction pattern comprising peaks at the following diffraction angles (2θ): 15.8°±0.2°, 22.8°±0.2°, and 26.0°±0.2°.

In various embodiments of the invention, a crystalline hydrochloride salt of a compound of formula (I-A):

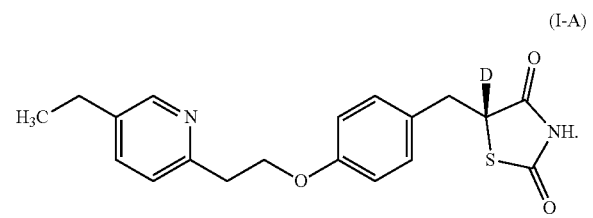 [SMILES: [2H][C@]1(Cc2ccc(OCCc3ccc(CC)cn3)cc2)SC(=O)NC1=O]

(I-A)

In various embodiments of the invention, a crystalline hydrochloride salt of the compound of formula (I-A)

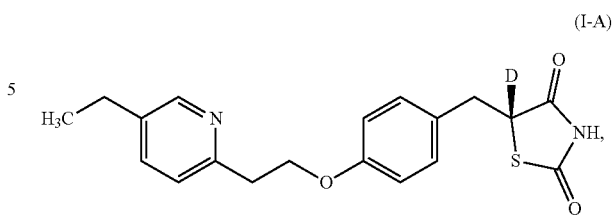

(I-A)

wherein the crystalline hydrochloride salt is characterized by an X-ray powder diffraction pattern comprising peaks at the following diffraction angles (2θ): 15.8°±0.2°, 22.8°±0.2°, and 26.0°±0.2°.

In another aspect, the invention provides pharmaceutical materials comprising particles of a crystalline salt (e.g., deuterium chloride salt, hydrochloride salt) of deuterium-enriched (R)-pioglitazone.

In various embodiments of the invention, the pharmaceutical material comprises particles of a crystalline deuterium chloride salt of a deuterium-enriched compound of formula (I)

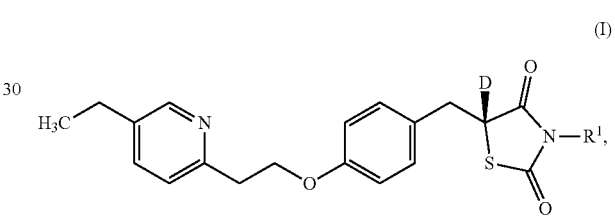

(I)

wherein $R^1$ is H or D, provided that the total deuterium abundance in the compound of formula (I) is about 1.3 to about 4, and wherein the particles in the composition have a crystal shape selected from hexagonal, rod, and combinations thereof.

In various embodiments of the invention, the pharmaceutical material comprises particles of a crystalline deuterium chloride salt of a deuterium-enriched compound of formula (I)

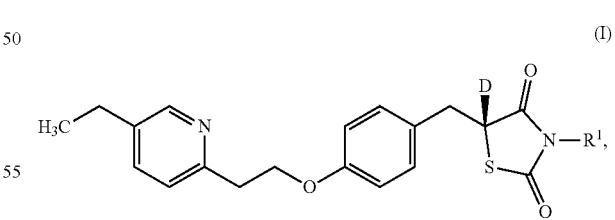

(I)

wherein $R^1$ is H or D, provided that the total deuterium abundance in the compound of formula (I) is about 1.3 to about 4, and wherein the particles have a particle size distribution which is defined by a d(0.9) of about 10 μm to about 800 μm preferably below 500 μm.

In various embodiments of the invention, the pharmaceutical material comprising particles of a crystalline hydrochloride salt of the compound of formula (I-A)

(I-A)

[Chemical structure of formula (I-A)]

wherein the particles in the composition have a needle-like crystal shape.

In various embodiments of the invention, the pharmaceutical material comprising particles of a crystalline hydrochloride salt of the compound of formula (I-A)

(I-A)

[Chemical structure of formula (I-A)]

wherein the particles have a particle size distribution which is defined by a d(0.9) of about 10 µm to about 800 µm preferably below 500 µm.

In another aspect, the invention provides pharmaceutical compositions comprising a crystalline salt of deuterium-enriched (R)-pioglitazone described herein, or a pharmaceutical material described herein, and a pharmaceutically acceptable excipient. In various embodiments, the pharmaceutical compositions comprise a crystalline deuterium chloride salt of deuterium-enriched (R)-pioglitazone and a pharmaceutically acceptable excipient. In various embodiments, the pharmaceutical compositions comprise a crystalline hydrochloride salt of deuterium-enriched (R)-pioglitazone and a pharmaceutically acceptable excipient.

In another aspect, the invention provides crystalline salt forms of deuterium-enriched (R)-pioglitazone, pharmaceutical materials, and pharmaceutical compositions useful for the treatment of the various conditions, diseases, and disorders described herein. In certain embodiments, the condition, disease, or disorder is a metabolic disorder. In certain embodiments, the condition, disease, or disorder is diabetes mellitus type 2 and/or nonalcoholic steatohepatitis. In certain embodiments, the condition, disease, or disorder is a neurological disorder. In some embodiments, the neurological disorder is adrenoleukodystrophy or adrenomyeloneuropathy.

DETAILED DESCRIPTION

Figure 1A:
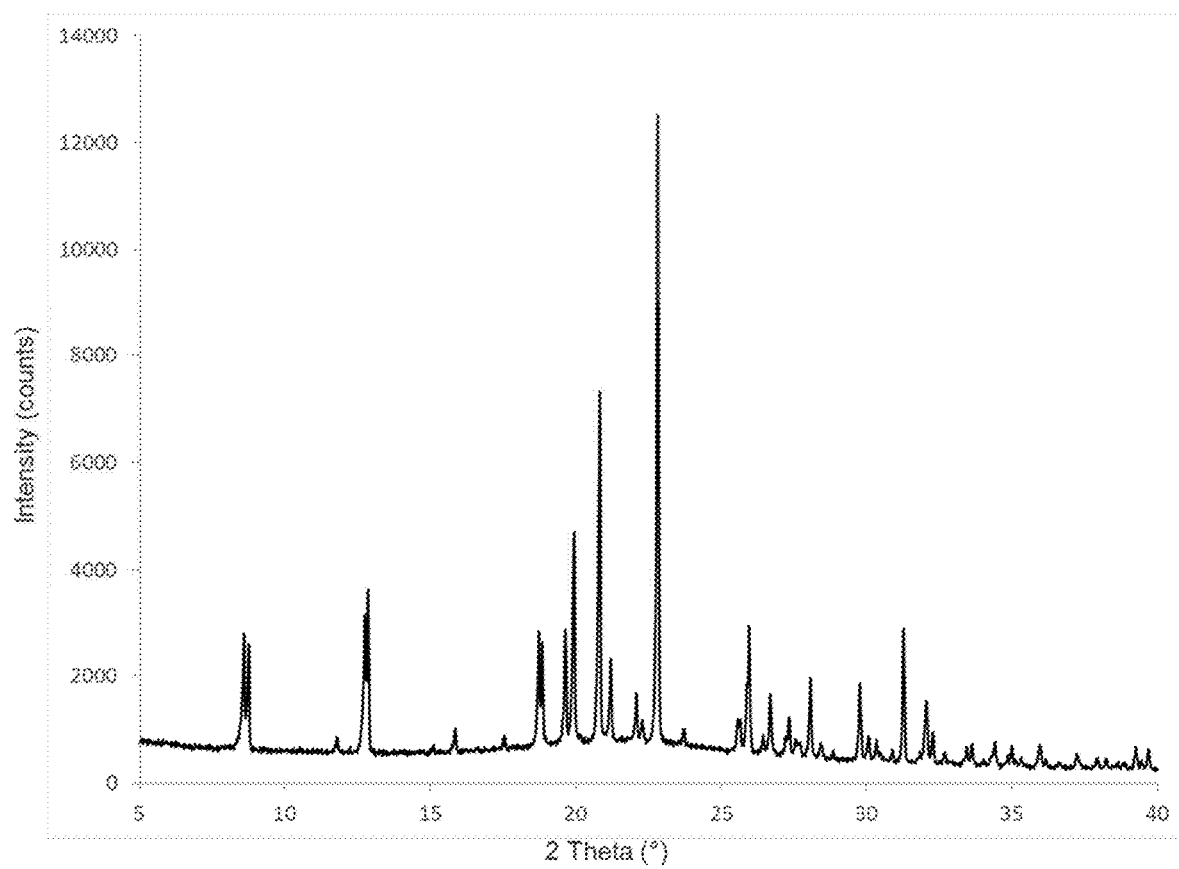
FIG. 1A is an exemplary X-ray powder diffraction (XRPD) pattern of the crystalline deuterium chloride salt of deuterium-enriched (R)-pioglitazone.

As generally described herein, the invention provides pharmaceutically acceptable salts of deuterium-enriched (R)-pioglitazone (e.g., crystalline salts of deuterium-enriched (R)-pioglitazone), also referred to herein as a compound of formula I, pharmaceutical compositions containing the same, and methods of using the salt forms of deuterium-enriched (R)-pioglitazone to treat medical conditions, diseases, and disorders (e.g., a neurological disorder, a cancer, a respiratory disorder, a metabolic disorder, a hepatitis, cardiovascular disease, an inflammatory disorder, an immune-mediated disorder, a dermatological disorder, or a skin defect) in a subject in need thereof. In particular, the invention provides crystalline hydrochloride and deuterium chloride salts of deuterium-enriched (R)-pioglitazone with unexpectedly improved solubilities at physiologically relevant pHs and in vivo bioavailability compared to the commercially available pioglitazone hydrochloride salt (Actos®).

Definitions

To facilitate an understanding of the present invention, a number of terms and phrases are defined below.

Unless defined otherwise, all technical and scientific terms used herein have the same meaning as commonly understood by one of ordinary skill in the art to which this invention belongs. The abbreviations used herein have their conventional meaning within the chemical and biological arts. The chemical structures and formulae set forth herein are constructed according to the standard rules of chemical valency known in the chemical arts.

Throughout the description, where compositions and kits are described as having, including, or comprising specific components, or where processes and methods are described as having, including, or comprising specific steps, it is contemplated that, additionally, there are compositions and kits of the present invention that consist essentially of, or consist of, the recited components, and that there are processes and methods according to the present invention that consist essentially of, or consist of, the recited processing steps.

In the application, where an element or component is said to be included in and/or selected from a list of recited elements or components, it should be understood that the element or component can be any one of the recited elements or components, or the element or component can be selected from a group consisting of two or more of the recited elements or components.

Further, it should be understood that elements and/or features of a composition or a method described herein can be combined in a variety of ways without departing from the spirit and scope of the present invention, whether explicit or implicit herein. For example, where reference is made to a particular compound, that compound can be used in various embodiments of compositions of the present invention and/or in methods of the present invention, unless otherwise understood from the context. In other words, within this application, embodiments have been described and depicted in a way that enables a clear and concise application to be written and drawn, but it is intended and will be appreciated that embodiments may be variously combined or separated without parting from the present teachings and invention(s). For example, it will be appreciated that all features described and depicted herein can be applicable to all aspects of the invention(s) described and depicted herein.

The articles "a" and "an" are used in this disclosure to refer to one or more than one (i.e., to at least one) of the grammatical object of the article, unless the context is inappropriate. By way of example, "an element" means one element or more than one element.

The term "and/or" is used in this disclosure to mean either "and" or "or" unless indicated otherwise.

It should be understood that the expression "at least one of" includes individually each of the recited objects after the expression and the various combinations of two or more of the recited objects unless otherwise understood from the context and use. The expression "and/or" in connection with three or more recited objects should be understood to have the same meaning unless otherwise understood from the context.

The use of the term "include," "includes," "including," "have," "has," "having," "contain," "contains," or "containing," including grammatical equivalents thereof, should be understood generally as open-ended and non-limiting, for example, not excluding additional unrecited elements or steps, unless otherwise specifically stated or understood from the context.

Where the use of the term "about" is before a quantitative value, the present invention also includes the specific quantitative value itself, unless specifically stated otherwise. As used herein, the term "about" refers to a ±10% variation from the nominal value unless otherwise indicated or inferred from the context.

At various places in the present specification, variable or parameters are disclosed in groups or in ranges. It is specifically intended that the description include each and every individual subcombination of the members of such groups and ranges. For example, an integer in the range of 0 to 40 is specifically intended to individually disclose 0, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, and 40, and an integer in the range of 1 to 20 is specifically intended to individually disclose 1, 2, 3, 4, 5, 6, 7, 8, 9, 10, 11, 12, 13, 14, 15, 16, 17, 18, 19, and 20.

The use of any and all examples, or exemplary language herein, for example, "such as" or "including," is intended merely to illustrate better the present invention and does not pose a limitation on the scope of the invention unless claimed. No language in the specification should be construed as indicating any non-claimed element as essential to the practice of the present invention.

Deuterium, which may also be referred to herein as $^2H$ and/or D, is a stable, non-radioactive isotope of $^1H$ hydrogen and has an atomic weight of 2.014. Hydrogen naturally occurs as a mixture of the isotopes $^1H$ hydrogen (i.e., protium), deuterium ($^2$H), and tritium ($^3$H). The natural abundance of deuterium is about 0.015%. One of ordinary skill in the art recognizes that in all chemical compounds with an H atom, the H atom actually represents a mixture of $^1$H hydrogen, deuterium ($^2$H), and tritium ($^3$H), where about 0.015% is deuterium. In various embodiments, compounds with a level of deuterium that has been enriched to be greater than its natural abundance of about 0.015% are considered unnatural and, as a result, novel over their non-enriched counterparts. In certain embodiments, compounds with a level of deuterium that has been enriched to be greater than its natural abundance of about 0.015% is a deuterium-enriched compound.

As used herein, "total deuterium content" or "total deuterium abundance" refer to number of deuteriums that are present in a molecule (if the molecule is a salt, the counter ion is also counted, e.g., the HCl or DCl salt of deuterium-enriched (R)-pioglitazone). The total deuterium content may be determined, for example, by a $^2$H-NMR. The deuterium content at the chiral center of a molecule (e.g., deuterium-enriched pioglitazone) may be determined, for an example, using $^1$H-NMR.

As a general matter, compositions specifying a percentage are by weight unless otherwise specified. Further, if a variable is not accompanied by a definition, then the previous definition of the variable controls.

As used herein, "pharmaceutical composition" or "pharmaceutical formulation" refers to the combination of an active agent with a carrier, inert or active, making the composition especially suitable for diagnostic or therapeutic use in vivo or ex vivo.

"Pharmaceutically acceptable" means approved or approvable by a regulatory agency of the federal or a state government or the corresponding agency in countries other than the United States, or that is listed in the U.S. Pharmacopoeia or other generally recognized pharmacopoeia for use in animals, and more particularly, in humans.

As used herein, "pharmaceutically acceptable excipient" refers to a substance that aids the administration of an active agent to and/or absorption by a subject and can be included in the compositions of the present invention without causing a significant adverse toxicological effect on the patient. Non-limiting examples of pharmaceutically acceptable excipients include water, NaCl, normal saline solutions, such as a phosphate buffered saline solution, emulsions (e.g., such as an oil/water or water/oil emulsions), lactated Ringer's, normal sucrose, normal glucose, binders, fillers, disintegrants, lubricants, coatings, sweeteners, flavors, salt solutions (such as Ringer's solution), alcohols, oils, gelatins, carbohydrates such as lactose, amylose or starch, fatty acid esters, hydroxymethycellulose, polyvinyl pyrrolidine, and colors, and the like. Such preparations can be sterilized and, if desired, mixed with auxiliary agents such as lubricants, preservatives, stabilizers, wetting agents, emulsifiers, salts for influencing osmotic pressure, buffers, coloring, and/or aromatic substances and the like that do not deleteriously react with the compounds of the invention. For examples of excipients, see Martin, Remington's Pharmaceutical Sciences, 15th Ed., Mack Publ. Co., Easton, Pa. (1975).

As used herein, "solid dosage form" means a pharmaceutical dose(s) in solid form, e.g., tablets, capsules, granules, powders, sachets, reconstitutable powders, dry powder inhalers and chewables.

As used herein, "administering" means oral administration, administration as a suppository, topical contact, intravenous administration, parenteral administration, intraperitoneal administration, intramuscular administration, intralesional administration, intrathecal administration, intracranial administration, intranasal administration or subcutaneous administration, or the implantation of a slow-release device, e.g., a mini-osmotic pump, to a subject. Administration is by any route, including parenteral and transmucosal (e.g., buccal, sublingual, palatal, gingival, nasal, vaginal, rectal, or transdermal). Parenteral administration includes, e.g., intravenous, intramuscular, intra-arterial, intradermal, subcutaneous, intraperitoneal, intraventricular, and intracranial. Other modes of delivery include, but are not limited to, the use of liposomal formulations, intravenous infusion, transdermal patches, etc. By "co-administer" it is meant that a composition described herein is administered at the same time, just prior to, or just after the administration of one or more additional therapies (e.g., anti-cancer agent, chemotherapeutic, or treatment for a neurodegenerative disease). (R)-$^2$H-pioglitazone, or a pharmaceutically acceptable salt thereof, can be administered alone or can be co-administered to the patient. Co-administration is meant to include simultaneous or sequential administration of the compound individually or in combination (more than one compound or agent). Thus, the preparations can also be combined, when desired, with other active substances (e.g., to reduce metabolic degradation).

The terms "disease," "disorder," and "condition" are used interchangeably herein.

As used herein, and unless otherwise specified, the terms "treat," "treating" and "treatment" contemplate an action that occurs while a subject is suffering from the specified disease, disorder or condition, which reduces the severity of the disease, disorder or condition, or retards or slows the progression of the disease, disorder or condition (e.g., "therapeutic treatment").

In general, an "effective amount" of a compound refers to an amount sufficient to elicit the desired biological response, e.g., to treat a condition, disease, or disorder described herein. As will be appreciated by those of ordinary skill in this art, the effective amount of a compound of the disclosure may vary depending on such factors as the desired biological endpoint, the pharmacokinetics of the compound, the disease being treated, the mode of administration, and the age, weight, health, and condition of the subject.

"Pioglitazone" as used herein refers to compound (A) below which is a racemic (1:1) mixture of (R)- and (S)-enantiomers and as a bulk material has approximately the natural abundance of deuterium at each hydrogen atom position. Analogs and/or enantiomers of pioglitazone may be specified herein, for example "deuterium-enriched (R)-pioglitazone."

(A)

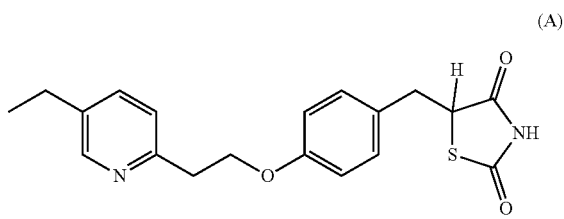 [SMILES: CCc1ccc(CCOc2ccc(CC3SC(=O)NC3=O)cc2)nc1]

Deuterium-Enriched (R)-Pioglitazone

Deuterium-enriched (R)-pioglitazone, as depicted in formula (I), is a MPC inhibitor:

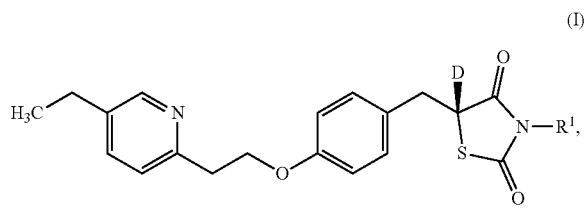

(I)

wherein R¹ is H or D.

As depicted above, the deuterium-enriched (R)-pioglitazone described herein contains deuterium enrichment at the chiral center of pioglitazone and optionally in other locations in the compound (e.g., the thiazolidinedione nitrogen). Without wishing to be bound by theory, it is thought that deuterium-enrichment at the chiral center reduces or inhibits the rate at which the two enantiomers of pioglitazone may interconvert.

Methods of chemically synthesizing deuterium-enriched (R)-pioglitazone and preparing the crystalline salt forms described herein are provided in Examples 1, 2, and 3.

In certain embodiments, the abundance of deuterium at the chiral center is about 30% to about 100%, about 40% to about 100%, about 50% to about 100%, about 60% to about 100%, about 70% to about 100%, about 75% to about 100%, about 80% to about 100%, about 85% to about 100%, about 90% to about 100%, about 95% to about 100%, about 30% to about 95%, about 30% to about 90%, about 30% to about 85%, about 30% to about 80%, about 30% to about 75%, about 30% to about 70%, about 30% to about 60%, about 30% to about 50%, about 30% to about 40%, about 40% to about 95%, about 40% to about 90%, about 40% to about 85%, about 40% to about 80%, about 40% to about 75%, about 40% to about 70%, about 40% to about 60%, about 40% to about 50%, about 50% to about 95%, about 50% to about 90%, about 50% to about 85%, about 50% to about 80%, about 50% to about 75%, about 50% to about 70%, about 50% to about 60%, about 60% to about 95%, about 60% to about 90%, about 60% to about 85%, about 60% to about 80%, about 60% to about 75%, about 60% to about 70%, about 70% to about 95%, about 70% to about 90%, about 70% to about 85%, about 70% to about 80%, about 70% to about 75%, about 75% to about 95%, about 75% to about 90%, about 75% to about 85%, about 75% to about 80%, about 80% to about 95%, about 80% to about 90%, about 80% to about 85%, about 85% to about 95%, about 85% to about 90%, or about 90% to about 95%.

In certain embodiments, the abundance of deuterium at the chiral center is at least 30%, at least 40%, at least 50%, at least 60%, at least 70%, at least 75%, at least 80%, at least 85%, at least 90%, at least 91%, at least 92%, at least 93%, at least 94%, at least 95%, at least 95%, at least 96%, at least 97%, at least 98%, or at least 99%.

In certain embodiments, the abundance of deuterium at the chiral center is about 30%, about 31%, about 32%, about 33%, about 34%, about 35%, about 36%, about 37%, about 38%, about 39%, about 40%, about 41%, about 42%, about 43%, about 44%, about 45%, about 46%, about 47%, about 48%, about 49%, about 50%, about 51%, about 52%, about 53%, about 54%, about 55%, about 56%, about 57%, about 58%, about 59%, about 60%, about 61%, about 62%, about 63%, about 64%, about 65%, about 66%, about 67%, about 68%, about 69%, about 70%, about 71%, about 72%, about 73%, about 74%, about 75%, about 76%, about 77%, about 78%, about 79%, about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, about 99%, or about 100%.

In certain embodiments, the abundance of deuterium at R¹ is 0.015% to about 100%, about 10% to about 100%, about 20% to about 100%, about 30% to about 100%, about 40% to about 100%, about 50% to about 100%, about 60% to about 100%, about 70% to about 100%, about 75% to about 100%, about 80% to about 100%, about 85% to about 100%, about 90% to about 100%, about 95% to about 100%, 0.015% to about 95%, 0.015% to about 90%, 0.015% to about 85%, 0.015% to about 80%, 0.015% to about 75%, 0.015% to about 70%, 0.015% to about 60%, 0.015% to about 50%, 0.015% to about 40%, 0.015% to about 30%, 0.015% to about 20%, 0.015% to about 10%, about 10% to about 95%, about 10% to about 90%, about 10% to about 85%, about 10% to about 80%, about 10% to about 75%, about 10% to about 70%, about 10% to about 60%, about 10% to about 50%, about 10% to about 40%, about 10% to about 30%, about 10% to about 20%, about 20% to about 95%, about 20% to about 90%, about 20% to about 85%, about 20% to about 80%, about 20% to about 75%, about 20% to about 70%, about 20% to about 60%, about 20% to about 50%, about 20% to about 40%, about 20% to about 30%, about 30% to about 95%, about 30% to about 90%, about 30% to about 85%, about 30% to about 80%, about 30% to about 75%, about 30% to about 70%, about 30% to about 60%, about 30% to about 50%, about 30% to about 40%, about 40% to about 95%, about 40% to about 90%, about 40% to about 85%, about 40% to about 80%, about 40% to about 75%, about 40% to about 70%, about 40% to about 60%, about 40% to about 50%, about 50% to about 95%, about 50% to about 90%, about 50% to about 85%, about 50% to about 80%, about 50% to about 75%, about 50% to about 70%, about 50% to about 60%, about 60% to about 95%, about 60% to about 90%, about 60% to about 85%, about 60% to about 80%, about 60% to about 75%, about 60% to about 70%, about 70% to about 95%, about 70% to about 90%, about 70% to about 85%, about 70% to about 80%, about 70% to about 75%, about 75% to about 95%, about 75% to about 90%, about 75% to about 85%, about 75% to about 80%, about 80% to about 95%, about 80% to about 90%, about 80% to about 85%, about 85% to about 95%, about 85% to about 90%, or about 90% to about 95%.

In certain embodiments, the abundance of deuterium at R¹ is at least 5%, at least 10%, at least 20%, at least 30%, at least 40%, at least 50%, at least 60%, at least 70%, at least 75%, at least 80%, at least 85%, at least 90%, at least 91%, at least 92%, at least 93%, at least 94%, at least 95%, at least 95%, at least 96%, at least 97%, at least 98%, or at least 99%.

In certain embodiments, the abundance of deuterium at R¹ is about 1%, about 2%, about 3%, about 4%, about 5%, about 6%, about 7%, about 8%, about 9%, about 10%, about 11%, about 12%, about 13%, about 14%, about 15%, about 16%, about 17%, about 18%, about 19%, about 20%, about 21%, about 22%, about 23%, about 24%, about 25%, about 26%, about 27%, about 28%, about 29%, about 30%, about 31%, about 32%, about 33%, about 34%, about 35%, about 36%, about 37%, about 38%, about 39%, about 40%, about 41%, about 42%, about 43%, about 44%, about 45%, about 46%, about 47%, about 48%, about 49%, about 50%, about 51%, about 52%, about 53%, about 54%, about 55%, about 56%, about 57%, about 58%, about 59%, about 60%, about 61%, about 62%, about 63%, about 64%, about 65%, about 66%, about 67%, about 68%, about 69%, about 70%, about 71%, about 72%, about 73%, about 74%, about 75%, about 76%, about 77%, about 78%, about 79%, about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, about 99%, or about 100%.

In certain embodiments, the total deuterium abundance in the compound of formula (I) is about 0.3 to about 4, about 0.5 to about 4, about 1 to about 4, about 1.2 to about 4, about 1.3 to about 4, about 1.4 to about 4, about 1.6 to about 4, about 1.8 to about 4, about 2 to about 4, about 2.2 to about 4, about 2.4 to about 4, about 2.6 to about 4, about 2.8 to about 4, about 3 to about 4, about 3.2 to about 4, about 3.4 to about 4, about 3.6 to about 4, about 3.8 to about 4, about 0.3 to about 3.8, about 0.3 to about 3.6, about 0.3 to about 3.4, about 0.3 to about 3.2, about 0.3 to about 3, about 0.3 to about 2.8, about 0.3 to about 2.6, about 0.3 to about 2.4, about 0.3 to about 2.2, about 0.3 to about 2, about 0.3 to about 1.8, about 0.3 to about 1.6, about 0.3 to about 1.4, about 0.3 to about 1.2, about 0.3 to about 1, about 0.3 to about 0.5, about 0.5 to about 3.8, about 0.5 to about 3.6, about 0.5 to about 3.4, about 0.5 to about 3.2, about 0.5 to about 3, about 0.5 to about 2.8, about 0.5 to about 2.6, about 0.5 to about 2.4, about 0.5 to about 2.2, about 0.5 to about 2, about 0.5 to about 1.8, about 0.5 to about 1.6, about 0.5 to about 1.4, about 0.5 to about 1.2, about 0.5 to about 1, about 1 to about 3.8, about 1 to about 3.6, about 1 to about 3.4, about 1 to about 3.2, about 1 to about 3, about 1 to about 2.8, about 1 to about 2.6, about 1 to about 2.4, about 1 to about 2.2, about 1 to about 2, about 1 to about 1.8, about 1 to about 1.6, about 1 to about 1.4, about 1 to about 1.2, about 1.2 to about 3.8, about 1.2 to about 3.6, about 1.2 to about 3.4, about 1.2 to about 3.2, about 1.2 to about 3, about 1.2 to about 2.8, about 1.2 to about 2.6, about 1.2 to about 2.4, about 1.2 to about 2.2, about 1.2 to about 2, about 1.2 to about 1.8, about 1.2 to about 1.6, about 1.2 to about 1.4, about 1.2 to about 1.3, about 1.3 to about 3.8, about 1.3 to about 3.6, about 1.3 to about 3.4, about 1.3 to about 3.2, about 1.3 to about 3, about 1.3 to about 2.8, about 1.3 to about 2.6, about 1.3 to about 2.4, about 1.3 to about 2.2, about 1.3 to about 2, about 1.3 to about 1.8, about 1.3 to about 1.6, about 1.3 to about 1.4, about 1.4 to about 3.8, about 1.4 to about 3.6, about 1.4 to about 3.4, about 1.4 to about 3.2, about 1.4 to about 3, about 1.4 to about 2.8, about 1.4 to about 2.6, about 1.4 to about 2.4, about 1.4 to about 2.2, about 1.4 to about 2, about 1.4 to about 1.8, about 1.4 to about 1.6, about 1.6 to about 3.8, about 1.6 to about 3.6, about 1.6 to about 3.4, about 1.6 to about 3.2, about 1.6 to about 3, about 1.6 to about 2.8, about 1.6 to about 2.6, about 1.6 to about 2.4, about 1.6 to about 2.2, about 1.6 to about 2, about 1.6 to about 1.8, about 1.8 to about 3.8, about 1.8 to about 3.6, about 1.8 to about 3.4, about 1.8 to about 3.2, about 1.8 to about 3, about 1.8 to about 2.8, about 1.8 to about 2.6, about 1.8 to about 2.4, about 1.8 to about 2.2, about 1.8 to about 2, about 2 to about 3.8, about 2 to about 3.6, about 2 to about 3.4, about 2 to about 3.2, about 2 to about 3, about 2 to about 2.8, about 2 to about 2.6, about 2 to about 2.4, about 2 to about 2.2, about 2.2 to about 3.8, about 2.2 to about 3.6, about 2.2 to about 3.4, about 2.2 to about 3.2, about 2.2 to about 3, about 2.2 to about 2.8, about 2.2 to about 2.6, about 2.2 to about 2.4, about 2.4 to about 3.8, about 2.4 to about 3.6, about 2.4 to about 3.4, about 2.4 to about 3.2, about 2.4 to about 3, about 2.4 to about 2.8, about 2.4 to about 2.6, about 2.6 to about 3.8, about 2.6 to about 3.6, about 2.6 to about 3.4, about 2.6 to about 3.2, about 2.6 to about 3, about 2.6 to about 2.8, about 2.8 to about 3.8, about 2.8 to about 3.6, about 2.8 to about 3.4, about 2.8 to about 3.2, about 2.8 to about 3, about 3 to about 3.8, about 3 to about 3.6, about 3 to about 3.4, about 3 to about 3.2, about 3.2 to about 3.8, about 3.2 to about 3.6, about 3.2 to about 3.4, about 3.4 to about 3.8, about 3.4 to about 3.6, or about 3.6 to about 3.8. In certain embodiments, the total deuterium abundance in the compound of formula (I) is about 1.3 to about 4. In certain embodiments, the total deuterium abundance in the compound of formula (I) is about 1.8 to about 3.

In certain embodiments, the deuterium-enriched (R)-pioglitazone described herein has an enantiomeric excess of about 70% to about 100%, about 75% to about 100%, about 80% to about 100%, about 85% to about 100%, about 90% to about 100%, about 95% to about 100%, about 70% to about 95%, about 70% to about 90%, about 70% to about 85%, about 70% to about 80%, about 70% to about 75%, about 75% to about 95%, about 75% to about 90%, about 75% to about 85%, about 75% to about 80%, about 80% to about 95%, about 80% to about 90%, about 80% to about 85%, about 85% to about 95%, about 85% to about 90%, or about 90% to about 95%.

In certain embodiments, the deuterium-enriched (R)-pioglitazone described herein has an enantiomeric excess of at least 70%, at least 75%, at least 80%, at least 85%, at least 90%, at least 91%, at least 92%, at least 93%, at least 94%, at least 95%, at least 96%, at least 97%, at least 98%, or at least 99%.

In certain embodiments, the deuterium-enriched (R)-pioglitazone described herein has an enantiomeric excess of about 70%, about 71%, about 72%, about 73%, about 74%, about 75%, about 76%, about 77%, about 78%, about 79%, about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, about 99%, or about 100%. In certain embodiments, the deuterium-enriched (R)-pioglitazone described herein is enantiopure.

In various embodiments, provided herein is the free-base form of deuterium-enriched (R)-pioglitazone.

In various embodiments, provided herein is a pharmaceutically acceptable salt of deuterium-enriched (R)-pioglitazone. In certain embodiments, the pharmaceutically acceptable salt of deuterium-enriched (R)-pioglitazone is a deuterium chloride salt. In certain embodiments, the pharmaceutically acceptable salt of deuterium-enriched (R)-pioglitazone is a hydrochloride salt.

Deuterium Chloride (DCl) Salt of Deuterium-Enriched (R)-Pioglitazone

In one aspect, the invention provides a deuterium chloride salt of the deuterium-enriched compound of formula (I):

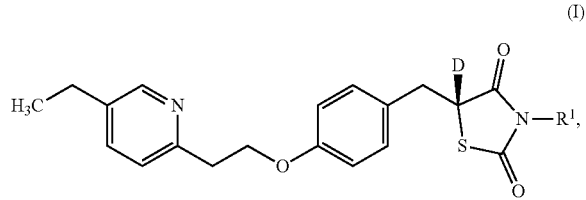

wherein $R^1$ is H or D, provided that the total deuterium abundance in the compound of formula (I) is about 1.3 to about 4.

In certain embodiments, the deuterium chloride salt is a crystalline deuterium chloride salt. In certain embodiments, the crystalline deuterium chloride salt is an anhydrous crystalline deuterium chloride salt.

In another aspect, the invention provides a crystalline deuterium chloride salt of the deuterium-enriched compound of formula (I)

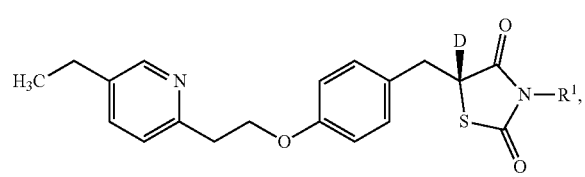

(I)

wherein $R^1$ is H or D, provided that the total deuterium abundance in the compound of formula (I) is about 1.3 to about 4, and wherein the crystalline deuterium chloride salt is characterized by an X-ray powder diffraction pattern comprising peaks at the following diffraction angles (2θ): 15.8°±0.2°, 22.8°±0.2°, and 26.0°±0.2°.

In certain embodiments, the crystalline deuterium chloride salt is characterized by an X-ray powder diffraction pattern comprising peaks at the following diffraction angles (2θ): 20.0°±0.2°, 20.8°±0.2°, and 22.8°±0.2°. In certain embodiments, the crystalline deuterium chloride salt is characterized by an X-ray powder diffraction pattern comprising peaks at the following diffraction angles (2θ): 15.8°±0.2°, 20.0°±0.2°, 20.8°±0.2°, 22.8°±0.2°, and 26.0°±0.2°. In certain embodiments, the crystalline deuterium chloride salt is characterized by an X-ray powder diffraction pattern comprising peaks at the following diffraction angles (2θ): 8.6°±0.2°, 8.8° 0.2°, 12.8°±0.2°, 12.9°±0.2°, 15.8°±0.2°, 18.8°±0.2°, 18.9°±0.2°, 19.7°±0.2°, 20.0°±0.2°, 20.8°±0.2°, 22.8°±0.2°, 26.0°±0.2°, and 31.3°±0.2°.

In certain embodiments, the crystalline deuterium chloride salt is characterized by the X-ray powder diffraction pattern expressed in terms of diffraction angle 2θ and optionally relative intensity (expressed as a percentage with respect to the most intense peak) as set forth in Table 1.

TABLE 1

X-ray Powder Diffraction Data (XRPD) of the Crystalline DCl Salt

| 2θ (°) | d value (Å) | Intensity (%) |
|---|---|---|
| 8.6 | 10.27 | 18 |
| 8.8 | 10.07 | 17 |
| 12.8 | 6.93 | 22 |
| 12.9 | 6.87 | 26 |
| 15.9 | 5.59 | 4 |
| 18.7 | 4.73 | 18 |
| 18.9 | 4.70 | 16 |
| 19.7 | 4.51 | 18 |
| 20.0 | 4.45 | 34 |
| 20.8 | 4.26 | 56 |
| 21.2 | 4.19 | 13 |
| 22.1 | 4.02 | 8 |
| 22.8 | 3.89 | 100 |
| 23.7 | 3.75 | 3 |
| 25.6 | 3.47 | 5 |
| 26.0 | 3.43 | 20 |
| 26.7 | 3.34 | 9 |
| 27.3 | 3.26 | 6 |

TABLE 1-continued

X-ray Powder Diffraction Data (XRPD) of the Crystalline DCl Salt

| 2θ (°) | d value (Å) | Intensity (%) |
|---|---|---|
| 28.1 | 3.18 | 12 |
| 29.8 | 3.00 | 12 |
| 31.3 | 2.86 | 21 |
| 32.1 | 2.79 | 10 |
| 32.3 | 2.77 | 5 |
| 33.4 | 2.68 | 3 |
| 33.6 | 2.66 | 3 |
| 34.4 | 2.60 | 4 |
| 36.0 | 2.50 | 3 |

In certain embodiments, the crystalline deuterium chloride salt is characterized by an X-ray powder diffraction pattern substantially the same as shown in FIG. 1A.

In certain embodiments, the crystalline deuterium chloride salt exists in a monoclinic crystal system and has a P2₁/c space group. In certain embodiments, the crystalline deuterium chloride salt is characterized by the crystallographic unit cell parameters as set forth in Table 2.

TABLE 2

Unit Cell Parameters of the Crystalline Form of Compound of formula (V)

| a [Å] | 10.1319 (9) |
|---|---|
| b [Å] | 9.4067 (9) |
| c [Å] | 10.3231 (6) |
| β [°] | 94.397 (3) |
| V [Å³] | 980.98 (14) |
| Z | 2 |
| $D_c$ [g/cm³] | 1.330 |

Figure 3:
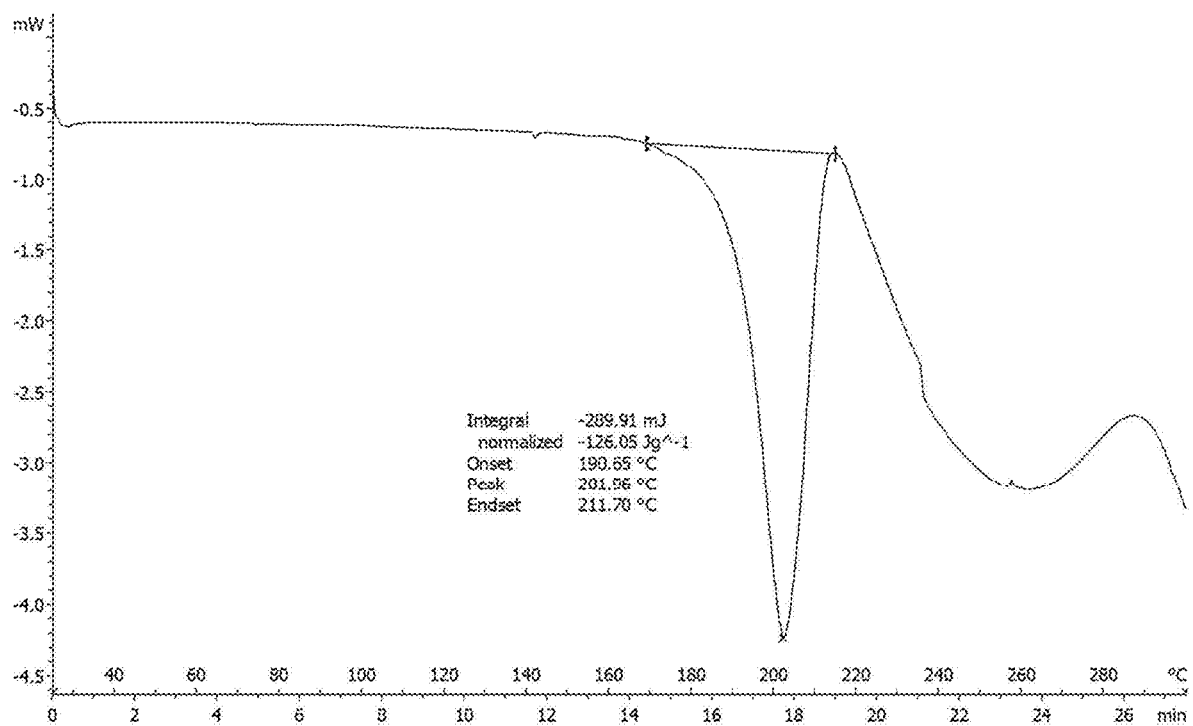
FIG. 3 is an exemplary differential scanning calorimetry (DSC) curve of the crystalline deuterium chloride salt of deuterium-enriched (R)-pioglitazone.

The crystalline deuterium chloride salt may also be characterized according to the temperature of melting point onset. In certain embodiments, the crystalline deuterium chloride salt has a melting point onset as determined by differential scanning calorimetry at about 190° C. to about 200° C. In certain embodiments, the crystalline deuterium chloride salt has a melting point onset as determined by differential scanning calorimetry at about 191° C. In certain embodiments, the crystalline deuterium chloride salt exhibits a melting endotherm with a peak at about 200° C. to about 210° C. In certain embodiments, the crystalline deuterium chloride salt exhibits a melting endotherm with a peak at about 204° C. In certain embodiments, the crystalline deuterium chloride salt has a differential scanning calorimetry curve substantially the same as shown in FIG. 3.

In certain embodiments, the crystalline deuterium chloride salt has a chemical purity of about 70% to about 100%, about 75% to about 100%, about 80% to about 100%, about 85% to about 100%, about 90% to about 100%, about 95% to about 100%, about 70% to about 95%, about 70% to about 90%, about 70% to about 85%, about 70% to about 80%, about 70% to about 75%, about 75% to about 95%, about 75% to about 90%, about 75% to about 85%, about 75% to about 80%, about 80% to about 95%, about 80% to about 90%, about 80% to about 85%, about 85% to about 95%, about 85% to about 90%, or about 90% to about 95%.

In certain embodiments, the crystalline deuterium chloride salt has a chemical purity of at least 70%, at least 75%, at least 80%, at least 85%, at least 90%, at least 91%, at least 92%, at least 93%, at least 94%, at least 95%, at least 96%, at least 97%, at least 98%, at least 99%, at least 99.1%, at least 99.2%, at least 99.3%, at least 99.4%, at least 99.5%, at least 99.6%, at least 99.7%, at least 99.8%, or at least 99.9%.

In certain embodiments, the crystalline deuterium chloride salt has a chemical purity of about 70%, about 71%, about 72%, about 73%, about 74%, about 75%, about 76%, about 77%, about 78%, about 79%, about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, about 99%, about 99.1%, about 99.2%, about 99.3%, about 99.4%, about 99.5%, about 99.6%, about 99.7%, about 99.8%, about 99.9%, or about 100%.

In various embodiments, the invention provides a pharmaceutical material comprising particles of a crystalline deuterium chloride salt of a deuterium-enriched compound of formula (I)

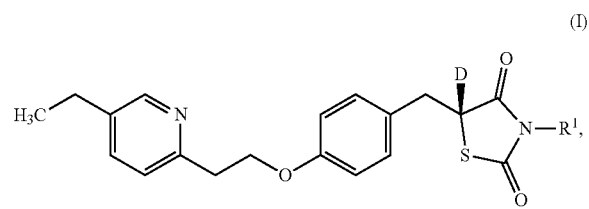

wherein $R^1$ is H or D, provided that the total deuterium abundance in the compound of formula (I) is about 1.3 to about 4, and
wherein the particles in the composition have a crystal shape selected from hexagonal, rod, and combinations thereof.

In certain embodiments, the particles have a particle size distribution which is defined by a d(0.1) of about 10 μm to 200 μm, about 20 μm to 200 μm, about 40 μm to 200 μm, about 60 μm to 200 μm, about 80 μm to 200 μm, about 100 μm to 200 μm, about 120 μm to 200 μm, about 140 μm to 200 μm, about 160 μm to 200 μm, about 180 μm to 200 μm, about 10 μm to 180 μm, about 10 μm to 160 μm, about 10 μm to 140 μm, about 10 μm to 120 μm, about 10 μm to 100 μm, about 10 μm to 80 μm, about 10 μm to 60 μm, about 10 μm to 40 μm, about 10 μm to 20 μm, about 20 μm to 180 μm, about 20 μm to 160 μm, about 20 μm to 140 μm, about 20 μm to 120 μm, about 20 μm to 100 μm, about 20 μm to 80 μm, about 20 μm to 60 μm, about 20 μm to 40 μm, about 40 μm to 180 μm, about 40 μm to 160 μm, about 40 μm to 140 μm, about 40 μm to 120 μm, about 40 μm to 100 μm, about 40 μm to 80 μm, about 40 μm to 60 μm, about 60 μm to 180 μm, about 60 μm to 160 μm, about 60 μm to 140 μm, about 60 μm to 120 μm, about 60 μm to 100 μm, about 60 μm to 80 μm, about 80 μm to 180 μm, about 80 μm to 160 μm, about 80 μm to 140 μm, about 80 μm to 120 μm, about 80 μm to 100 μm, about 100 μm to 180 μm, about 100 μm to 160 μm, about 100 μm to 140 μm, about 100 μm to 120 μm, about 120 μm to 180 μm, about 120 μm to 160 μm, about 120 μm to 140 μm, about 140 μm to 180 μm, about 140 μm to 160 μm, or about 160 μm to 180 μm. In certain embodiments, the particles have a particle size distribution which is defined by a d(0.1) of about 10 μm to about 200 μm.

In certain embodiments, the particles have a particle size distribution which is defined by a d(0.5) of about 10 μm to about 400 μm, about 50 μm to about 400 μm, about 75 μm to about 400 μm, about 100 μm to about 400 μm, about 125 μm to about 400 μm, about 150 μm to about 400 μm, about 175 μm to about 400 μm, about 200 μm to about 400 μm, about 225 μm to about 400 μm, about 250 μm to about 400 μm, about 275 μm to about 400 μm, about 300 μm to about 400 μm, about 325 μm to about 400 μm, about 350 μm to about 400 μm, about 375 μm to about 400 μm, about 10 μm to about 375 μm, about 10 μm to about 350 μm, about 10 μm to about 325 μm, about 10 μm to about 300 μm, about 10 μm to about 275 μm, about 10 μm to about 250 μm, about 10 μm to about 225 μm, about 10 μm to about 200 μm, about 50 μm to about 375 μm, about 50 μm to about 350 μm, about 50 μm to about 325 μm, about 50 μm to about 300 μm, about 50 μm to about 275 μm, about 50 μm to about 250 μm, about 50 μm to about 225 μm, about 50 μm to about 200 μm, about 50 μm to about 175 μm, about 50 μm to about 150 μm, about 50 μm to about 125 μm, about 50 μm to about 100 μm, about 50 μm to about 75 μm, about 75 μm to about 375 μm, about 75 μm to about 350 μm, about 75 μm to about 325 μm, about 75 μm to about 300 μm, about 75 μm to about 275 μm, about 75 μm to about 250 μm, about 75 μm to about 225 μm, about 75 μm to about 375 μm, about 75 μm to about 350 μm, about 75 μm to about 325 μm, about 75 μm to about 300 μm, about 75 μm to about 275 μm, about 75 μm to about 250 μm, about 75 μm to about 225 μm, about 75 μm to about 200 μm, about 75 μm to about 175 μm, about 75 μm to about 150 μm, about 75 μm to about 125 μm, about 75 μm to about 100 μm, about 100 μm to about 375 μm, about 100 μm to about 350 μm, about 100 μm to about 325 μm, about 100 μm to about 300 μm, about 100 μm to about 275 μm, about 100 μm to about 250 μm, about 100 μm to about 225 μm, about 100 μm to about 200 μm, about 100 μm to about 175 μm, about 100 μm to about 150 μm, about 100 μm to about 125 μm, about 125 μm to about 375 μm, about 125 μm to about 350 μm, about 125 μm to about 325 μm, about 125 μm to about 300 μm, about 125 μm to about 275 μm, about 125 μm to about 250 μm, about 125 μm to about 225 μm, about 125 μm to about 200 μm, about 125 μm to about 175 μm, about 125 μm to about 150 μm, about 150 μm to about 375 μm, about 150 μm to about 350 μm, about 150 μm to about 325 μm, about 150 μm to about 300 μm, about 150 μm to about 275 μm, about 150 μm to about 250 μm, about 150 μm to about 225 μm, about 150 μm to about 200 μm, about 150 μm to about 175 μm, about 175 μm to about 375 μm, about 175 μm to about 350 μm, about 175 μm to about 325 μm, about 175 μm to about 300 μm, about 175 μm to about 275 μm, about 175 μm to about 250 μm, about 175 μm to about 225 μm, about 175 μm to about 200 μm, about 200 μm to about 375 μm, about 200 μm to about 350 μm, about 200 μm to about 325 μm, about 200 μm to about 300 μm, about 200 μm to about 275 μm, about 200 μm to about 250 μm, about 200 μm to about 225 μm, about 225 μm to about 375 μm, about 225 μm to about 350 μm, about 225 μm to about 325 μm, about 225 μm to about 300 μm, about 225 μm to about 275 μm, about 225 μm to about 250 μm, about 250 μm to about 375 μm, about 250 μm to about 350 μm, about 250 μm to about 325 μm, about 250 μm to about 300 μm, about 250 μm to about 275 μm, about 275 μm to about 375 μm, about 275 μm to about 350 μm, about 275 μm to about 325 μm, about 275 μm to about 300 μm, about 300 μm to about 375 μm, about 300 μm to about 350 μm, about 300 μm to about 325 μm, about 325 μm to about 375 μm, about 325 μm to about 350 μm, or about 350 μm to about 375 μm. In certain embodiments, the particles have a particle size distribution which is defined by a d(0.5) about 10 μm to about 400 μm.

In certain embodiments, the particles have a particle size distribution which is defined by a d(0.9) of about 10 μm to about 800 μm, about 50 μm to about 800 μm, about 100 μm to about 800 μm, about 150 μm to about 800 μm, about 200 μm to about 800 μm, about 250 μm to about 800 μm, about 300 μm to about 800 μm, about 350 μm to about 800 μm, about 400 μm to about 800 μm, about 450 μm to about 800

μm, about 500 μm to about 800 μm, about 550 μm to about 800 μm, about 600 μm to about 800 μm, about 650 μm to about 800 μm, about 700 μm to about 800 μm, about 750 μm to about 800 μm, about 150 μm to about 750 μm, about 150 μm to about 700 μm, about 150 μm to about 650 μm, about 150 μm to about 600 μm, about 150 μm to about 550 μm, about 150 μm to about 500 μm, about 150 μm to about 450 μm, about 150 μm to about 400 μm, about 150 μm to about 350 μm, about 150 μm to about 300 μm, about 150 μm to about 250 μm, about 150 μm to about 200 μm, about 200 μm to about 750 μm, about 200 μm to about 700 μm, about 200 μm to about 650 μm, about 200 μm to about 600 μm, about 200 μm to about 550 μm, about 200 μm to about 500 μm, about 200 μm to about 450 μm, about 200 μm to about 400 μm, about 200 μm to about 350 μm, about 200 μm to about 300 μm, about 200 μm to about 250 μm, about 250 μm to about 750 μm, about 250 μm to about 700 μm, about 250 μm to about 650 μm, about 250 μm to about 600 μm, about 250 μm to about 550 μm, about 250 μm to about 500 μm, about 250 μm to about 450 μm, about 250 μm to about 400 μm, about 250 μm to about 350 μm, about 250 μm to about 300 μm, about 300 μm to about 750 μm, about 300 μm to about 700 μm, about 300 μm to about 650 μm, about 300 μm to about 600 μm, about 300 μm to about 550 μm, about 300 μm to about 500 μm, about 300 μm to about 450 μm, about 300 μm to about 400 μm, about 300 μm to about 350 μm, about 350 μm to about 750 μm, about 350 μm to about 700 μm, about 350 μm to about 650 μm, about 350 μm to about 600 μm, about 350 μm to about 550 μm, about 350 μm to about 500 μm, about 350 μm to about 450 μm, about 350 μm to about 400 μm, about 400 μm to about 750 μm, about 400 μm to about 700 μm, about 400 μm to about 650 μm, about 400 μm to about 600 μm, about 400 μm to about 550 μm, about 400 μm to about 500 μm, about 400 μm to about 450 μm, about 450 μm to about 750 μm, about 450 μm to about 700 μm, about 450 μm to about 650 μm, about 450 μm to about 600 μm, about 450 μm to about 550 μm, about 450 μm to about 500 μm, about 500 μm to about 750 μm, about 500 μm to about 700 μm, about 500 μm to about 650 μm, about 500 μm to about 600 μm, about 500 μm to about 550 μm, about 550 μm to about 750 μm, about 550 μm to about 700 μm, about 550 μm to about 650 μm, about 550 μm to about 600 μm, about 600 μm to about 750 μm, about 600 μm to about 700 μm, about 600 μm to about 650 μm, about 650 μm to about 750 μm, about 650 μm to about 700 μm, or about 700 μm to about 750 μm. In certain embodiments, the particles have a particle size distribution which is defined by a d(0.9) of about 10 μm to about 800 μm.

In various embodiments, the invention provides a pharmaceutical material comprising particles of a crystalline deuterium chloride salt of a deuterium-enriched compound of formula (I)

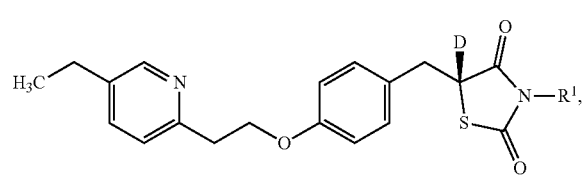

wherein $R^1$ is H or D, provided that the total deuterium abundance in the compound of formula (I) is about 1.3 to about 4, and wherein the particles have a particle size distribution which is defined by a d(0.9) of about 10 μm to about 800 μm, preferably below 500 μm.

Hydrochloride (HCl) Salt of Deuterium-Enriched Pioglitazone

In one aspect, the invention provides a crystalline hydrochloride salt of the deuterium-enriched compound of formula (I-A):

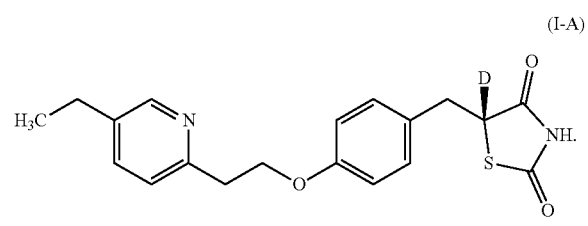 [SMILES: [2H][C@]1(Cc2ccc(OCCc3ccc(CC)cn3)cc2)SC(=O)NC1=O]

In certain embodiments, the crystalline hydrochloride salt is characterized by an X-ray powder diffraction pattern comprising peaks at the following diffraction angles (2θ): 15.8°±0.2°, 22.8°±0.2°, and 26.0°±0.2°. In certain embodiments, the crystalline hydrochloride salt is characterized by an X-ray powder diffraction pattern comprising peaks at the following diffraction angles (2θ): 20.0°±0.2°, 20.8°±0.2°, and 22.8°±0.2°.

In various embodiments, the invention provides a crystalline hydrochloride salt of the compound of formula (I-A)

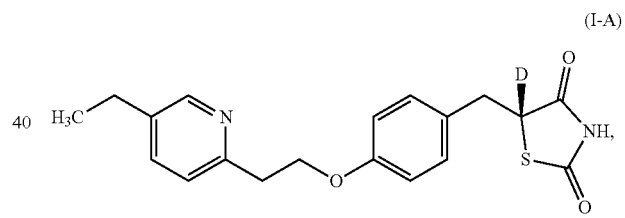

wherein the crystalline hydrochloride salt is characterized by an X-ray powder diffraction pattern comprising peaks at the following diffraction angles (2θ): 15.8°±0.2°, 22.8°±0.2°, and 26.0°±0.2°.

In certain embodiments, the crystalline hydrochloride salt is characterized by an X-ray powder diffraction pattern comprising peaks at the following diffraction angles (2θ): 15.8°±0.2°, 20.0°±0.2°, 20.8°±0.2°, 22.8°±0.2°, and 26.0°±0.2°. In certain embodiments, the crystalline hydrochloride salt is characterized by an X-ray powder diffraction pattern comprising peaks at the following diffraction angles (2θ): 8.6°±0.2°, 8.8°±0.2°, 12.8°±0.2°, 12.9°±0.2°, 15.9°±0.2°, 18.8°±0.2°, 19.7°±0.2°, 20.0°±0.2°, 20.8°±0.2°, 22.8°±0.2°, 26.0°±0.2°, 28.1°±0.2°, and 31.3°±0.2°.

In certain embodiments, the crystalline hydrochloride salt is characterized by the X-ray powder diffraction pattern expressed in terms of diffraction angle 2θ and optionally relative intensity (expressed as a percentage with respect to the most intense peak) as set forth in Table 3.

TABLE 3

X-ray Powder Diffraction Data of the Crystalline Hydrochloride Salt

| 2θ (°) | d value (Å) | Intensity (%) |
|---|---|---|
| 8.6 | 10.27 | 32 |
| 8.8 | 10.08 | 31 |
| 12.8 | 6.93 | 30 |
| 12.9 | 6.87 | 27 |
| 15.9 | 5.59 | 6 |
| 18.7 | 4.73 | 25 |
| 18.9 | 4.70 | 12 |
| 19.7 | 4.51 | 29 |
| 20.0 | 4.45 | 80 |
| 20.8 | 4.26 | 50 |
| 21.2 | 4.19 | 18 |
| 22.1 | 4.02 | 14 |
| 22.8 | 3.89 | 100 |
| 23.7 | 3.75 | 4 |
| 25.6 | 3.47 | 6 |
| 26.0 | 3.43 | 36 |
| 26.7 | 3.34 | 9 |
| 27.3 | 3.26 | 15 |
| 28.1 | 3.17 | 30 |
| 29.8 | 3.00 | 9 |
| 31.3 | 2.86 | 19 |
| 32.1 | 2.79 | 13 |
| 32.3 | 2.77 | 7 |
| 33.4 | 2.68 | 3 |
| 33.6 | 2.66 | 3 |
| 34.4 | 2.61 | 5 |
| 36.0 | 2.50 | 5 |

Figure 6:
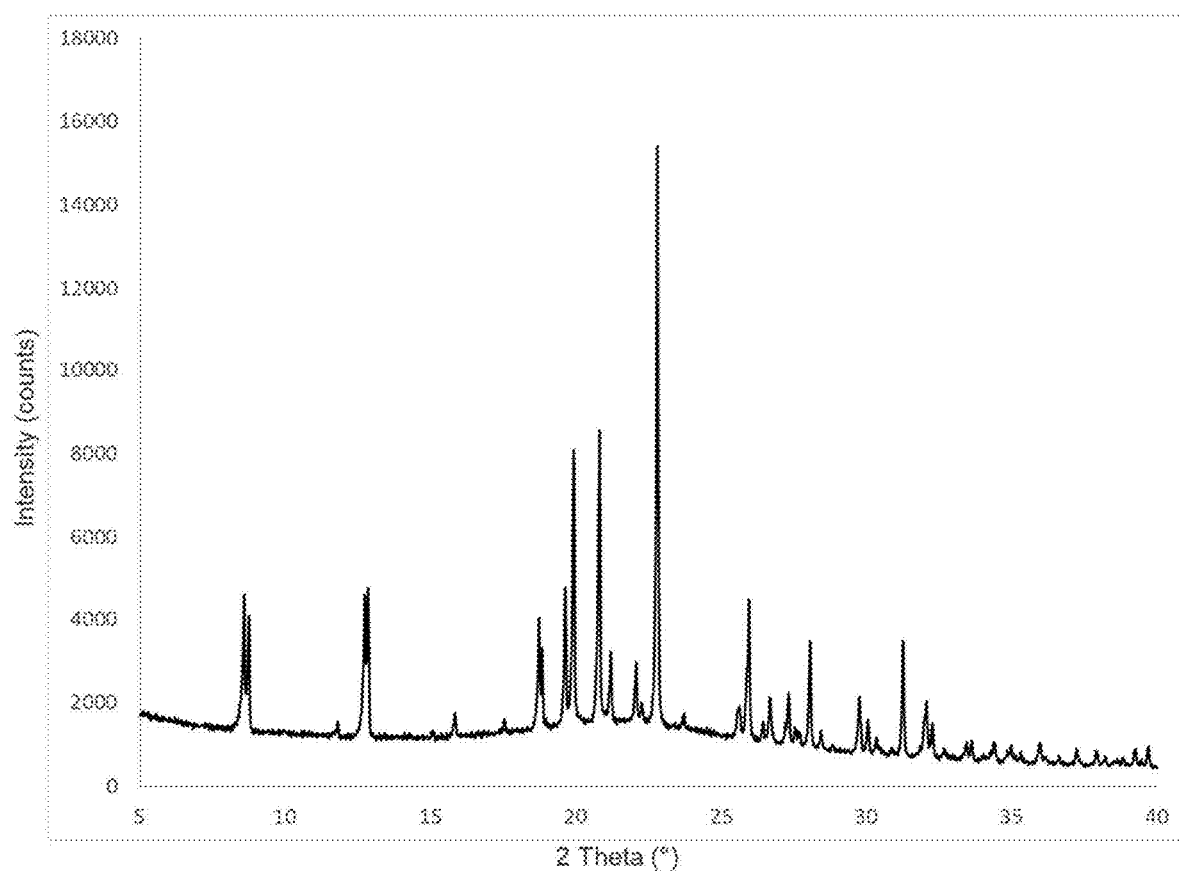
FIG. 6 an exemplary X-ray powder diffraction (XRPD) pattern of the crystalline hydrochloride salt of deuterium-enriched (R)-pioglitazone.

In certain embodiments, the crystalline hydrochloride salt is characterized by an X-ray powder diffraction pattern substantially the same as shown in FIG. 6.

Figure 8:
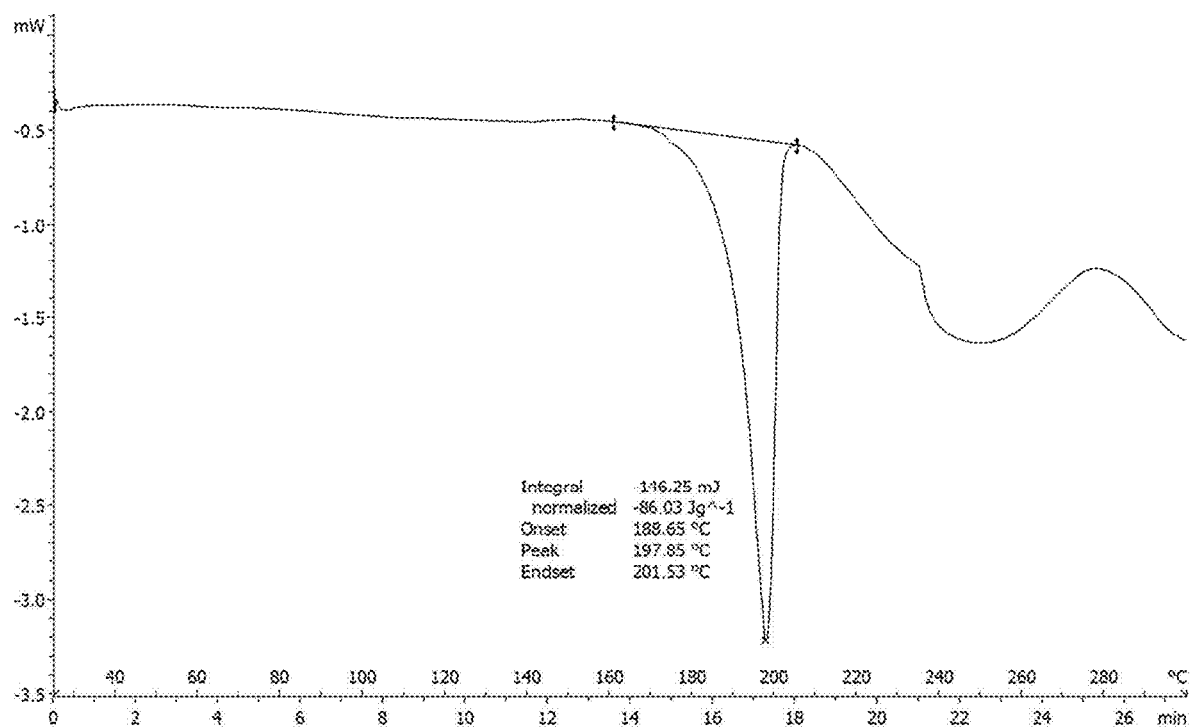
FIG. 8 is an exemplary differential scanning calorimetry (DSC) curve of the crystalline hydrochloride salt of deuterium-enriched (R)-pioglitazone.

The crystalline hydrochloride salt may also be characterized according to the temperature of melting point onset. In certain embodiments, the crystalline hydrochloride salt has a melting point onset as determined by differential scanning calorimetry at about 190° C. to about 210° C. In certain embodiments, the crystalline hydrochloride salt has a melting point onset as determined by differential scanning calorimetry at about 190° C. In certain embodiments, the crystalline hydrochloride salt exhibits a melting endotherm with a peak at about 195° C. to about 205° C. In certain embodiments, the crystalline hydrochloride salt exhibits a melting endotherm with a peak at about 200° C. In certain embodiments, the crystalline hydrochloride salt has a differential scanning calorimetry curve substantially the same as shown in FIG. 8.

In certain embodiments, the crystalline hydrochloride salt is an anhydrous crystalline hydrochloride salt.

In certain embodiments, the crystalline hydrochloride salt has a chemical purity of about 70% to about 100%, about 75% to about 100%, about 80% to about 100%, about 85% to about 100%, about 90% to about 100%, about 95% to about 100%, about 70% to about 95%, about 70% to about 90%, about 70% to about 85%, about 70% to about 80%, about 70% to about 75%, about 75% to about 95%, about 75% to about 90%, about 75% to about 85%, about 75% to about 80%, about 80% to about 95%, about 80% to about 90%, about 80% to about 85%, about 85% to about 95%, about 85% to about 90%, or about 90% to about 95%.

In certain embodiments, the crystalline hydrochloride salt has a chemical purity of at least 70%, at least 75%, at least 80%, at least 85%, at least 90%, at least 91%, at least 92%, at least 93%, at least 94%, at least 95%, at least 96%, at least 97%, at least 98%, at least 99%, at least 99.1%, at least 99.2%, at least 99.3%, at least 99.4%, at least 99.5%, at least 99.6%, at least 99.7%, at least 99.8%, or at least 99.9%.

In certain embodiments, the crystalline hydrochloride salt has a chemical purity of about 70%, about 71%, about 72%, about 73%, about 74%, about 75%, about 76%, about 77%, about 78%, about 79%, about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, about 99%, about 99.1%, about 99.2%, about 99.3%, about 99.4%, about 99.5%, about 99.6%, about 99.7%, about 99.8%, about 99.9%, or about 100%.

In various embodiments, the invention provides a pharmaceutical material comprising particles of a crystalline hydrochloride salt of the compound of formula (I-A)

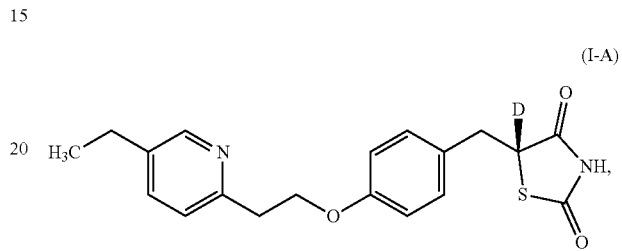

(I-A)

wherein the particles in the composition have a needle-like crystal shape.

In certain embodiments, the particles have a particle size distribution which is defined by a d(0.1) of about 10 μm to 200 μm, about 20 μm to 200 μm, about 40 μm to 200 μm, about 60 μm to 200 μm, about 80 μm to 200 μm, about 100 μm to 200 μm, about 120 μm to 200 μm, about 140 μm to 200 μm, about 160 μm to 200 μm, about 180 μm to 200 μm, about 10 μm to 180 μm, about 10 μm to 160 μm, about 10 μm to 140 μm, about 10 μm to 120 μm, about 10 μm to 100 μm, about 10 μm to 80 μm, about 10 μm to 60 μm, about 10 μm to 40 μm, about 10 μm to 20 μm, about 20 μm to 180 μm, about 20 μm to 160 μm, about 20 μm to 140 μm, about 20 μm to 120 μm, about 20 μm to 100 μm, about 20 μm to 80 μm, about 20 μm to 60 μm, about 20 μm to 40 μm, about 40 μm to 180 μm, about 40 μm to 160 μm, about 40 μm to 140 μm, about 40 μm to 120 μm, about 40 μm to 100 μm, about 40 μm to 80 μm, about 40 μm to 60 μm, about 60 μm to 180 μm, about 60 μm to 160 μm, about 60 μm to 140 μm, about 60 μm to 120 μm, about 60 μm to 100 μm, about 60 μm to 80 μm, about 80 μm to 180 μm, about 80 μm to 160 μm, about 80 μm to 140 μm, about 80 μm to 120 μm, about 80 μm to 100 μm, about 100 μm to 180 μm, about 100 μm to 160 μm, about 100 μm to 140 μm, about 100 μm to 120 μm, about 120 μm to 180 μm, about 120 μm to 160 μm, about 120 μm to 140 μm, about 140 μm to 180 μm, about 140 μm to 160 μm, or about 160 μm to 180 μm. In certain embodiments, the particles have a particle size distribution which is defined by a d(0.1) of about 10 μm to about 200 μm.

In certain embodiments, the particles have a particle size distribution which is defined by a d(0.5) of about 10 μm to about 400 μm, about 50 μm to about 400 μm, about 75 μm to about 400 μm, about 100 μm to about 400 μm, about 125 μm to about 400 μm, about 150 μm to about 400 μm, about 175 μm to about 400 μm, about 200 μm to about 400 μm, about 225 μm to about 400 μm, about 250 μm to about 400 μm, about 275 μm to about 400 μm, about 300 μm to about 400 μm, about 325 μm to about 400 μm, about 350 μm to about 400 μm, about 375 μm to about 400 μm, about 10 μm to about 375 μm, about 10 μm to about 350 μm, about 10 μm to about 325 μm, about 10 μm to about 300 μm, about 10 μm to about 275 μm, about 10 μm to about 250 μm, about 10 μm to about 225 µm, about 10 µm to about 200 µm, about 50 µm to about 375 µm, about 50 µm to about 350 µm, about 50 µm to about 325 µm, about 50 µm to about 300 µm, about 50 µm to about 275 µm, about 50 µm to about 250 µm, about 50 µm to about 225 µm, about 50 µm to about 200 µm, about 50 µm to about 175 µm, about 50 µm to about 150 µm, about 50 µm to about 125 µm, about 50 µm to about 100 µm, about 50 µm to about 75 µm, about 75 µm to about 375 µm, about 75 µm to about 350 µm, about 75 µm to about 325 µm, about 75 µm to about 300 µm, about 75 µm to about 275 µm, about 75 µm to about 250 µm, about 75 µm to about 225 µm, about 75 µm to about 375 µm, about 75 µm to about 350 µm, about 75 µm to about 325 µm, about 75 µm to about 300 µm, about 75 µm to about 275 µm, about 75 µm to about 250 µm, about 75 µm to about 225 µm, about 75 µm to about 200 µm, about 75 µm to about 175 µm, about 75 µm to about 150 µm, about 75 µm to about 125 µm, about 75 µm to about 100 µm, about 100 µm to about 375 µm, about 100 µm to about 350 µm, about 100 µm to about 325 µm, about 100 µm to about 300 µm, about 100 µm to about 275 µm, about 100 µm to about 250 µm, about 100 µm to about 225 µm, about 100 µm to about 200 µm, about 100 µm to about 175 µm, about 100 µm to about 150 µm, about 100 µm to about 125 µm, about 125 µm to about 375 µm, about 125 µm to about 350 µm, about 125 µm to about 325 µm, about 125 µm to about 300 µm, about 125 µm to about 275 µm, about 125 µm to about 250 µm, about 125 µm to about 225 µm, about 125 µm to about 200 µm, about 125 µm to about 175 µm, about 125 µm to about 150 µm, about 150 µm to about 375 µm, about 150 µm to about 350 µm, about 150 µm to about 325 µm, about 150 µm to about 300 µm, about 150 µm to about 275 µm, about 150 µm to about 250 µm, about 150 µm to about 225 µm, about 150 µm to about 200 µm, about 150 µm to about 175 µm, about 175 µm to about 375 µm, about 175 µm to about 350 µm, about 175 µm to about 325 µm, about 175 µm to about 300 µm, about 175 µm to about 275 µm, about 175 µm to about 250 µm, about 175 µm to about 225 µm, about 175 µm to about 200 µm, about 200 µm to about 375 µm, about 200 µm to about 350 µm, about 200 µm to about 325 µm, about 200 µm to about 300 µm, about 200 µm to about 275 µm, about 200 µm to about 250 µm, about 200 µm to about 225 µm, about 225 µm to about 375 µm, about 225 µm to about 350 µm, about 225 µm to about 325 µm, about 225 µm to about 300 µm, about 225 µm to about 275 µm, about 225 µm to about 250 µm, about 250 µm to about 375 µm, about 250 µm to about 350 µm, about 250 µm to about 325 µm, about 250 µm to about 300 µm, about 250 µm to about 275 µm, about 275 µm to about 375 µm, about 275 µm to about 350 µm, about 275 µm to about 325 µm, about 275 µm to about 300 µm, about 300 µm to about 375 µm, about 300 µm to about 350 µm, about 300 µm to about 325 µm, about 325 µm to about 375 µm, about 325 µm to about 350 µm, or about 350 µm to about 375 µm. In certain embodiments, the particles have a particle size distribution which is defined by a d(0.5) of from about 10 µm to about 400 µm.

In certain embodiments, the particles have a particle size distribution which is defined by a d(0.9) of about 10 µm to about 800 µm, about 50 µm to about 800 µm, about 100 µm to about 800 µm, about 150 µm to about 800 µm, about 200 µm to about 800 µm, about 250 µm to about 800 µm, about 300 µm to about 800 µm, about 350 µm to about 800 µm, about 400 µm to about 800 µm, about 450 µm to about 800 µm, about 500 µm to about 800 µm, about 550 µm to about 800 µm, about 600 µm to about 800 µm, about 650 µm to about 800 µm, about 700 µm to about 800 µm, about 750 µm to about 800 µm, about 150 µm to about 750 µm, about 150 µm to about 700 µm, about 150 µm to about 650 µm, about 150 µm to about 600 µm, about 150 µm to about 550 µm, about 150 µm to about 500 µm, about 150 µm to about 450 µm, about 150 µm to about 400 µm, about 150 µm to about 350 µm, about 150 µm to about 300 µm, about 150 µm to about 250 µm, about 150 µm to about 200 µm, about 200 µm to about 750 µm, about 200 µm to about 700 µm, about 200 µm to about 650 µm, about 200 µm to about 600 µm, about 200 µm to about 550 µm, about 200 µm to about 500 µm, about 200 µm to about 450 µm, about 200 µm to about 400 µm, about 200 µm to about 350 µm, about 200 µm to about 300 µm, about 200 µm to about 250 µm, about 250 µm to about 750 µm, about 250 µm to about 700 µm, about 250 µm to about 650 µm, about 250 µm to about 600 µm, about 250 µm to about 550 µm, about 250 µm to about 500 µm, about 250 µm to about 450 µm, about 250 µm to about 400 µm, about 250 µm to about 350 µm, about 250 µm to about 300 µm, about 300 µm to about 750 µm, about 300 µm to about 700 µm, about 300 µm to about 650 µm, about 300 µm to about 600 µm, about 300 µm to about 550 µm, about 300 µm to about 500 µm, about 300 µm to about 450 µm, about 300 µm to about 400 µm, about 300 µm to about 350 µm, about 350 µm to about 750 µm, about 350 µm to about 700 µm, about 350 µm to about 650 µm, about 350 µm to about 600 µm, about 350 µm to about 550 µm, about 350 µm to about 500 µm, about 350 µm to about 450 µm, about 350 µm to about 400 µm, about 400 µm to about 750 µm, about 400 µm to about 700 µm, about 400 µm to about 650 µm, about 400 µm to about 600 µm, about 400 µm to about 550 µm, about 400 µm to about 500 µm, about 400 µm to about 450 µm, about 450 µm to about 750 µm, about 450 µm to about 700 µm, about 450 µm to about 650 µm, about 450 µm to about 600 µm, about 450 µm to about 550 µm, about 450 µm to about 500 µm, about 500 µm to about 750 µm, about 500 µm to about 700 µm, about 500 µm to about 650 µm, about 500 µm to about 600 µm, about 500 µm to about 550 µm, about 550 µm to about 750 µm, about 550 µm to about 700 µm, about 550 µm to about 650 µm, about 550 µm to about 600 µm, about 600 µm to about 750 µm, about 600 µm to about 700 µm, about 600 µm to about 650 µm, about 650 µm to about 750 µm, about 650 µm to about 700 µm, or about 700 µm to about 750 µm. In certain embodiments, the particles have a particle size distribution which is defined by a d(0.9) of about 10 µm to about 800 µm, preferably below 500 µm.

In various embodiments, the invention provides a pharmaceutical material comprising particles of a crystalline hydrochloride salt of the compound of formula (I-A)

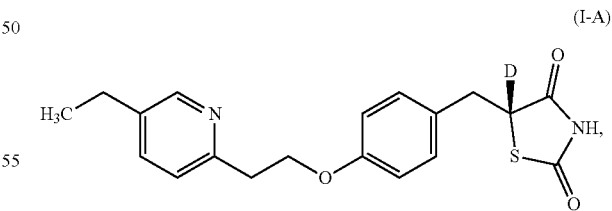

wherein the particles have a particle size distribution which is defined by a d(0.9) of from about 10 µm to about 800 µm preferably below 500 µm.

In certain embodiments, the particles in the composition have a needle-like crystal shape.

In certain embodiments, the total deuterium abundance in the compound of formula (I-A) is about 0.3 to about 2, about 0.4 to about 2, about 0.6 to about 2, about 0.8 to about 2, about 1 to about 2, about 1.2 to about 2, about 1.4 to about 2, about 1.6 to about 2, about 1.8 to about 2, about 0.3 to about 1.8, about 0.3 to about 1.6, about 0.3 to about 1.4, about 0.3 to about 1.2, about 0.3 to about 1, about 0.3 to about 0.8, about 0.3 to about 0.6, about 0.3 to about 0.4, about 0.4 to about 1.8, about 0.4 to about 1.6, about 0.4 to about 1.4, about 0.4 to about 1.2, about 0.4 to about 1, about 0.4 to about 0.8, about 0.4 to about 0.6, about 0.6 to about 1.8, about 0.6 to about 1.6, about 0.6 to about 1.4, about 0.6 to about 1.2, about 0.6 to about 1, about 0.6 to about 0.8, about 0.8 to about 1.8, about 0.8 to about 1.6, about 0.8 to about 1.4, about 0.8 to about 1.2, about 0.8 to about 1.0, about 1 to about 1.8, about 1 to about 1.6, about 1 to about 1.4, about 1 to about 1.2, about 1.2 to about 1.8, about 1.2 to about 1.6, about 1.2 to about 1.4, about 1.4 to about 1.8, about 1.4 to about 1.6, or about 1.6 to about 1.8.

Pharmaceutical Compositions

In one aspect, the invention provides pharmaceutical compositions comprising a pharmaceutically acceptable salt of the compound of formula I or formula I-A as described herein, including any of the pharmaceutical materials, and a pharmaceutically acceptable excipient, for the treatment of a condition, disease or disorder described herein (e.g., a neurological disorder, a cancer, a respiratory disorder, a metabolic disorder, a hepatitis, a cardiovascular disease, an inflammatory or immune-mediated disorder, a dermatological disorder, a wound, a skin defect, etc.). In certain embodiments, the pharmaceutically acceptable salt form of the compound of formula I or formula I-A is a deuterium chloride salt. In certain embodiments, the pharmaceutically acceptable salt form of the compound of formula I or formula I-A is a hydrochloride salt.

In various embodiments, a pharmaceutical composition comprises a deuterium chloride salt of the compound of formula I and a pharmaceutically acceptable excipient. In certain embodiments, the deuterium chloride salt of the compound of formula I is a crystalline deuterium chloride salt.

In various embodiments, a pharmaceutical composition comprises a crystalline deuterium chloride salt of the compound of formula I and a pharmaceutically acceptable excipient.

In various embodiments, a pharmaceutical composition comprises a hydrochloride salt of the compound of formula I-A and a pharmaceutically acceptable excipient. In certain embodiments, the hydrochloride salt of the compound of formula I-A is a crystalline hydrochloride salt.

In various embodiments, a pharmaceutical composition comprises a crystalline hydrochloride salt of the compound of formula I-A and a pharmaceutically acceptable excipient.

In various embodiments, the invention provides a pharmaceutical composition comprising (i) particles of a crystalline deuterium chloride salt of a deuterium-enriched compound of formula (I)

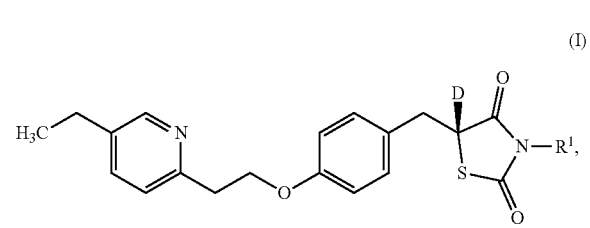

and (ii) a pharmaceutically acceptable excipient, wherein $R^1$ is H or D, provided that the abundance of deuterium in $R^1$ is at least 80%, and wherein the particles in the composition have a crystal shape selected from hexagonal, rod, and combinations thereof.

In various embodiments, the invention provides a pharmaceutical composition comprising (i) particles of a crystalline deuterium chloride salt of a deuterium-enriched compound of formula (I)

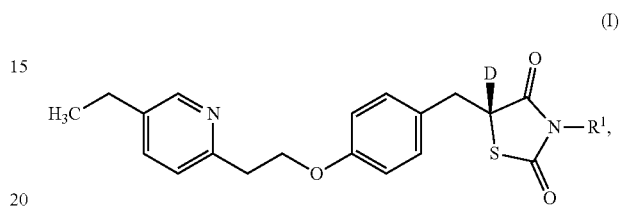

and (ii) a pharmaceutically acceptable excipient, wherein $R^1$ is H or D, provided that the abundance of deuterium in $R^1$ is at least 80%, and wherein the particles have a particle size distribution which is defined by a d(0.9) of about 10 μm to about 800 μm preferably below 500 μm.

In various embodiments, the invention provides a pharmaceutical composition comprising (i) particles of a crystalline hydrochloride salt of the compound of formula (I-A)

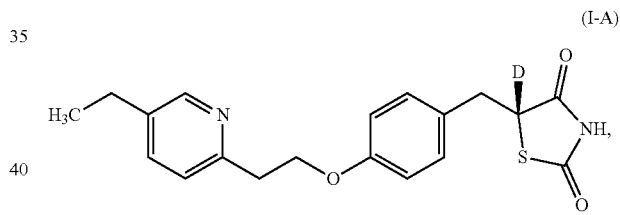

and (ii) a pharmaceutically acceptable excipient, wherein the particles in the pharmaceutical composition have a needle-like crystal shape.

In various embodiments, the invention provides a pharmaceutical composition comprising (i) particles of a crystalline hydrochloride salt of the compound of formula (I-A)

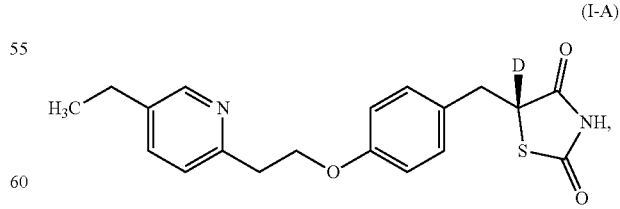

and (ii) a pharmaceutically acceptable excipient, wherein the particles have a particle size distribution which is defined by a d(0.9) of from about 10 μm to 800 μm preferably below 500 μm.

In certain embodiments, the pharmaceutical compositions described herein comprise a therapeutically effective amount of a pharmaceutically acceptable salt of the compound of formula I or formula I-A. In certain embodiments, the pharmaceutical compositions described herein comprise a therapeutically effective amount of a deuterium chloride salt of the compound of formula I. In certain embodiments, the pharmaceutical compositions described herein comprise a therapeutically effective amount of a crystalline deuterium chloride salt of the compound of formula I. In certain embodiments, the pharmaceutical compositions described herein comprise a therapeutically effective amount of a hydrochloride salt of the compound of formula I-A. In certain embodiments, the pharmaceutical compositions described herein comprise a therapeutically effective amount of a crystalline hydrochloride salt of the compound of formula I-A.

In certain embodiments, the crystalline deuterium chloride salt of the compound of formula I is a crystalline deuterium chloride salt as described herein.

In certain embodiments, the crystalline hydrochloride salt of the compound of formula I-A is a crystalline hydrochloride salt as described herein.

The pharmaceutical compositions provided herein can be administered by a variety of routes including, but not limited to, oral (enteral) administration, parenteral (by injection) administration, rectal administration, transdermal administration, intradermal administration, intrathecal administration, subcutaneous (SC) administration, intravenous (IV) administration, intramuscular (IM) administration, and intranasal administration. In some embodiments, the pharmaceutical compositions disclosed herein are administered orally.

The pharmaceutical compositions provided herein may also be administered chronically ("chronic administration"). Chronic administration refers to administration of a compound or pharmaceutical composition thereof over an extended period of time, e.g., for example, over 3 months, 6 months, 1 year, 2 years, 3 years, 5 years, etc., or may be continued indefinitely, for example, for the rest of the subject's life. In certain embodiments, the chronic administration is intended to provide a constant level of the compound in the blood, e.g., within the therapeutic window over the extended period of time.

The pharmaceutical compositions provided herein may be presented in unit dosage forms to facilitate accurate dosing. The term "unit dosage forms" refers to physically discrete units suitable as unitary dosages for human subjects and other mammals, each unit containing a predetermined quantity of active material calculated to produce the desired therapeutic effect, in association with a suitable pharmaceutical excipient. Typical unit dosage forms include prefilled, premeasured ampules or syringes of the liquid compositions or pills, tablets, capsules or the like in the case of solid compositions.

Although the descriptions of pharmaceutical compositions provided herein are principally directed to pharmaceutical compositions which are suitable for administration to humans, it will be understood by the skilled artisan that such compositions are generally suitable for administration to animals of all sorts. Modification of pharmaceutical compositions suitable for administration to humans in order to render the compositions suitable for administration to various animals is well understood, and the ordinarily skilled veterinary pharmacologist can design and/or perform such modification with ordinary experimentation. General considerations in the formulation and/or manufacture of pharmaceutical compositions can be found, for example, in Remington: The Science and Practice of Pharmacy 21$^{st}$ ed., Lippincott Williams & Wilkins, 2005.

Formulations

Pharmaceutical compositions can be used in the preparation of individual, single unit dosage forms. Pharmaceutical compositions and dosage forms provided herein comprise a compound provided herein, or a pharmaceutically acceptable salt, solvate, or enantiomer thereof. Pharmaceutical compositions and dosage forms can further comprise one or more excipients.

Pharmaceutical compositions and dosage forms provided herein can comprise one or more additional active ingredients. Examples of optional second, or additional, active ingredients are described above.

Single unit dosage forms provided herein are suitable for oral, mucosal (e.g., nasal, sublingual, vaginal, buccal, or rectal), parenteral (e.g., subcutaneous, intravenous, bolus injection, intramuscular, or intraarterial), topical (e.g., eye drops or other ophthalmic preparations), transdermal or transcutaneous administration to a patient. Examples of dosage forms include, but are not limited to: tablets; caplets; capsules, such as soft elastic gelatin capsules; cachets; troches; lozenges; dispersions; suppositories; powders; aerosols (e.g., nasal sprays or inhalers); gels; liquid dosage forms suitable for oral or mucosal administration to a patient, including suspensions (e.g., aqueous or non-aqueous liquid suspensions, oil-in-water emulsions, or a water-in-oil liquid emulsions), solutions, and elixirs; liquid dosage forms suitable for parenteral administration to a patient; eye drops or other ophthalmic preparations suitable for topical administration; and sterile solids (e.g., crystalline or amorphous solids) that can be reconstituted to provide liquid dosage forms suitable for parenteral administration to a patient.

The composition, shape, and type of dosage forms will typically vary depending on their use. For example, a dosage form used in the acute treatment of a disease may contain larger amounts of one or more of the active ingredients it comprises than a dosage form used in the chronic treatment of the same disease. Similarly, a parenteral dosage form may contain smaller amounts of one or more of the active ingredients it comprises than an oral dosage form used to treat the same disease. These and other ways in which specific dosage forms used will vary from one another will be readily apparent to those skilled in the art. See, e.g., Remington's Pharmaceutical Sciences, 18th ed., Mack Publishing, Easton Pa. (1990).

In another aspect of the invention, the pharmaceutical compositions and dosage forms comprise one or more excipients. Suitable excipients are well known to those skilled in the art of pharmacy, and non-limiting examples of suitable excipients are provided herein. Whether a particular excipient is suitable for incorporation into a pharmaceutical composition or dosage form depends on a variety of factors well known in the art including, but not limited to, the way in which the dosage form will be administered to a patient. For example, oral dosage forms such as tablets may contain excipients not suited for use in parenteral dosage forms. The suitability of a particular excipient may also depend on the specific active ingredients in the dosage form. For example, the decomposition of some active ingredients may be accelerated by some excipients, or when exposed to water. Active ingredients that comprise primary or secondary amines are particularly susceptible to such accelerated decomposition. Consequently, provided are pharmaceutical compositions and dosage forms that contain little, if any, lactose other mono- or di-saccharides. As used herein, the term "lactose-free" means that the amount of lactose present, if any, is insufficient to substantially increase the degradation rate of an active ingredient.

Lactose-free compositions can comprise excipients that are well known in the art and are listed, for example, in the U.S. Pharmacopeia (USP) 25-NF20 (2002). In general, lactose-free compositions comprise active ingredients, a binder/filler, and a lubricant in pharmaceutically compatible and pharmaceutically acceptable amounts. In another aspect, lactose-free dosage forms comprise active ingredients, microcrystalline cellulose, pre-gelatinized starch, and magnesium stearate.

Also provided are anhydrous pharmaceutical compositions and dosage forms comprising active ingredients, since water can facilitate the degradation of some compounds. For example, the addition of water (e.g., 5%) is widely accepted in the pharmaceutical arts as a means of simulating long-term storage in order to determine characteristics such as shelf-life or the stability of formulations over time. See, e.g., Jens T. Carstensen, Drug Stability: Principles & Practice, 2d. Ed., Marcel Dekker, NY, NY, 1995, pp. 379-80. In effect, water and heat accelerate the decomposition of some compounds. Thus, the effect of water on a formulation can be of great significance since moisture and/or humidity are commonly encountered during manufacture, handling, packaging, storage, shipment, and use of formulations.

Anhydrous pharmaceutical compositions and dosage forms can be prepared using anhydrous or low moisture containing ingredients and low moisture or low humidity conditions. Pharmaceutical compositions and dosage forms that comprise lactose and at least one active ingredient that comprises a primary or secondary amine are preferably anhydrous if substantial contact with moisture and/or humidity during manufacturing, packaging, and/or storage is expected.

An anhydrous pharmaceutical composition should be prepared and stored such that its anhydrous nature is maintained. Accordingly, anhydrous compositions are, in another aspect, packaged using materials known to prevent exposure to water such that they can be included in suitable formulary kits. Examples of suitable packaging include, but are not limited to, hermetically sealed foils, plastics, dose containers (e.g., vials), blister packs, and strip packs.

Also provided are pharmaceutical compositions and dosage forms that comprise one or more compounds that reduce the rate by which an active ingredient will decompose. Such compounds, which are referred to herein as "stabilizers," include, but are not limited to, antioxidants such as ascorbic acid, pH buffers, or salt buffers.

Like the amounts and types of excipients, the amounts and specific types of active ingredients in a dosage form may differ depending on factors such as, but not limited to, the route by which it is to be administered to patients. In another aspect, dosage forms comprise a compound provided herein in an amount of from about 0.10 to about 500 mg. Examples of dosages include, but are not limited to, 0.1, 1, 2, 5, 7.5, 10, 12.5, 15, 17.5, 20, 25, 50, 100, 150, 200, 250, 300, 350, 400, 450, or 500 mg.

In another aspect, dosage forms comprise the second active ingredient in an amount of 1-about 1000 mg, from about 5 to about 500 mg, from about 10 to about 350 mg, or from about 50 to about 200 mg. Of course, the specific amount of the second active agent will depend on the specific agent used, the diseases or disorders being treated or managed, and the amount(s) of a compound provided herein, and any optional additional active agents concurrently administered to the patient.

Pharmaceutical compositions that are suitable for oral administration can be provided as discrete dosage forms, such as, but not limited to, tablets (e.g., chewable tablets), caplets, capsules, and liquids (e.g., flavored syrups). Such dosage forms contain predetermined amounts of active ingredients, and may be prepared by methods of pharmacy well known to those skilled in the art. See generally, Remington's Pharmaceutical Sciences, 18th ed., Mack Publishing, Easton Pa. (1990).

Oral dosage forms provided herein are prepared by combining the active ingredients in an intimate admixture with at least one excipient according to conventional pharmaceutical compounding techniques. Excipients can take a wide variety of forms depending on the form of preparation desired for administration. For example, excipients suitable for use in oral liquid or aerosol dosage forms include, but are not limited to, water, glycols, oils, alcohols, flavoring agents, preservatives, and coloring agents. Examples of excipients suitable for use in solid oral dosage forms (e.g., powders, tablets, capsules, and caplets) include, but are not limited to, starches, sugars, micro-crystalline cellulose, diluents, granulating agents, lubricants, binders, and disintegrating agents.

In another aspect, the invention provides oral dosage forms that are tablets or capsules, in which case solid excipients are employed. In another aspect, the tablets can be coated by standard aqueous or nonaqueous techniques. Such dosage forms can be prepared by any of the methods of pharmacy. In general, pharmaceutical compositions and dosage forms are prepared by uniformly and intimately admixing the active ingredients with liquid carriers, finely divided solid carriers, or both, and then shaping the product into the desired presentation if necessary.

For example, a tablet can be prepared by compression or molding. Compressed tablets can be prepared by compressing in a suitable machine the active ingredients in a free-flowing form such as powder or granules, optionally mixed with an excipient. Molded tablets can be made by molding in a suitable machine a mixture of the powdered compound moistened with an inert liquid diluent.

Examples of excipients that can be used in oral dosage forms provided herein include, but are not limited to, binders, fillers, disintegrants, and lubricants. Binders suitable for use in pharmaceutical compositions and dosage forms include, but are not limited to, corn starch, potato starch, or other starches, gelatin, natural and synthetic gums such as acacia, sodium alginate, alginic acid, other alginates, powdered tragacanth, guar gum, cellulose and its derivatives (e.g., ethyl cellulose, cellulose acetate, carboxymethyl cellulose calcium, sodium carboxymethyl cellulose), polyvinyl pyrrolidone, methyl cellulose, pre-gelatinized starch, hydroxypropyl methyl cellulose, (e.g., Nos. 2208, 2906, 2910), microcrystalline cellulose, and mixtures thereof.

Suitable forms of microcrystalline cellulose include, but are not limited to, the materials sold as AVICEL-PH-101, AVICEL-PH-103 AVICEL RC-581, AVICEL-PH-105 (available from FMC Corporation, American Viscose Division, Avicel Sales, Marcus Hook, Pa.), and mixtures thereof. A specific binder is a mixture of microcrystalline cellulose and sodium carboxymethyl cellulose sold as AVICEL RC-581. Suitable anhydrous or low moisture excipients or additives include AVICEL-PH-103™ and Starch 1500 LM.

Examples of fillers suitable for use in the pharmaceutical compositions and dosage forms provided herein include, but are not limited to, talc, calcium carbonate (e.g., granules or powder), microcrystalline cellulose, powdered cellulose, dextrates, kaolin, mannitol, silicic acid, sorbitol, starch, pre-gelatinized starch, and mixtures thereof. The binder or filler in pharmaceutical compositions is, in another aspect, present in from about 50 to about 99 weight percent of the pharmaceutical composition or dosage form.

Disintegrants may be used in the compositions to provide tablets that disintegrate when exposed to an aqueous environment. Tablets that contain too much disintegrant may disintegrate in storage, while those that contain too little may not disintegrate at a desired rate or under the desired conditions. Thus, a sufficient amount of disintegrant that is neither too much nor too little to detrimentally alter the release of the active ingredients may be used to form solid oral dosage forms. The amount of disintegrant used varies based upon the type of formulation, and is readily discernible to those of ordinary skill in the art. In another aspect, pharmaceutical compositions comprise from about 0.5 to about 15 weight percent of disintegrant, or from about 1-about 5 weight percent of disintegrant.

Disintegrants that can be used in pharmaceutical compositions and dosage forms include, but are not limited to, agar-agar, alginic acid, calcium carbonate, microcrystalline cellulose, croscarmellose sodium, crospovidone, polacrilin potassium, sodium starch glycolate, potato or tapioca starch, other starches, pre-gelatinized starch, other starches, clays, other algins, other celluloses, gums, and mixtures thereof.

Lubricants that can be used in pharmaceutical compositions and dosage forms include, but are not limited to, calcium stearate, magnesium stearate, mineral oil, light mineral oil, glycerin, sorbitol, mannitol, polyethylene glycol, other glycols, stearic acid, sodium lauryl sulfate, talc, hydrogenated vegetable oil (e.g., peanut oil, cottonseed oil, sunflower oil, sesame oil, olive oil, corn oil, and soybean oil), zinc stearate, ethyl oleate, ethyl laureate, agar, and mixtures thereof. Additional lubricants include, for example, a Syloid® silica gel (AEROSIL200, manufactured by W.R. Grace Co. of Baltimore, Md.), a coagulated aerosol of synthetic silica (marketed by Degussa Co. of Piano, TX), CAB-O-SIL (a pyrogenic silicon dioxide product sold by Cabot Co. of Boston, Mass.), and mixtures thereof. If used at all, lubricants may be used in an amount of less than about 2 weight percent of the pharmaceutical compositions or dosage forms into which they are incorporated.

In another aspect, the invention provides a solid oral dosage form comprising a compound provided herein, anhydrous lactose, microcrystalline cellulose, polyvinylpyrrolidone, stearic acid, colloidal anhydrous silica, and gelatin.

Active ingredients provided herein can also be administered by controlled release means or by delivery devices that are well known to those of ordinary skill in the art. Examples include, but are not limited to, those described in U.S. Pat. Nos. 3,845,770; 3,916,899; 3,536,809; 3,598,123; and 4,008,719, 5,674,533, 5,059,595, 5,591,767, 5,120,548, 5,073,543, 5,639,476, 5,354,556, and 5,733,566, each of which is incorporated in its entirety herein by reference. Such dosage forms can be used to provide slow or controlled-release of one or more active ingredients using, for example, hydropropylmethyl cellulose, other polymer matrices, gels, permeable membranes, osmotic systems, multilayer coatings, microparticles, liposomes, microspheres, or a combination thereof to provide the desired release profile in varying proportions. Suitable controlled-release formulations known to those of ordinary skill in the art, including those described herein, can be readily selected for use with the active agents provided herein. In another aspect, the invention procies single unit dosage forms suitable for oral administration such as, but not limited to, tablets, capsules, gelcaps, and caplets that are adapted for controlled-release.

Controlled-release pharmaceutical products improve drug therapy over that achieved by their non-controlled counterparts. In another aspect, the invention provides the use of a controlled-release preparation in medical treatment is characterized by a minimum of drug substance being employed to cure or control the condition in a minimum amount of time. Advantages of controlled-release formulations include extended activity of the drug, reduced dosage frequency, and increased patient compliance. In addition, controlled-release formulations can be used to affect the time of onset of action or other characteristics, such as blood levels of the drug, and can thus affect the occurrence of side (e.g., adverse) effects.

In another aspect, the controlled-release formulations are designed to initially release an amount of drug (active ingredient) that promptly produces the desired therapeutic or prophylactic effect, and gradually and continually release of other amounts of drug to maintain this level of therapeutic or prophylactic effect over an extended period of time. In another aspect, in order to maintain a constant level of drug in the body, the drug can be released from the dosage form at a rate that will replace the amount of drug being metabolized and excreted from the body. Controlle release of an active ingredient can be stimulated by various conditions including, but not limited to, pH, temperature, enzymes, water, or other physiological conditions or compounds.

Parenteral dosage forms can be administered to patients by various routes including, but not limited to, subcutaneous, intravenous (including bolus injection), intramuscular, and intraarterial. Administration of a parenteral dosage form bypasses patients' natural defenses against contaminants, and thus, in these aspects, parenteral dosage forms are sterile or capable of being sterilized prior to administration to a patient. Examples of parenteral dosage forms include, but are not limited to, solutions ready for injection, dry products ready to be dissolved or suspended in a pharmaceutically acceptable vehicle for injection, suspensions ready for injection, and emulsions.

Suitable vehicles that can be used to provide parenteral dosage forms are well known to those skilled in the art. Examples include, but are not limited to: Water for Injection USP; aqueous vehicles such as, but not limited to, Sodium Chloride Injection, Ringer's Injection, Dextrose Injection, Dextrose and Sodium Chloride Injection, and Lactated Ringer's Injection; water-miscible vehicles such as, but not limited to, ethyl alcohol, polyethylene glycol, and polypropylene glycol; and nonaqueous vehicles such as, but not limited to, corn oil, cottonseed oil, peanut oil, sesame oil, ethyl oleate, isopropyl myristate, and benzyl benzoate.

Compounds that increase the solubility of one or more of the active ingredients disclosed herein can also be incorporated into the parenteral dosage forms. For example, cyclodextrin and its derivatives can be used to increase the solubility of a compound provided herein. See, e.g., U.S. Pat. No. 5,134,127, which is incorporated in its entirety herein by reference.

Topical and mucosal dosage forms provided herein include, but are not limited to, sprays, aerosols, solutions, emulsions, suspensions, eye drops or other ophthalmic preparations, or other forms known to one of skill in the art. See, e.g., Remington's Pharmaceutical Sciences, 16th and 18th eds., Mack Publishing, Easton Pa. (1980 & 1990); and Introduction to Pharmaceutical Dosage Forms, 4th ed., Lea & Febiger, Philadelphia (1985). Dosage forms suitable for treating mucosal tissues within the oral cavity can be formulated as mouthwashes or as oral gels.

Suitable excipients (e.g., carriers and diluents) and other materials that can be used to provide topical and mucosal dosage forms encompassed herein are well known to those skilled in the pharmaceutical arts, and depend on the particular tissue to which a given pharmaceutical composition or dosage form will be applied. In another aspect, excipients include, but are not limited to, water, acetone, ethanol, ethylene glycol, propylene glycol, butane-1,3-diol, isopropyl myristate, isopropyl palmitate, mineral oil, and mixtures thereof to form solutions, emulsions or gels, which are nontoxic and pharmaceutically acceptable. Moisturizers or humectants can also be added to pharmaceutical compositions and dosage forms. Examples of additional ingredients are well known in the art. See, e.g., Remington's Pharmaceutical Sciences, 16th and 18th eds., Mack Publishing, Easton Pa. (1980 & 1990).

The pH of a pharmaceutical composition or dosage form may also be adjusted to improve delivery of one or more active ingredients. Also, the polarity of a solvent carrier, its ionic strength, or tonicity can be adjusted to improve delivery. Compounds such as stearates can also be added to pharmaceutical compositions or dosage forms to alter the hydrophilicity or lipophilicity of one or more active ingredients so as to improve delivery. In other aspects, stearates can serve as a lipid vehicle for the formulation, as an emulsifying agent or surfactant, or as a delivery-enhancing or penetration-enhancing agent. In other aspects, salts, solvates, prodrugs, or enantiomers of the active ingredients can be used to further adjust the properties of the resulting composition.

In another aspect, the active ingredients provided herein are not administered to a patient at the same time or by the same route of administration. In another aspect, provided are kits which can simplify the administration of appropriate amounts of active ingredients.

In another aspect, the invention provides a kit comprising a dosage form of a compound provided herein. Kits can further comprise additional active ingredients.

In other aspects, the kits can further comprise devices that are used to administer the active ingredients. Examples of such devices include, but are not limited to, syringes, drip bags, patches, and inhalers.

Kits can further comprise cells or blood for transplantation as well as pharmaceutically acceptable vehicles that can be used to administer one or more active ingredients. For example, if an active ingredient is provided in a solid form that must be reconstituted for parenteral administration, the kit can comprise a sealed container of a suitable vehicle in which the active ingredient can be dissolved to form a particulate-free sterile solution that is suitable for parenteral administration. Examples of pharmaceutically acceptable vehicles include, but are not limited to: Water for Injection USP; aqueous vehicles such as, but not limited to, Sodium Chloride Injection, Ringer's Injection, Dextrose Injection, Dextrose and Sodium Chloride Injection, and Lactated Ringer's Injection; water-miscible vehicles such as, but not limited to, ethyl alcohol, polyethylene glycol, and polypropylene glycol; and non-aqueous vehicles such as, but not limited to, corn oil, cottonseed oil, peanut oil, sesame oil, ethyl oleate, isopropyl myristate, and benzyl benzoate.

In an aspect, provided is a pharmaceutical composition comprising a hydrogen chloride salt or deuterium chloride salt of deuterium-enriched pioglitazone as described herein, lactose, a carmellose, a hyprolose, and a stearate salt.

Methods of Use and Treatment

Provided herein are methods of treating a condition, disease, or disorder (e.g., a neurological disorder, a cancer, a respiratory disorder, an endocrine disorder, a metabolic disorder, a renal disorder, a hepatitis, a cardiovascular disease, an inflammatory or immune-mediated disorder, a dermatological disorder, a wound, a skin defect, etc.), the method comprising administering to a patient in need thereof a therapeutically effective amount of a pharmaceutically acceptable salt of a compound of formula I or formula I-A, e.g., the compound of formula I or formula I-A as a deuterium chloride salt or a hydrochloride salt described herein, to treat the condition, disease, or disorder. In various embodiments, the method comprises administering to a patient in need thereof a therapeutically effective amount of a deuterium chloride salt of the compound of formula I, e.g., a crystalline deuterium chloride salt form as described herein, to treat the condition, disease, or disorder. In various embodiments, the method comprises administering to a patient in need thereof a therapeutically effective amount of a hydrochloride salt of the compound of formula I-A, e.g., a crystalline hydrochloride salt form described herein, to treat condition, disease, or disorder.

In certain embodiments, the condition, disease, or disorder is a neurological disorder. In certain embodiments, the condition, disease, or disorder is a cancer. In certain embodiments, the condition, disease, or disorder is a respiratory disorder. In certain embodiments, the condition, disease, or disorder is an endocrine or metabolic disorder. In certain embodiments, the condition, disease, or disorder is a metabolic disorder. In certain embodiments, the condition, disease, or disorder is a hepatitis. In certain embodiments, the condition, disease, or disorder is a cardiovascular disease. In certain embodiments, the condition, disease, or disorder is a renal disease. In certain embodiments, the condition, disease, or disorder is an inflammatory or immune-mediated disorder. In certain embodiments, the condition, disease, or disorder is a dermatological disorder. In certain embodiments, the condition, disease, or disorder is a wound. In certain embodiments, the condition, disease, or disorder is a skin defect.

Also provided herein are methods of modulating the amount and/or function of an endogenous biological molecule (e.g., a triglyceride, a fatty acid, a carbohydrate or sugar, a low-density lipoprotein, a high-density lipoprotein, a cytokine, etc.) for the prevention or treatment of a condition, disease, or disorder described herein, the method comprising administering to a patient in need thereof a therapeutically effective amount of a pharmaceutically acceptable salt of a compound of formula I or formula I-A, e.g., the compound of formula I or formula I-A as a deuterium chloride salt or a hydrochloride salt described herein, to modulate the endogenous biological molecule. In various embodiments, the method comprises administering to a patient in need thereof a therapeutically effective amount of a deuterium chloride salt of the compound of formula I, e.g., a crystalline deuterium chloride salt form as described herein, to modulate the endogenous biological molecule. In various embodiments, the method comprises administering to a patient in need thereof a therapeutically effective amount of a hydrochloride salt of the compound of formula I-A, e.g., a crystalline hydrochloride salt form described herein, to modulate the endogenous biological molecule.

In certain embodiments, the endogenous biological molecule is a triglyceride. In certain embodiments, the endogenous biological molecule is a fatty acid. In certain embodiments, the endogenous biological molecule is a carbohydrate or sugar. In certain embodiments, the endogenous biological molecule is a low-density lipoprotein. In certain embodiments, the endogenous biological molecule is a high-density lipoprotein. In certain embodiments, the endogenous biological molecule is a cytokine.

(i) Treating Metabolic Disorders

Another aspect of the invention provides a method of treating a metabolic disorder or hepatic disorder selected from the group consisting of nonalcoholic fatty liver disease, nonalcoholic steatohepatitis, viral hepatitis, liver cirrhosis, liver fibrosis, diabetic retinopathy, diabetic neuropathy, diabetic nephropathy, beta cell depletion insulin resistance in a patient with congenital adrenal hyperplasia treated with a glucocorticoid, polycystic ovary syndrome, leukodystrophies including adrenoleukodystrophy and adrenomyeloneuropathy, dysmetabolism in peritoneal dialysis patients, reduced insulin secretion, improper distribution of brown fat cells and white fat cells, obesity, or improper modulation of leptin levels. The method comprises administering to a patient in need thereof a therapeutically effective amount of a pharmaceutically acceptable salt of a compound of formula I or formula I-A, e.g., the compound of formula I or formula I-A as a deuterium chloride salt or a hydrochloride salt described herein, to treat the metabolic disorder. In certain embodiments, the method comprises administering to a patient in need thereof a therapeutically effective amount of a deuterium chloride salt of the compound of formula I, e.g., a crystalline deuterium chloride salt form as described herein, to treat the metabolic disorder. In certain embodiments, the method comprises administering to a patient in need thereof a therapeutically effective amount of a hydrochloride salt of the compound of formula I-A, e.g., a crystalline hydrochloride salt form described herein, to treat the metabolic disorder. In certain embodiments, the metabolic disorder is further selected from a complication of diabetes. In certain embodiments, the metabolic disorder is nonalcoholic fatty liver disease, diabetic retinopathy, diabetic neuropathy, diabetic nephropathy, or beta cell depletion insulin resistance in a patient with congenital adrenal hyperplasia treated with a glucocorticoid. In certain embodiments, the metabolic disorder is nonalcoholic fatty liver disease, diabetic retinopathy, diabetic neuropathy, diabetic nephropathy, beta cell depletion, reduced insulin secretion, improper distribution of brown fat cells and white fat cells, obesity, or improper modulation of leptin levels. In certain other embodiments, the metabolic disorder is non-alcoholic fatty liver disease. In certain other embodiments, the metabolic disorder is non-alcoholic steatohepatitis. In certain other embodiments, the metabolic disorder is Type II diabetes mellitus. In certain other embodiments, the metabolic disorder is beta cell loss treatable by B-cell regeneration. In certain other embodiments, the metabolic disorder is central obesity, dyslipidemia, or pre-diabetes. In certain other embodiments, the metabolic disorder is polycystic ovary syndrome. In certain other embodiments, the metabolic disorder is leukodystrophy including adrenoleukodystrophy and adrenomyeloneuropathy.

Nonalcoholic Fatty Liver Disease

In certain embodiments, a method is provided for treatment of nonalcoholic fatty liver disease, the method comprising administering to a patient in need thereof a therapeutically effective amount of a pharmaceutically acceptable salt of a compound of formula I or formula I-A, e.g., the compound of formula I or formula I-A as a deuterium chloride salt or a hydrochloride salt described herein, to treat the nonalcoholic fatty liver disease. The therapeutic methods are contemplated to provide particular benefits to patients suffering from nonalcoholic fatty liver disease. Exemplary benefits include little to no occurrence of PPAR gamma side effects (e.g., weight gain, edema, and/or bone loss) while achieving improvement in the patient's nonalcoholic fatty liver disease (which may include reduced amount of hepatic fat due to the therapy).

Nonalcoholic Steatohepatitis

In certain embodiments, a method is provided for treatment of nonalcoholic steatohepatitis, the method comprising administering to a patient in need thereof a therapeutically effective amount of a pharmaceutically acceptable salt of a compound of formula I or formula I-A, e.g., the compound of formula I or formula I-A as a deuterium chloride salt or a hydrochloride salt described herein, to treat the nonalcoholic steatohepatitis. The therapeutic methods are contemplated to provide particular benefits to patients suffering from nonalcoholic steatohepatitis. Exemplary benefits include little to no occurrence of PPAR gamma side effects (e.g., weight gain, edema, and/or bone loss) while achieving improvement in the patient's nonalcoholic steatohepatitis (which may include reduced amount of hepatic fat due to the therapy).

Type II Diabetes Mellitus

In certain embodiments, a method is provided for treatment of Type II diabetes mellitus, the method comprising administering to a patient in need thereof a therapeutically effective amount of a pharmaceutically acceptable salt of a compound of formula I or formula I-A, e.g., the compound of formula I or formula I-A as a deuterium chloride salt or a hydrochloride salt described herein, to treat the Type II diabetes mellitus. The therapeutic methods are contemplated to provide particular benefits to patients suffering from Type II diabetes mellitus. Exemplary benefits include little to no occurrence of PPAR gamma side effects (e.g., weight gain, edema, and/or bone loss) while achieving improvement in the patient's Type II diabetes mellitus (which may include improvement in the patient's glycemic control).

(ii) Treatment of Cancer

Another aspect of the invention provides a method of treating cancer. The method comprises administering to a patient in need thereof a therapeutically effective amount of a pharmaceutically acceptable salt of a compound of formula I or formula I-A, e.g., the compound of formula I or formula I-A as a deuterium chloride salt or a hydrochloride salt described herein, to treat the cancer. In certain embodiments, the method comprises administering to a patient in need thereof a therapeutically effective amount of a deuterium chloride salt of the compound of formula I, e.g., a crystalline deuterium chloride salt form as described herein, to treat the cancer. In certain embodiments, the method comprises administering to a patient in need thereof a therapeutically effective amount of a hydrochloride salt of the compound of formula I-A, e.g., a crystalline hydrochloride salt form described herein, to treat the cancer.

In certain embodiments, the cancer is lung cancer, hepatocellular carcinoma, astrocytoma, glioma, glioblastoma, meningioma, liver cancer, lymphoma, melanoma, multiple myeloma, pancreatic cancer, colorectal cancer, pituitary cancer, thyroid cancer, esophageal cancer, or prostate cancer. In certain embodiments, the cancer is non-small cell lung cancer or hepatocellular carcinoma.

In certain other embodiments, the cancer is lung cancer, hepatocellular carcinoma, astrocytoma, glioma, glioblastoma, meningioma, liver cancer, lymphoma, melanoma, multiple myeloma, pancreatic cancer, colorectal cancer, pituitary cancer, thyroid cancer, esophageal cancer, prostate cancer, nose cancer, throat cancer, kidney cancer, breast cancer, stomach cancer, or uterine cancer. In certain other embodiments, the cancer is brain cancer, bladder cancer, breast cancer, cervical cancer, colon cancer, colorectal cancer, endometrial cancer, esophageal cancer, leukemia, lung cancer, liver cancer, melanoma, ovarian cancer, pancreatic cancer, prostate cancer, rectal cancer, renal cancer, stomach cancer, testicular cancer, or uterine cancer. In yet other embodiments, the cancer is a vascularized tumor, squamous cell carcinoma, adenocarcinoma, small cell carcinoma, melanoma, glioma, neuroblastoma, sarcoma (e.g., an angiosarcoma or chondrosarcoma), larynx cancer, parotid cancer, biliary tract cancer, thyroid cancer, acral lentiginous melanoma, actinic keratosis, acute lymphocytic leukemia, acute myeloid leukemia, adenoid cystic carcinoma, adenoma, adenosarcoma, adenosquamous carcinoma, anal canal cancer, anal cancer, anorectal cancer, astrocytic tumor, Bartholin's gland carcinoma, basal cell carcinoma, biliary cancer, bone cancer, bone marrow cancer, bronchial cancer, bronchial gland carcinoma, carcinoid, cholangiocarcinoma, chorioid plexus papilloma/carcinoma, chronic lymphocytic leukemia, chronic myeloid leukemia, clear cell carcinoma, connective tissue cancer, cystadenoma, digestive system cancer, duodenum cancer, endocrine system cancer, endodermal sinus tumor, endometrial hyperplasia, endometrial stromal sarcoma, endometrioid adenocarcinoma, endothelial cell cancer, ependymal cancer, epithelial cell cancer, Ewing's sarcoma, eye and orbit cancer, female genital cancer, focal nodular hyperplasia, gallbladder cancer, gastric antrum cancer, gastric fundus cancer, gastrinoma, glioblastoma, glucagonoma, heart cancer, hemangioblastoma, hemangioendothelioma, hemangioma, hepatic adenoma, hepatic adenomatosis, hepatobiliary cancer, hepatocellular carcinoma, Hodgkin's disease, ileum cancer, insulinoma, intraepithelial neoplasia, interepithelial squamous cell neoplasia, intrahepatic bile duct cancer, invasive squamous cell carcinoma, jejunum cancer, joint cancer, Kaposi's sarcoma, pelvic cancer, large cell carcinoma, large intestine cancer, leiomyosarcoma, lentigo maligna melanoma, lymphoma, male genital cancer, malignant melanoma, malignant mesothelial tumor, medulloblastoma, medulloepithelioma, meningeal cancer, mesothelial cancer, metastatic carcinoma, mouth cancer, mucoepidermoid carcinoma, multiple myeloma, muscle cancer, nasal tract cancer, nervous system cancer, neuroepithelial adenocarcinoma, nodular melanoma, non-epithelial skin cancer, non-Hodgkin's lymphoma, oat cell carcinoma, oligodendroglial cancer, oral cavity cancer, osteosarcoma, papillary serous adenocarcinoma, penile cancer, pharynx cancer, pituitary tumor, plasmacytoma, pseudosarcoma, pulmonary blastoma, rectal cancer, renal cell carcinoma, respiratory system cancer, retinoblastoma, rhabdomyosarcoma, sarcoma, serous carcinoma, sinus cancer, skin cancer, small cell carcinoma, small intestine cancer, smooth muscle cancer, soft tissue cancer, somatostatin-secreting tumor, spine cancer, squamous cell carcinoma, striated muscle cancer, submesothelial cancer, superficial spreading melanoma, T-cell leukemia, tongue cancer, undifferentiated carcinoma, ureter cancer, urethral cancer, urinary bladder cancer, urinary system cancer, uterine cervix cancer, uterine corpus cancer, uveal melanoma, vaginal cancer, verrucous carcinoma, VIPoma, vulva cancer, well differentiated carcinoma, or Wilms tumor.

In certain other embodiments, the cancer is non-Hodgkin's lymphoma, such as a B-cell lymphoma or a T-cell lymphoma. In certain embodiments, the non-Hodgkin's lymphoma is a B-cell lymphoma, such as a diffuse large B-cell lymphoma, primary mediastinal B-cell lymphoma, follicular lymphoma, small lymphocytic lymphoma, mantle cell lymphoma, marginal zone B-cell lymphoma, extranodal marginal zone B-cell lymphoma, nodal marginal zone B-cell lymphoma, splenic marginal zone B-cell lymphoma, Burkitt lymphoma, lymphoplasmacytic lymphoma, hairy cell leukemia, or primary central nervous system (CNS) lymphoma. In certain other embodiments, the non-Hodgkin's lymphoma is a T-cell lymphoma, such as a precursor T-lymphoblastic lymphoma, peripheral T-cell lymphoma, cutaneous T-cell lymphoma, angioimmunoblastic T-cell lymphoma, extranodal natural killer/T-cell lymphoma, enteropathy type T-cell lymphoma, subcutaneous panniculitis-like T-cell lymphoma, anaplastic large cell lymphoma, or peripheral T-cell lymphoma.

(iii) Treating Respiratory Disorders

Another aspect of the invention provides a method of treating a respiratory disorder. The method comprises administering to a patient in need thereof a therapeutically effective amount of a pharmaceutically acceptable salt of a compound of formula I or formula I-A, e.g., the compound of formula I or formula I-A as a deuterium chloride salt or a hydrochloride salt described herein, to treat the respiratory disorder. In certain embodiments, the method comprises administering to a patient in need thereof a therapeutically effective amount of a deuterium chloride salt of the compound of formula I, e.g., a crystalline deuterium chloride salt form as described herein, to treat the respiratory disorder. In certain embodiments, the method comprises administering to a patient in need thereof a therapeutically effective amount of a hydrochloride salt of the compound of formula I-A, e.g., a crystalline hydrochloride salt form described herein, to treat the respiratory disorder.

In certain embodiments, the respiratory disorder is chronic obstructive pulmonary disease, asthma, bronchitis, cystic fibrosis, pulmonary edema, pulmonary embolism, pulmonary arterial hypertension, pneumonia, pulmonary sarcoidosis, silicosis, pulmonary fibrosis, respiratory failure, acute respiratory distress syndrome, emphysema, chronic bronchitis, tuberculosis, lung cancer, or a chronic respiratory condition. In certain embodiments, the respiratory disorder is chronic obstructive pulmonary disease, asthma, or a chronic respiratory condition. In certain other embodiments, the respiratory disorder is chronic obstructive pulmonary disease. In yet other embodiments, the respiratory disorder is bronchitis, cystic fibrosis, pulmonary edema, pulmonary embolism, pneumonia, pulmonary sarcoidosis, silicosis, pulmonary fibrosis, respiratory failure, acute respiratory distress syndrome, emphysema, chronic bronchitis, tuberculosis, or lung cancer. In certain embodiments, the asthma is mild asthma, moderate asthma, severe asthma, or steroid-resistant asthma.

(iv) Treatment of Neurological Disorders

Accordingly, one aspect of the invention provides a method of treating a neurological disorder selected from the group consisting of Alzheimer's disease, Parkinson's disease, amyotrophic lateral sclerosis, Friedreich's ataxia, autism spectrum disorder, depression, mild cognitive impairment, Down syndrome, neurodegeneration, adrenoleukodystrophy, adrenomyeloneuropathy, Zellweger's disease, Huntington's disease, stroke, traumatic brain injury, substance abuse, spinal cord injury, neuronal injury, major depression or bipolar disorder comorbid with metabolic syndrome, and a neurological disorder caused by functional mitochondrial impairment. The method comprises administering to a patient in need thereof a therapeutically effective amount of a pharmaceutically acceptable salt of a compound of formula I or formula I-A, e.g., the compound of formula I or formula I-A as a deuterium chloride salt or a hydrochloride salt described herein, to treat the neurological disorder. In certain embodiments, the method comprises administering to a patient in need thereof a therapeutically effective amount of a deuterium chloride salt of the compound of formula I, e.g., a crystalline deuterium chloride salt form as described herein, to treat the neurological disorder. In certain embodiments, the method comprises administering to a patient in need thereof a therapeutically effective amount of a hydrochloride salt of the compound of formula I-A, e.g., a crystalline hydrochloride salt form described herein, to treat the neurological disorder. In certain embodiments, the neurological disorder is selected from the group consisting of Alzheimer's disease, Parkinson's disease, amyotrophic lateral sclerosis, Friedreich's ataxia, autism spectrum disorder, depression, mild cognitive impairment, neurodegeneration, adrenoleukodystrophy, adrenomyeloneuropathy, Huntington's disease, stroke, traumatic brain injury, substance abuse, spinal cord injury, neuronal injury, and major depression or bipolar disorder comorbid with metabolic syndrome. In certain embodiments, the neurological disorder is selected from the group consisting of Alzheimer's disease, Parkinson's disease, amyotrophic lateral sclerosis, Friedreich's ataxia, depression, mild cognitive impairment, neurodegeneration, adrenoleukodystrophy, adrenomyeloneuropathy, and Huntington's disease. In certain other embodiments, the neurological disorder is Alzheimer's disease. In certain other embodiments, the neurological disorder is Down syndrome. In certain other embodiments, the neurological disorder is adrenoleukodystrophy. In certain other embodiments, the neurological disorder is adrenomyeloneuropathy.

In certain other embodiments, the neurological disorder is a cognitive disorder, such as cognitive impairment and/or memory impairment. The cognitive impairment may be, for example, cognitive impairment associated with Alzheimer's disease.

In certain embodiments, the substance abuse is one or more of alcohol craving, heroin dependence, and nicotine dependence.

(v) Treating a Symptom of Hepatitis

Another aspect of the invention provides a method of treating a symptom of hepatitis. The method comprises administering to a patient in need thereof a therapeutically effective amount of a pharmaceutically acceptable salt of a compound of formula I or formula I-A, e.g., the compound of formula I or formula I-A as a deuterium chloride salt or a hydrochloride salt described herein, to treat the hepatitis. In certain embodiments, the method comprises administering to a patient in need thereof a therapeutically effective amount of a deuterium chloride salt of the compound of formula I, e.g., a crystalline deuterium chloride salt form as described herein, to treat the hepatitis. In certain embodiments, the method comprises administering to a patient in need thereof a therapeutically effective amount of a hydrochloride salt of the compound of formula I-A, e.g., a crystalline hydrochloride salt form described herein, to treat the hepatitis.

(vi) Treating Cardiovascular Disease

Another aspect of the invention provides a method of treating a cardiovascular disease. The method comprises administering to a patient in need thereof a therapeutically effective amount of a pharmaceutically acceptable salt of a compound of formula I or formula I-A, e.g., the compound of formula I or formula I-A as a deuterium chloride salt or a hydrochloride salt described herein, to treat the cardiovascular disease. In certain embodiments, the method comprises administering to a patient in need thereof a therapeutically effective amount of a deuterium chloride salt of the compound of formula I, e.g., a crystalline deuterium chloride salt form as described herein, to treat the cardiovascular disease. In certain embodiments, the method comprises administering to a patient in need thereof a therapeutically effective amount of a hydrochloride salt of the compound of formula I-A, e.g., a crystalline hydrochloride salt form described herein, to treat the cardiovascular disease. In certain embodiments, the cardiovascular disease is hypertension, hyperlipidemia, atherosclerosis, improper vascular function, dyslipidemia, stenosis, restenosis, myocardial infarction, stroke, intracranial hemorrhage, acute coronary syndrome, stable angina pectoris, or unstable angina pectoris. In certain other embodiments, the cardiovascular disorder is intracranial hemorrhage, acute coronary syndrome, stable angina pectoris, or unstable angina pectoris.

In another aspect, the invention provides a method for preventing stroke in a patient. The method comprises administering to a patient in need thereof a therapeutically effective amount of a pharmaceutically acceptable salt of a compound of formula I or formula I-A, e.g., the compound of formula I or formula I-A as a deuterium chloride salt or a hydrochloride salt described herein, to prevent stroke in a patient. In certain embodiments, the method comprises administering to a patient in need thereof a therapeutically effective amount of a deuterium chloride salt of the compound of formula I, e.g., a crystalline deuterium chloride salt form as described herein, to prevent stroke in a patient. In certain embodiments, the method comprises administering to a patient in need thereof a therapeutically effective amount of a hydrochloride salt of the compound of formula I-A, e.g., a crystalline hydrochloride salt form described herein, to prevent stroke in a patient.

The method of treatment or the method of prevention may involve a patient at risk for central nervous system ischemic stroke, or may involve a patient at risk for stroke due to cardiovascular disease.

(vii) Reducing the Amount of a Triglyceride or Low-Density Lipoprotein

Another aspect of the invention provides a method of reducing the amount of a triglyceride or low-density lipoprotein (LDL) in a patient. The method comprises administering to a patient in need thereof a therapeutically effective amount of a pharmaceutically acceptable salt of a compound of formula I or formula I-A, e.g., the compound of formula I or formula I-A as a deuterium chloride salt or a hydrochloride salt described herein, to reduce the amount of a triglyceride or low-density lipoprotein (LDL) in a patient. In certain embodiments, the method comprises administering to a patient in need thereof a therapeutically effective amount of a deuterium chloride salt of the compound of formula I, e.g., a crystalline deuterium chloride salt form as described herein, to reduce the amount of a triglyceride or low-density lipoprotein (LDL) in a patient. In certain embodiments, the method comprises administering to a patient in need thereof a therapeutically effective amount of a hydrochloride salt of the compound of formula I-A, e.g., a crystalline hydrochloride salt form described herein, to reduce the amount of a triglyceride or low-density lipoprotein (LDL) in a patient.

In certain embodiments, the method provides a reduction of at least 1%, 5%, 10%, or 25% in the amount of a triglyceride or low-density lipoprotein (LDL) in the patient.

(viii) Increasing the Amount of High-Density Lipoprotein

Another aspect of the invention provides a method of increasing the amount of high-density lipoprotein (HDL) in a patient. The method comprises administering to a patient in need thereof a therapeutically effective amount of a pharmaceutically acceptable salt of a compound of formula I or formula I-A, e.g., the compound of formula I or formula I-A as a deuterium chloride salt or a hydrochloride salt described herein, to increase the amount of high-density lipoprotein (HDL) in a patient. In certain embodiments, the method comprises administering to a patient in need thereof a therapeutically effective amount of a deuterium chloride salt of the compound of formula I, e.g., a crystalline deuterium chloride salt form as described herein, to increase the amount of high-density lipoprotein (HDL) in a patient. In certain embodiments, the method comprises administering to a patient in need thereof a therapeutically effective amount of a hydrochloride salt of the compound of formula I-A, e.g., a crystalline hydrochloride salt form described herein, to increase the amount of high-density lipoprotein (HDL) in a patient.

In certain embodiments, the method provides an increase of at least 1%, 5%, 10%, or 25% in the amount of high-density lipoprotein (HDL) in a patient.

(ix) Treating an Inflammatory or Immune-Mediated Disorder

Another aspect of the invention provides a method of treating an inflammatory or immune-mediated disorder selected from the group consisting of chronic kidney disease, arthritis, a primary cicatricial alopecia, lung fibrosis, multiple sclerosis, endotoxemia, sepsis, septic shock, laminitis, inflammatory bowel disease, colitis, Crohn's disease, rheumatoid arthritis, lupus, myasthenia gravis, vasculitis, chronic pancreatitis, a hyperproliferative skin disorder, an inflammatory skin disorder, rhinitis (e.g., allergic rhinitis), and a dermatological condition. The method comprises administering to a patient in need thereof a therapeutically effective amount of a pharmaceutically acceptable salt of a compound of formula I or formula I-A, e.g., the compound of formula I or formula I-A as a deuterium chloride salt or a hydrochloride salt described herein, to treat the inflammatory or immune-mediated disorder. In certain embodiments, the method comprises administering to a patient in need thereof a therapeutically effective amount of a deuterium chloride salt of the compound of formula I, e.g., a crystalline deuterium chloride salt form as described herein, to treat the inflammatory or immune-mediated disorder. In certain embodiments, the method comprises administering to a patient in need thereof a therapeutically effective amount of a hydrochloride salt of the compound of formula I-A, e.g., a crystalline hydrochloride salt form described herein, to treat the inflammatory or immune-mediated disorder. In certain embodiments, the inflammatory or immune-mediated disorder is selected from the group consisting of chronic kidney disease, arthritis, a primary cicatricial alopecia, lung fibrosis, multiple sclerosis, endotoxemia, sepsis, septic shock, laminitis, inflammatory bowel disease, colitis, Crohn's disease, rheumatoid arthritis, lupus, myasthenia gravis, vasculitis, chronic pancreatitis, a hyperproliferative skin disorder, an inflammatory skin disorder, and a dermatological condition. In certain embodiments, the inflammatory or immune-mediated disorder is selected from the group consisting of chronic kidney disease, arthritis, a primary cicatricial alopecia, lung fibrosis, multiple sclerosis, endotoxemia, sepsis, septic shock, laminitis, inflammatory bowel disease, colitis, Crohn's disease, rheumatoid arthritis, lupus, myasthenia gravis, vasculitis, chronic pancreatitis, a hyperproliferative skin disorder, an inflammatory skin disorder, and a dermatological condition, in certain embodiments, the chronic kidney disease may be, for example, polycystic kidney disease (such as autosomal dominant or autosomal recessive).

(x) Treating a Dermatological Disorder

Another aspect of the invention provides a method of treating a dermatological disorder selected from the group consisting of psoriasis, atopic dermatitis, acne, leukoplakia, scleroderma, and a skin malignancy. The method comprises administering to a patient in need thereof a therapeutically effective amount of a pharmaceutically acceptable salt of a compound of formula I or formula I-A, e.g., the compound of formula I or formula I-A as a deuterium chloride salt or a hydrochloride salt described herein, to treat the dermatological disorder. In certain embodiments, the method comprises administering to a patient in need thereof a therapeutically effective amount of a deuterium chloride salt of the compound of formula I, e.g., a crystalline deuterium chloride salt form as described herein, to treat the dermatological disorder. In certain embodiments, the method comprises administering to a patient in need thereof a therapeutically effective amount of a hydrochloride salt of the compound of formula I-A, e.g., a crystalline hydrochloride salt form described herein, to treat the dermatological disorder. In certain embodiments, the administering is by topical administration.

(xi) Modulating Expression of Pro-Inflammatory Cytokines

Another aspect of the invention provides a method of modulating expression of a pro-inflammatory cytokine (e.g., TNFα, IL-1β, IL-6, IL-17, IL-23, or MCP-1) in a patient suffering from an inflammatory disorder. The method comprises administering to a patient in need thereof a therapeutically effective amount of a pharmaceutically acceptable salt of a compound of formula I or formula I-A, e.g., the compound of formula I or formula I-A as a deuterium chloride salt or a hydrochloride salt described herein, to modulate expression of a pro-inflammatory cytokine (e.g., TNFα, IL-1β, or IL-6) in a patient suffering from an inflammatory disorder. In certain embodiments, the method comprises administering to a patient in need thereof a therapeutically effective amount of a deuterium chloride salt of the compound of formula I, e.g., a crystalline deuterium chloride salt form as described herein, to modulate expression of a pro-inflammatory cytokine (e.g., TNFα, IL-1β, or IL-6) in a patient suffering from an inflammatory disorder. In certain embodiments, the method comprises administering to a patient in need thereof a therapeutically effective amount of a hydrochloride salt of the compound of formula I-A, e.g., a crystalline hydrochloride salt form described herein, to modulate expression of a pro-inflammatory cytokine (e.g., TNFα, IL-1β, or IL-6) in a patient suffering from an inflammatory disorder. In certain embodiments, the pro-inflammatory cytokine is TNFα.

Another aspect of the invention provides a method of modulating expression of an anti-inflammatory cytokine in a patient suffering from an inflammatory disorder. The method comprises administering to a patient in need thereof a therapeutically effective amount of a pharmaceutically acceptable salt of a compound of formula I or formula I-A, e.g., the compound of formula I or formula I-A as a deuterium chloride salt or a hydrochloride salt described herein, to modulate expression of an anti-inflammatory cytokine in a patient suffering from an inflammatory disorder. In certain embodiments, the method comprises administering to a patient in need thereof a therapeutically effective amount of a deuterium chloride salt of the compound of formula I, e.g., a crystalline deuterium chloride salt form as described herein, to modulate expression of an anti-inflammatory cytokine in a patient suffering from an inflammatory disorder. In certain embodiments, the method comprises administering to a patient in need thereof a therapeutically effective amount of a hydrochloride salt of the compound of formula I-A, e.g., a crystalline hydrochloride salt form described herein, to modulate expression of an anti-inflammatory cytokine in a patient suffering from an inflammatory disorder.

(xii) Modulating Macrophage Function

Another aspect of the invention provides a method of modulating macrophage function in a patient suffering from an infection, inflammatory disorder, or autoimmune disease. The method comprises administering to a patient in need thereof a therapeutically effective amount of a pharmaceutically acceptable salt of a compound of formula I or formula I-A, e.g., the compound of formula I or formula I-A as a deuterium chloride salt or a hydrochloride salt described herein, to modulate macrophage function in a patient suffering from an infection. In certain embodiments, the method comprises administering to a patient in need thereof a therapeutically effective amount of a deuterium chloride salt of the compound of formula I, e.g., a crystalline deuterium chloride salt form as described herein, to modulate macrophage function in a patient suffering from an infection, inflammatory disorder, or autoimmune disease. In certain embodiments, the method comprises administering to a patient in need thereof a therapeutically effective amount of a hydrochloride salt of the compound of formula I-A, e.g., a crystalline hydrochloride salt form described herein, to modulate macrophage function in a patient suffering from an infection.

(xiii) Method of Promoting Wound Healing

Another aspect of the invention provides a method of promoting wound healing. The method comprises administering to a patient in need thereof a therapeutically effective amount of a pharmaceutically acceptable salt of a compound of formula I or formula I-A, e.g., the compound of formula I or formula I-A as a deuterium chloride salt or a hydrochloride salt described herein, to promote wound healing. In certain embodiments, the method comprises administering to a patient in need thereof a therapeutically effective amount of a deuterium chloride salt of the compound of formula I, e.g., a crystalline deuterium chloride salt form as described herein, to promote wound healing. In certain embodiments, the method comprises administering to a patient in need thereof a therapeutically effective amount of a hydrochloride salt of the compound of formula I-A, e.g., a crystalline hydrochloride salt form described herein, to promote wound healing. In certain embodiments, the administering is by topical administration.

(xiv) Treating Skin Defects

Another aspect of the invention provides a method of treating skin defects caused by exposure to ultraviolet radiation. The method comprises administering to a patient in need thereof a therapeutically effective amount of a pharmaceutically acceptable salt of a compound of formula I or formula I-A, e.g., the compound of formula I or formula I-A as a deuterium chloride salt or a hydrochloride salt described herein, to treat skin defects caused by exposure to ultraviolet radiation. In certain embodiments, the method comprises administering to a patient in need thereof a therapeutically effective amount of a deuterium chloride salt of the compound of formula I, e.g., a crystalline deuterium chloride salt form as described herein, to treat skin defects caused by exposure to ultraviolet radiation. In certain embodiments, the method comprises administering to a patient in need thereof a therapeutically effective amount of a hydrochloride salt of the compound of formula I-A, e.g., a crystalline hydrochloride salt form described herein, to treat skin defects caused by exposure to ultraviolet radiation.

(xv) Method of Modulating Stem Cell Differentiation

Another aspect of the invention provides a method of modulating stem cell differentiation, such as in a patient. The method comprises administering to a patient in need thereof a therapeutically effective amount of a pharmaceutically acceptable salt of a compound of formula I or formula I-A, e.g., the compound of formula I or formula I-A as a deuterium chloride salt or a hydrochloride salt described herein, to modulate stem cell differentiation, such as in a patient. In certain embodiments, the method comprises administering to a patient in need thereof a therapeutically effective amount of a deuterium chloride salt of the compound of formula I, e.g., a crystalline deuterium chloride salt form as described herein, to modulate stem cell differentiation, such as in a patient. In certain embodiments, the method comprises administering to a patient in need thereof a therapeutically effective amount of a hydrochloride salt of the compound of formula I-A, e.g., a crystalline hydrochloride salt form described herein, to modulate stem cell differentiation, such as in a patient.

(xvi) Additional Medical Disorders

Another aspect of the invention provides a method of treating a disorder selected from the group consisting of transplant rejection, liver functional impairment, Rabson-Mendenhall syndrome, Donohue syndrome, Leber hereditary optic neuropathy, myotonic dystrophy, ototoxicity, Niemann Pick disease, autosomal dominant optic atrophy, spinal bulbar muscular atrophy, Mohr-Tranebjaerg syndrome, hereditary spastic paraplegia, MELAS syndrome, monoclonal immunoglobulin deposition disease (MIDD), deafness, insulin resistance in a patient receiving growth hormone, and chronic progressive external ophthalmo-plegia with mitochondrial myopathy. The method comprises administering to a patient in need thereof a therapeutically effective amount of a pharmaceutically acceptable salt of a compound of formula I or formula I-A, e.g., the compound of formula I or formula I-A as a deuterium chloride salt or a hydrochloride salt described herein, to treat the disorder. In certain embodiments, the method comprises administering to a patient in need thereof a therapeutically effective amount of a deuterium chloride salt of the compound of formula I, e.g., a crystalline deuterium chloride salt form as described herein, to treat the disorder. In certain embodiments, the method comprises administering to a patient in need thereof a therapeutically effective amount of a hydrochloride salt of the compound of formula I-A, e.g., a crystalline hydrochloride salt form described herein, to treat the disorder.

(xvii) Preventing Medical Disorders

Also provided are methods of preventing a medical disorder in a patient. The method comprises administering to a patient in need thereof a therapeutically effective amount of a pharmaceutically acceptable salt of a compound of formula I or formula I-A, e.g., the compound of formula I or formula I-A as a deuterium chloride salt or a hydrochloride salt described herein, to prevent the medical disorder. In certain embodiments, the method comprises administering to a patient in need thereof a therapeutically effective amount of a deuterium chloride salt of the compound of formula I, e.g., a crystalline deuterium chloride salt form as described herein, to prevent the medical disorder. In certain embodiments, the method comprises administering to a patient in need thereof a therapeutically effective amount of a hydrochloride salt of the compound of formula I-A, e.g., a crystalline hydrochloride salt form described herein, to prevent the medical disorder. The medical disorder may be one or more of the medical disorders recited above, such as a neurological disorder (e.g., Alzheimer's disease or Parkinson's disease), cancer (e.g., non-small cell lung cancer or hepatocellular carcinoma), a metabolic disorder, a cardiovascular disorder (e.g., in-stent renarrowing in diabetes patients, reinfarction in diabetes patients, or cardiac allograft vasculopathy after heart transplant), or a respiratory disorder (e.g., chronic obstructive pulmonary disease).

(xviii) Additional Medical Uses

The invention provides methods of using the compounds and solid forms described herein for therapy comprising regenerative medicine. Also provided herein are methods of treating a veterinary disorder, such as laminitis. The method comprises administering to a patient in need thereof a therapeutically effective amount of a pharmaceutically acceptable salt of a compound of formula I or formula I-A, e.g., the compound of formula I or formula I-A as a deuterium chloride salt or a hydrochloride salt described herein, to treat the veterinary disorder. In certain embodiments, the method comprises administering to a patient in need thereof a therapeutically effective amount of a deuterium chloride salt of the compound of formula I, e.g., a crystalline deuterium chloride salt form as described herein, to treat the veterinary disorder. In certain embodiments, the method comprises administering to a patient in need thereof a therapeutically effective amount of a hydrochloride salt of the compound of formula I-A, e.g., a crystalline hydrochloride salt form described herein, to treat the veterinary disorder.

In certain embodiments, the pharmaceutically acceptable salts of the compound of formula I or formula I-A provided herein may be administered as the sole active agent, or they may be administered in combination with other therapeutically active agents (e.g., a combination therapy).

It is contemplated that combination therapies of the invention described herein may work synergistically in the treatment of particular conditions, diseases or disorders described herein, and/or one or more symptoms associated with such conditions, diseases or disorders. It is further contemplated that the pharmaceutically acceptable salts of the compound of formula I or formula I-A provided herein may also work to alleviate adverse effects associated with a second therapeutically active agent, and vice versa.

In various embodiments, one or more second therapeutically active agents can be used in the methods and compositions provided herein. In certain embodiments, the one or more second therapeutically active agents may be large molecules (e.g., proteins) or small molecules (e.g., synthetic inorganic, organometallic, or organic molecules).

In certain embodiments, the combination therapy comprises a pharmaceutically acceptable salt of the compound of formula I or formula I-A described herein and a second therapeutically active agent for the treatment of a condition, disease or disorder described herein (e.g., a neurological disorder, a cancer, a respiratory disorder, a metabolic disorder, a hepatitis, a cardiovascular disease, an inflammatory or immune-mediated disorder, a dermatological disorder, a wound, a skin defect, etc.).

In certain embodiments, the second therapeutically active agent may be an agent useful for the treatment of a metabolic disorder, such therapeutically active agents may include, but are not limited to, metformin, imeglimin, a dipeptidyl peptidase IV inhibitor (e.g., sitagliptin, vildagliptin, or the like), a statin (e.g., a HMG-CoA reductase inhibitor, such as atorvastatin, cerivastatin, fluvastatin, lovastatin, mevastatin, simvastatin, rosuvastatin, pravastatin, or combinations thereof), an AMPK activator, a thyroid-O agonist, a GLP-1 agonist, a GLP-2 agonist, or an SGLT2 inhibitor.

In certain embodiments, the second therapeutically active agent is a diuretic agent (e.g., hydrochlorothiazide).

In certain embodiments, the second therapeutically active agent may be an agent useful for the treatment of hypertension, diabetes, or an inflammatory disorder. In certain embodiments, the second therapeutically active agent may be an agent that limits the activity of the renin-angiotensin system, such as an angiotensin converting enzyme inhibitor (e.g., an ACE inhibitor, such as ramipril, captopril, enalapril, or the like), an angiotensin receptor blocker (e.g., candesartan, losartan, olmesartan, or the like), or a renin inhibitor. In certain embodiments, the second therapeutic agent may limit hypertension by alternate means, for example, a beta-adrenergic receptor blocker or calcium channel blocker (e.g., amlodipine).

In certain embodiments, second therapeutically active agent is a glucocorticoid agonist. In certain embodiments, a combination therapy comprising a pharmaceutically acceptable salt of the compound of formula I or formula I-A described herein and a glucocorticoid agonist may be useful for the treatment of an inflammatory disorder, such as therapy for suppressing an immune response, preventing transplant rejection, and treating autoimmune disease. Exemplary disorders include, for example, rheumatoid arthritis, lupus, myasthenia gravis, muscular dystrophy vasculitis, multiple sclerosis, chronic obstructive pulmonary disease (COPD), inflammatory bowel disease, treatment of acute allergic reactions, and transplant rejection.

In certain embodiments, a combination therapy comprising a pharmaceutically acceptable salt of the compound of formula I or formula I-A described herein and a second therapeutically active agent that increases cAMP or a beta-adrenergic agonist may be useful in the treatment of a kidney disease. Exemplary beta-adrenergic agonists include, but are not limited to, a beta-1-adrenergic agonist, a beta-2-adrenergic agonist, a beta-3-adrenergic agonist, or combinations thereof. In certain embodiments, the second therapeutically active agent is noradrenaline, isoprenaline, dobutamine, salbutamol, levosalbutamol, terbutaline, pirbuterol, procaterol, metaproterenol, fenoterol, bitolterol mesylate, salmeterol, formoterol, bambuterol, clenbuterol, indacaterol, L-796568, amibegron, solabegron, isoproterenol, albuterol, metaproterenol, arbutamine, befunolol, bromoacetylalprenololmenthane, broxaterol, cimaterol, cirazoline, denopamine, dopexamine, epinephrine, etilefrine, hexoprenaline, higenamine, isoetharine, isoxsuprine, mabuterol, methoxyphenamine, nylidrin, oxyfedrine, prenalterol, ractopamine, reproterol, rimiterol, ritodrine, tretoquinol, tulobuterol, xamoterol, zilpaterol, zinterol, or a pharmaceutically acceptable salt thereof; or a combination of any of the foregoing.

In certain embodiments, the combination therapy comprises a pharmaceutically acceptable salt of the compound of formula I or formula I-A described herein and a second therapeutically active agent useful in the treatment of a cancer. Exemplary second therapeutically active agents useful for the treatment of cancer include, but are not limited to, an alkylating agent, an anti-metabolite (e.g., a molecule that impedes DNA and/or RNA synthesis), an anti-microtubule agent, a topoisomerase inhibitor, a cytotoxic antibiotic, a tyrosine kinase inhibitor, an inhibitor of tumor necrosis factor alpha, anti-neoplastic radiation therapy, or a Programmed Death protein-1 (PD-1) modulator (e.g., an inhibitor). In certain embodiments, the second therapeutically active agent useful for the treatment of a cancer is azacitidine, azathioprine, bleomycin, carboplatin, capecitabine, carmustine, cisplatin, chlorambucil, cyclophosphamide, cytarabine, dacarbazine, daunorubicin, docetaxel, doxifluridine, doxorubicin, epirubicin, epothilone, etoposide, fluorouracil, fulvestrant, gemcitabine, hydroxyurea, idarubicin, imatinib, lomustine, mechlorethamine, mercaptopurine, methotrexate, mitoxantrone, oxaliplatin, paclitaxel, pemetrexed, procarbazine, raloxifene, teniposide, temozolomide, tamoxifen, toremifene, valrubicin, vinblastine, vincristine, vindesine, vinorelbine, or a pharmaceutically acceptable salt thereof; or a combination of any of the foregoing.

In certain embodiments, the second therapeutically active agent useful for the treatment of a cancer is abraxane; acivicin; aclarubicin; acodazole hydrochloride; acronine; adozelesin; aldesleukin; altretamine; ambomycin; ametantrone acetate; amrubicin; amsacrine; anastrozole; anthramycin; asparaginase; asperlin; azacitidine; azetepa; azotomycin; batimastat; benzodepa; bicalutamide; bisantrene hydrochloride; bisnafide dimesylate, bizelesin; bleomycin sulfate; brequinar sodium; bropirimine; busulfan; cactinomycin; calusterone; caracemide; carbetimer; carboplatin; carmustine; carubicin hydrochloride; carzelesin; cedefmgol; celecoxib; chlorambucil; cirolemycin; cisplatin; cladribine; crisnatol mesylate; cyclophosphamide; cytarabine; dacarbazine; dactinomycin; daunorubicin hydrochloride; decitabine; dexormaplatin; dezaguanine; dezaguanine mesylate; diaziquone; docetaxel; doxorubicin; doxorubicin hydrochloride; raloxifene; raloxifene citrate; dromostanolone propionate; duazomycin; edatrexate; eflornithine hydrochloride; elsamitrucin; enloplatm; enpromate; epipropidine; epirubicin hydrochloride; erbulozole; esorubicin hydrochloride; estramustine; estramustine phosphate sodium; etanidazole; etoposide; etoposide phosphate; etoprine; fadrozole hydrochloride; fazarabine; fenretinide; floxuridine; fludarabine phosphate; fluorouracil; flurocitabine; fosquidone; fostriecin sodium; gemcitabine; gemcitabine hydrochloride; herceptin; hydroxyurea; idarubicin hydrochloride; ifosfamide; ilmofosine; iproplatin; irinotecan; irinotecan hydrochloride; lanreotide acetate; lapatinib; letrozole; leuprolide acetate; liarozole hydrochloride; lometrexol sodium; lomustine; losoxantrone hydrochloride; masoprocol; maytansine; mechlorethamine hydrochloride; megestrol acetate; melengestrol acetate; melphalan; menogaril; mercaptopurine; methotrexate; methotrexate sodium; metoprine; meturedepa; mitindomide; mitocarcin; mitocromin; mitogillin; mitomalcin; mitomycin; mitosper; mitotane; mitoxantrone hydrochloride; mycophenolic acid; nocodazole; nogalamycin; ormaplatin; oxisuran; paclitaxel; pegaspargase; peliomycin; pentamustine; peplomycin sulfate; perfosfamide; pipobroman; piposulfan; piroxantrone hydrochloride; plicamycin; plomestane; porfimer sodium; portiromycin; prednimustine; procarbazine hydrochloride; puromycin; puromycin hydrochloride; pyrazofurin; riboprine; romidepsin; safingol; safingol hydrochloride; semustine; simtrazene; sparfosate sodium; sparsomycin; spirogermanium hydrochloride; spiromustine; spiroplatin; a stem cell treatment; streptonigrin; streptozocin; sulofenur; talisomycin; tecogalan sodium; taxotere; tegafur; teloxantrone hydrochloride; temoporfin; teniposide; teroxirone; testolactone; thiamiprine; thioguanine; thiotepa; tiazofurin; tirapazamine; toremifene citrate; trestolone acetate; triciribine phosphate; trimetrexate; trimetrexate glucuronate; triptorelin; tubulozole hydrochloride; uracil mustard; uredepa; vapreotide; verteporfin; vinblastine sulfate; vincristine sulfate; vindesine; vindesine sulfate; vinepidine sulfate; vinglycinate sulfate; vinleurosine sulfate; vinorelbine tartrate; vinrosidine sulfate; vinzolidine sulfate; vorozole; zeniplatin; zinostatin; zorubicin hydrochloride, or combinations thereof.

Administration of a pharmaceutically acceptable salt of the compound of formula I or formula I-A described herein and the second therapeutically active agent(s) to a patient can occur simultaneously or sequentially by the same or different routes of administration. The suitability of a particular route of administration employed for a particular active agent will depend on the active agent itself (e.g., whether it can be administered orally without decomposing prior to entering the blood stream) and the disease being treated. One route of administration for compounds provided herein is oral. Routes of administration for the second active agents or ingredients are known to those of ordinary skill in the art. See, e.g., Physicians' Desk Reference (60th Ed., 2006).

EXAMPLES

In order that the disclosure described herein may be more fully understood, the following examples are set forth. The synthetic and biological examples described in this application are offered to illustrate the compounds, pharmaceutical compositions, and methods provided herein and are not to be construed in any way as limiting their scope.

Example 1: Synthesis of Deuterium-Enriched (R)-Pioglitazone L-Dibenzoyl Tartrate Salt Reaction temperatures are reported as internal temperatures. Chemical intermediates, reagents, and solvents were obtained from commercial sources.

Filtration: Solid products were isolated by filtration over a PTFE Büchner funnel using MN 617 G (fast filtration, phosphate-free; ref: MN 494024) and MN640m (ref: MN 203015) filter paper (unless otherwise stated) and washed with 1:1 MeOD:$D_2O$ (v/v) in a plug-flow method (portions; 2×/3×) (unless otherwise stated).

Drying: After filtration, first solids were air-dried in vacuo for a few hours (3-4 h) and then dried (24-72 h) in a drying oven at 50° C./42° C. fitted with a vacuum pump.

NMR: $^1$H spectra were recorded on a Bruker Avance 300 MHz or higher spectrometer. Chemical shifts were referenced to residual solvent signals at δ 2.50 (DMSO-d6) relative to TMS as internal standard wherever applied.

HPLC: For % d.e./% e.e. measurement, all samples were dissolved in MeOH to make a solution of 1 mg/mL.

HPLC for identity and chemical purity measurement: Samples were run on a 150 mm×4.6 mm, 5 μm YMC triart C18 column. The mobile phase was an isocratic elution system with 1:1 0.1 M $NH_4OAc:CH_3CN$ plus 2% HOAc. Flow rate was 0.75 mL/min; run time, 35 min; and detector wavelength, 269 nm.

In the following examples, when details of an example run are presented, notes in square brackets ([ ]) are used to denote optional changes that are not part of the example run but could be performed or were performed in another run.

Step 1: Preparation of Racemic Deuterium-Enriched Pioglitazone (Compound B)

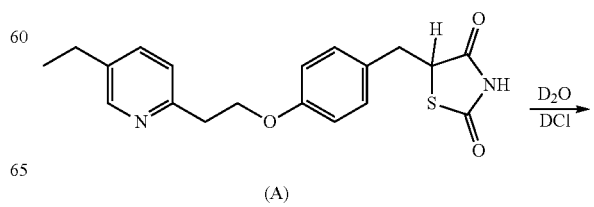

(A)

-continued

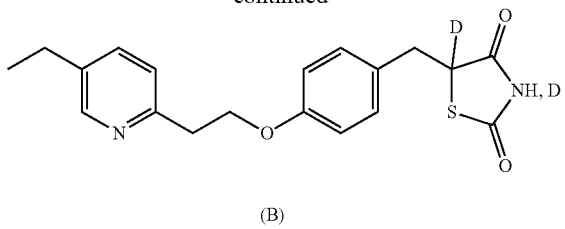

(B)

Pioglitazone HCl (compound A HCl salt) was dissolved in D$_2$O at elevated temperature. After stirring at 90° C. to 100° C. for at least 5 h, a small amount of DCl was added followed by cooling down to ambient temperature. After aging the suspension for a few hours at 15° C. to 25° C., the product was filtered off as compound B DCl salt. After this first cycle, approximately 95% of the hydrogen at the chiral center had been exchanged by deuterium.

If desired, the crude product was then subjected to a second cycle of the same treatment to further increase the deuteration grade to 98+% in compound (B) as determined by $^1$H-NMR.

Example Run:

1$^{st}$ deuteration cycle: 19.96 kg pioglitazone (compound (A)) was charged in a 100 L glass-lined vessel. 79.54 kg (71.86 L; 4.0 equivalents w/w) D$_2$O was then charged in the same vessel. The reaction mixture was heated and stirred to about 95° C. and stirred at that temperature for 5 h. [Temperatures can be from about 90° C. to about 100° C. (preferably 95° C.) for at least 5 h. A temperature of 95° C. or lower will lead to lower deuteration grade, while temperatures from about 95° C. to about 100° C. worked better. Lower amounts of D$_2$O were tried, but the reaction mixture was difficult to stir with less than 4 w/w equivalents, and increase in deuteration was minimal above 5 w/w equivalents. Significant increase in deuteration grade was observed up until 3 to 4 hours at elevated temperature.] A thin white suspension was observed and 0.13 kg (0.10 L, 0.005 v/w equivalents) 35% DCl in D$_2$O was added, and the transfer line was rinsed with approximately 0.25 L D$_2$O (0.0125 v/w equivalents). The reaction mixture was cooled to about 25° C. over 240 min approximately [Cooling time is at least 3 h to a final temperature from about 15° C. to about 25° C.]. The reaction mixture was then stirred for 13 h approximately at 15° C. [Holding time is at least 5 h from about 15° C. to about 25° C. The solid obtained is more stirrable and filterable if cooled over 3 hours or more rather than only 1 hour.] The crude product was filtered off on a 140 L stainless steel nutsche filter. The product was washed with 5.52 kg (4.99 L; 0.25 v/w equivalents) D$_2$O. The crude product was blown dry in a stream of nitrogen for 3 h approximately [Drying time should be at least 1 h]. The moist crude product was isolated, and a monitoring sample was used for $^1$H-NMR. The sample was then subjected to a second round of deuteration to increase the deuterium content. [Over three runs, % deuteration on chiral center of 96.5%, 97.2%, and 96.9% were observed at this stage.]

Second deuteration cycle: The entire amount of moist crude product was charged in a vessel. 75.57 kg (68.26 L) D$_2$O was then charged. The reaction mixture was heated to about 95° C. for 5 h approximately [Heating can be to a temperature from about 90° C. to about 100° C. (preferably 95° C.) for at least 5 h]. A thin white suspension was observed. 0.12 kg (0.09 L) DCl in D$_2$O 35% was then added, and the transfer line was rinsed with approximately 0.25 L D$_2$O. The reaction mixture was cooled to 25° C. over 4 h [Cooling ramp should be at least 3 h to a temperature from about 15° C. to about 25° C.]. The reaction mixture was stirred at about 20° C. for 9 h [Stirring can be done at 15° C. to 25° C. for at least 5 h]. Then the crude product was filtered off on a 140 L stainless steel nutsche filter and was rinsed with 5.52 kg (4.99 L) D$_2$O. Deuterium NMR showed more than 2 deuteriums per molecule. The compound (B) DCl salt product (or optionally a mixture of HCl and DCl salt) was dried on a 140 L stainless steel nutsche filter in vacuo at about max. 60° C. until LOD (loss on drying) ≤2% (48 h approximately) [Drying temperature should not exceed a maximum of 60° C.].

Step 2: Preparation of Deuterium-Enriched (R)-Pioglitazone L-Dibenzoyl Tartrate Salt (Compound (C))

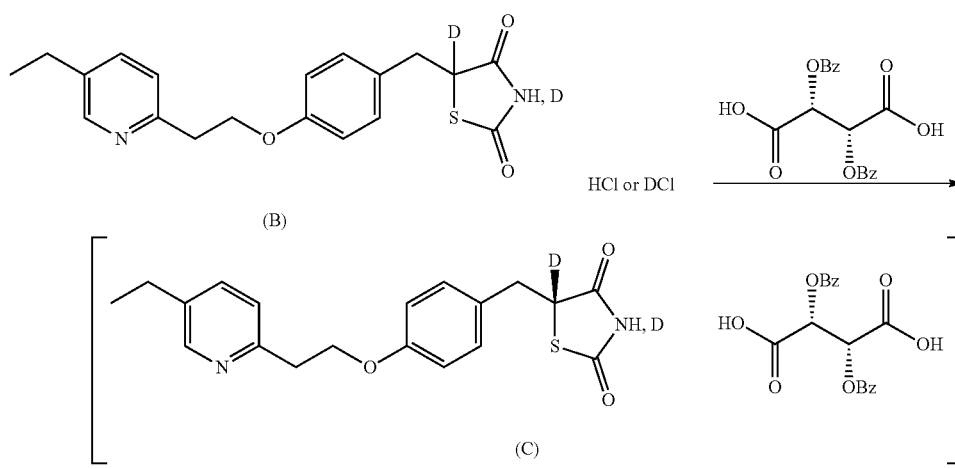

The synthesis started with dissolving compound (B) or salt thereof and L-dibenzoyl tartrate in a mixture of MeOD (methanol-d1) and D$_2$O at elevated temperature. The mixture was then cooled to approximately 55° C. Seed crystals (2% or less w/w relative to (compound B)) were optionally added, followed by a rather slow cooling ramp and extended aging time. Eventually, the product compound (C) was filtered off, washed with a mixture of MeOD and D$_2$O and dried in vacuo.

Example Run:

28.10 kg racemic deuterium-enriched pioglitazone (compound (B)) DCl salt was charged in a 1000 L glass vessel, followed by 25.49 kg L,L-dibenzoyltartaric acid (1 molar equiv.) and 187.3 kg MeOD (230.4 L; 6.67 w/w equivalents) [It is possible to use 0.6 molar equivalents of L,L-dibenzoyltartaric acid resulting in slightly lower yield but comparable % ee]. The reaction mixture was warmed to a temperature from about 60° C. to about 70° C. (65° C. achieved), and 280.9 kg D$_2$O (253.7 L; 10.0 w/w equivalents) was added. The reaction was warmed to 70° C. to 80° C. (76° C. achieved), and the mixture was stirred at that temperature for at least 30 minutes. An almost clear solution was obtained. The mixture was then cooled to 55° C. over 66 min [Cooling time should be at least one hour to a temperature from about 52° C. to about 58° C.]. The mixture was then stirred for 2 h at 56° C. [Stirring can be done for at least 2 hours at a temperature from about 52° C. to about 58° C.]), during which time seed crystals (0.25 kg) of compound (C) were added [Seeding can be with crystals of compound (C) or (C')]. The suspension was cooled to 25° C. for 7.5 hours [Cooling time to a temperature from about 22° C. to about 28° C. should be at least 5 hours]. Then the suspension was stirred for 37 h [Stirring should take at least 15 hours at 22° C. to 28° C.]).

The product was filtered off on a stainless-steel centrifuge, and was washed with a premixed mixture of D$_2$O (13.38 kg; 12.08 L; 0.48 w/w equiv.) and MeOD (9.82 kg; 12.08 L; 0.35 w/w equiv.). The product was blown dry in a steam of nitrogen for at least 1 h. The product compound (C) was then dried in vacuo at a maximum temperature of 60° C. on a Hastelloy vacuum tray dryer. Deuterium NMR showed approximately 2 deuteriums per molecule.

Step 3: Recrystallization of Enantioenriched (R)-Deuterium-Enriched Pioglitazone L-Dibenzoyl Tartrate Salt (Compound (C) to Recrystallized Compound (C'))

Example Run:

To prepare HCl salt derivative: 46.88 kg enantioenriched (R)-deuterium-enriched pioglitazone dibenzoyl tartrate salt (compound (C)) was charged in a 1000 L glass vessel, followed by 185.6 kg MeOH (234.4 L; 4.0 w/w equivalents), 55.0 kg D$_2$O (49.7 L; 1.17 w/w equivalents), and 7.1 kg 35% DCl in D$_2$O (5.6 L; 0.15 w/w equivalents). The reaction mixture was warmed to 60° C. to 70° C. (63° C. achieved), and 218.0 kg D$_2$O (196.9 L; 4.65 w/w equivalents) was added. The reaction was warmed to 70° C. to 80° C., and the mixture was stirred at that temperature for at least 30 minutes. An almost clear solution was obtained. The mixture was then cooled to 55° C. during 85 min. [Cooling time should be at least one hour]. The mixture was then stirred for at 55° C. for 120 min and seed crystals of (compound C') (0.14 kg) were added [Stirring can be performed at 52-58° C. for at least 2 hours during which time seed crystals of compound (C) or (C') could be added if desired]. The suspension was cooled to 26° C. over 10 h 50 min [Cooling ramp to 22° C. to 28° C. should be at least 5 hours long]. Then the suspension was stirred at 25° C. for 34 h 20 min [Suspension should be stirred for at least 15 hours at 22° C. to 28° C.]).

The product was filtered off on a stainless-steel centrifuge, and was washed with a premixed mixture of D$_2$O (17.1 kg; 15.5 L; 0.36 w/w equiv.) and MeOD (12.3 kg; 15.5 L; 0.26 w/w equiv.). The product compound (C') was blown dry in a steam of nitrogen for at least 1 h. The product was then submitted to HPLC for measurement of optical purity. If optical purity was adequate (above 91%), compound (C') was dried in vacuo at a maximum temperature of 60° C. on a Hastelloy vacuum tray dryer. If not, a second recrystallization was performed (actual example: 93% ee; no second recrystallization). Deuterium NMR showed approximately 2 deuteriums per molecule.

If a second or further recrystallizations are necessary, the above procedure can be repeated and the recrystallized material separated and dried in vacuo at a maximum temperature of 60° C. on a Hastelloy vacuum tray dryer as described above.

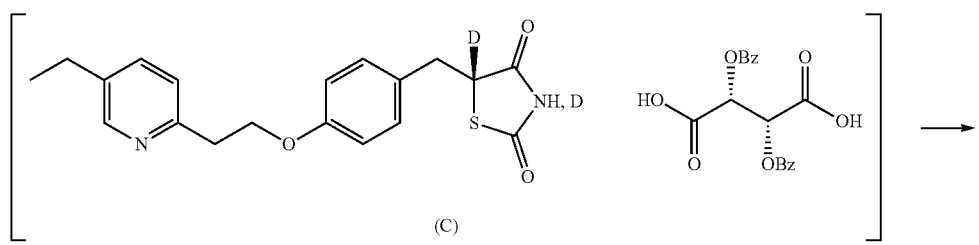

(C)

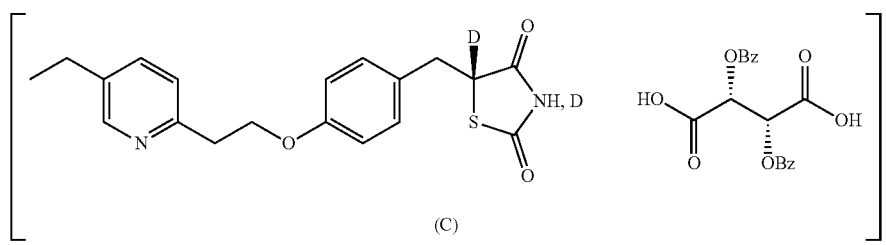

(C')

It should be noted that the details given below include the procedures of both steps b) and c).

To prepare DCl salt derivative: only deuterated solvents were required to be used.

Example 2: Preparation and Characterization of the Crystalline DCl Salt of Deuterium-Enriched (R)-Pioglitazone 278.5 g of deuterium-enriched (R)-pioglitazone L-dibenzoyl tartrate salt (as prepared in Example 1), 450 mL of MeOD and about 38% DCl in $D_2O$ (36 g, 2.9 equiv.) was heated to 50° C. The slightly turbid solution was filtered over a Büchner funnel (100 mL) fitted with porcelain-1 filter and the filtrate was reheated to 50° C. Ethyl acetate (1500 mL) was then added in seven portions (temp. dropped to 30° C.) and the mixture was allowed to attain 20° C. After stirring for 2 hours at this temperature, the crystalline DCl Salt of deuterium-enriched (R)-pioglitazone was isolated by filtration over a Büchner funnel (250 mL) fitted with porcelain-4 filter. After washing thoroughly (in portions) with ethyl acetate (5×250 mL), isolated wet cake was dried overnight at 50° C. in vacuo to obtain 44.6 g (Y=89.9%) of the deuterium chloride salt as a white crystalline material. The enantiomeric excess was found to be 97.1% (HPLC) and the D-content on chiral center 99.0% ($^1$H-NMR). Note: Other samples synthesized using exactly the same process were analyzed by $^2$H-NMR and the deuterium content by $^2$H-NMR indicated about 3 deuteriums on the molecule (one on the chiral center, DCl and one deuterium on the exchangeable NH position).

Chiral HPLC method: Samples were run on a 250 mm×4.6 mm, 3 μm Chiralpak IC or equivalent. The mobile phase was an isocratic elution system with 70:30 (v/v) Hexane/IPA. Flow rate was 1.0 mL/min; run time, 30 min; and detector wavelength, 225 nm.

$^1$H-NMR method: About 5 to 10 mg sample were dissolved in DMSO D6 for $^1$H-NMR analysis. $^1$H-NMR analysis was performed using a Bruker Avance 300 MHz or higher spectrometer.

Characterization by X-Ray Powder Diffraction

An X-ray powder diffractogram of the crystalline DCl salt of deuterium-enriched (R)-pioglitazone is provided in FIG. 1A. X-ray powder diffraction data were collected using a D8 Advance diffractometer using Cu Kai radiation (1.54056 Å) with a germanium monochromator at room temperature (e.g., about 21° C. to about 23° C.). Detector scans on a solid state LynxEye detector were performed using 0.0160 per step, with a scan speed of 5 sec/step. Samples were analyzed in 8 mm long glass capillary tubes with a 0.3 mm outer diameter. Tabulated characteristics of the X-ray powder diffractogram in FIG. 1A are provided below in Table 4, which lists diffraction angle 2θ, inter-planar distances d, and relative intensity (expressed as a percentage with respect to the most intense peak).

TABLE 4

X-ray Powder Diffractogram Data of the Crystalline Deuterium Chloride Salt of Deuterium-Enriched (R)-Pioglitazone

| 2θ (°) | d value (Å) | Intensity (%) |
|---|---|---|
| 8.6 | 10.27 | 18 |
| 8.8 | 10.07 | 17 |
| 12.8 | 6.93 | 22 |
| 12.9 | 6.87 | 26 |
| 15.9 | 5.59 | 4 |

TABLE 4-continued

X-ray Powder Diffractogram Data of the Crystalline Deuterium Chloride Salt of Deuterium-Enriched (R)-Pioglitazone

| 2θ (°) | d value (Å) | Intensity (%) |
|---|---|---|
| 18.7 | 4.73 | 18 |
| 18.9 | 4.70 | 16 |
| 19.7 | 4.51 | 18 |
| 20.0 | 4.45 | 34 |
| 20.8 | 4.26 | 56 |
| 21.2 | 4.19 | 13 |
| 22.1 | 4.02 | 8 |
| 22.8 | 3.89 | 100 |
| 23.7 | 3.75 | 3 |
| 25.6 | 3.47 | 5 |
| 26.0 | 3.43 | 20 |
| 26.7 | 3.34 | 9 |
| 27.3 | 3.26 | 6 |
| 28.1 | 3.18 | 12 |
| 29.8 | 3.00 | 12 |
| 31.3 | 2.86 | 21 |
| 32.1 | 2.79 | 10 |
| 32.3 | 2.77 | 5 |
| 33.4 | 2.68 | 3 |
| 33.6 | 2.66 | 3 |
| 34.4 | 2.60 | 4 |
| 36.0 | 2.50 | 3 |

Figure 1B:
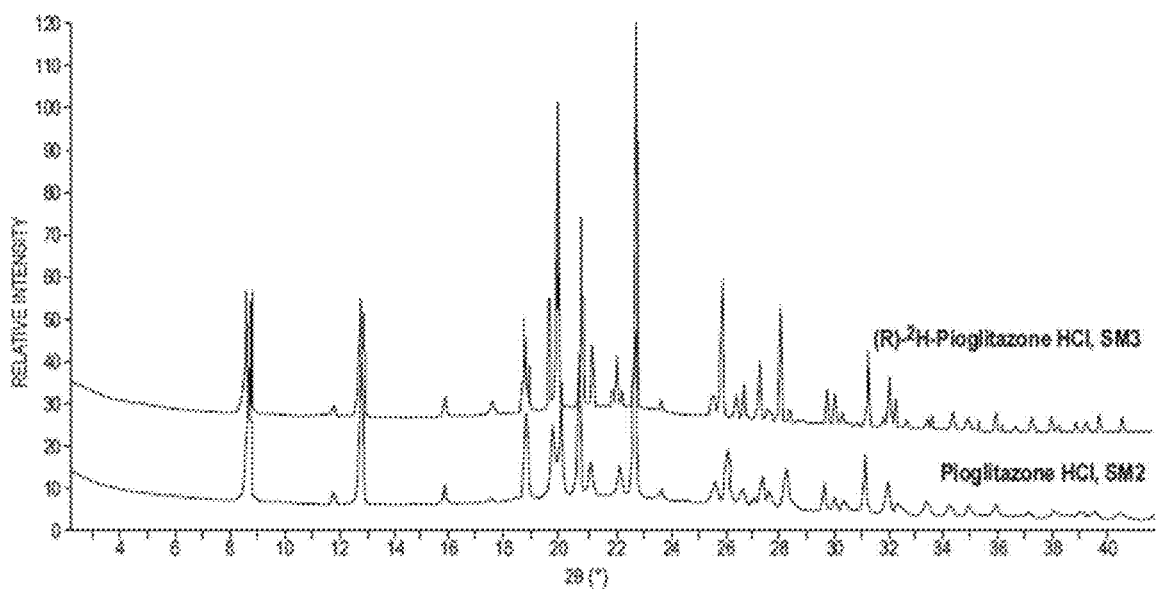
FIG. 1B is an exemplary X-ray powder diffraction (XRPD) pattern of the crystalline hydrogen chloride salt of deuterium-enriched (R)-pioglitazone overlaid with an X-ray powder diffraction (XRPD) pattern of the crystalline hydrogen chloride salt of pioglitazone.

As shown in FIG. 1B, it can be noted that the X-ray powder diffraction (XRPD) pattern of (R)-2H-pioglitazone HCl salt (upper trace) is not identical with the XRPD pattern of pioglitazone HCl salt (lower trace), in particular showing doubling of several peaks.

Characterization by Single Crystal X-Ray Diffraction

Single crystals of the crystalline DCl salt of deuterium-enriched (R)-pioglitazone were analyzed by single crystal X-ray diffraction. Data were collected using a Nonius Kappa-CCD instrument at 296 K.

Data reduction was performed using HKL Scalepack (Otwinowski & Minor 1997) and cell parameters were obtained using Denzo and Scalepak (Otwinowski & Minor, 1997).

The crystal structure of the crystalline DCl salt of deuterium-enriched (R)-pioglitazone was solved using direct methods by SHELXT-2014/7 (Sheldrick, G. M., 2015a). The structure was refined by least square full matrix refinement using SHELXL-2014/7 (Sheldrick, G. M., 2015b). All H-atoms connected to the C were included from the geometry and kept with fixed thermal parameters. The H atoms involved in the hydrogen bond network were found in the Fourier difference map and were refined isotropically.

The unit cell parameters of the crystalline DCl salt of deuterium-enriched (R)-pioglitazone and the data collection and structure refinement methods are shown in Table 5.

TABLE 5

Unit Cell Parameters and Data Collection and Structure Refinement Methods for the Crystalline DCl Salt of Deuterium-Enriched (R)-Pioglitazone

| Empirical formula | $C_{19}H_{18}D_3N_2O_3S^+$ $Cl^-$ |
|---|---|
| formula weight | 395.9 |
| T [K] | 296 (2) K |
| λ [Å] | 0.71073 Å |
| Crystal system | Monoclinic |
| Space group | $P2_1$ |
| Unit cell dimensions | |
| a [Å] | 10.1319 (9) |
| b [Å] | 9.4067 (9) |
| c [Å] | 10.3231 (6) |

TABLE 5-continued

Unit Cell Parameters and Data Collection and Structure Refinement Methods for the Crystalline DCl Salt of Deuterium-Enriched (R)-Pioglitazone

| | |
|---|---|
| β [°] | 94.397 (3) |
| V [Å$^3$] | 980.98 (14) |
| Z | 2 |
| D$_c$ [g/cm$^3$] | 1.330 |
| μ [mm$^{-1}$] | 0.322 |
| F(000) | 412 |
| Crystal size [mm$^3$] | 0.45 × 0.25 × 0.18 |
| θ range for data collection [°] | 2.7 → 32.6 |
| Reflections collected | 11335 |
| Independent reflections | 6943 [R$_{int}$ = 0.0191] |
| Complet. to θ = 25.242° [%] | 98.7 |
| Absorption correction | Integration |
| Max. and min. transmission | 0.958 and 0.877 |
| Data/restraints/parameters | 6943/1/248 |
| Goodness-of-fit on F$^2$ | 1.030 |
| R$_1$, wR$_2$ [I > 2σ(I)] | 0.0371, 0.0962 |
| R$_1$, wR$_2$ (all data) | 0.0444, 0.1034 |
| Flack parameter | −0.013 (18) |
| Absolute configuration | R |
| Largest diff. peak and hole [e/Å$^3$] | 0.191 and −0.252 |

Characterization by Optical Microscopy

Figure 2:
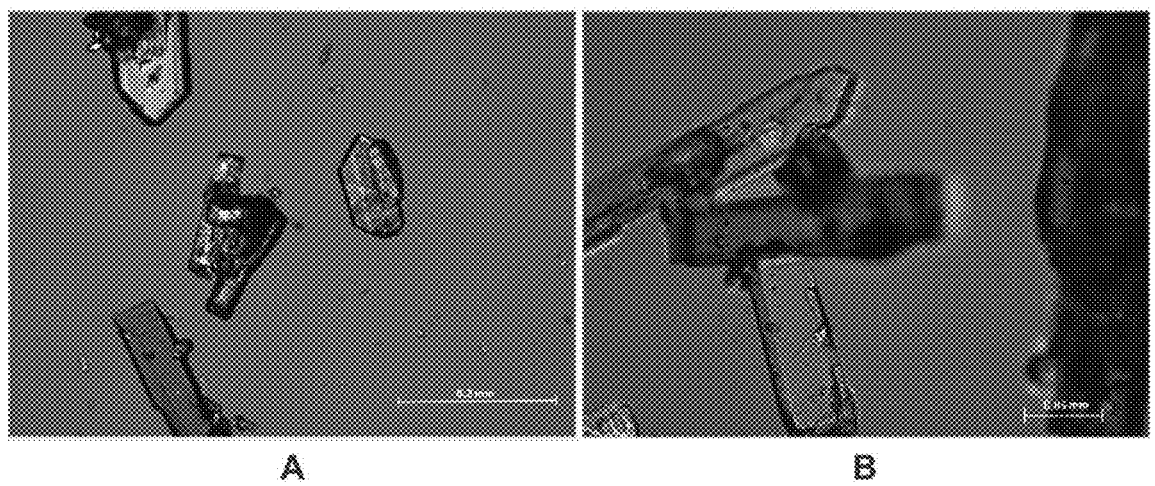
FIG. 2 is an exemplary optical micrograph of the crystalline deuterium chloride salt of deuterium-enriched (R)-pioglitazone at (A) 10× magnification and (B) 20× magnification.

An optical micrograph of the crystalline DCl salt of deuterium-enriched (R)-pioglitazone is shown in FIG. 2. Optical micrographs were obtained using a Leica DM 2500M optical microscope. The crystals exhibited both hexagonal and rod-like crystal shapes.

Characterization by Differential Scanning Calorimetry

A differential scanning calorimetry (DSC) curve of the crystalline DCl salt of deuterium-enriched (R)-pioglitazone is provided in FIG. 3. DSC data were collected using a heat flux DSC3+ STARe system. Samples (~2 mg) were sealed in standard 40 μL aluminum pans, pin-holed, and heated in the DSC from 25° C. to 300° C., at a heating rate of 10° C./min. During measurement, dry N$_2$ gas at a flow rate of 50 mL/min was used to purge the sample chamber. The DSC curve displayed an endothermic event, corresponding to the melting of the crystalline DCl salt form of deuterium-enriched (R)-pioglitazone, with onset and peak values at about 191° C. and about 202° C., respectively.

Figure 4A:
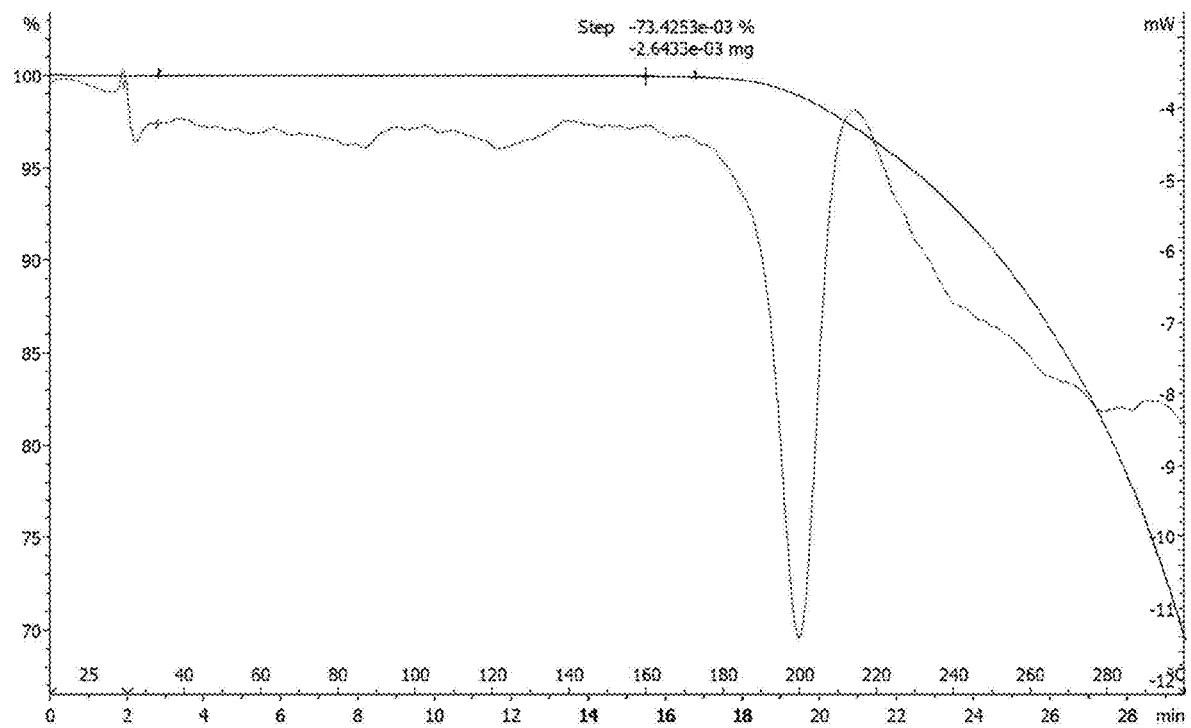
FIG. 4A is an exemplary thermogravimetric analysis (TGA) curve of the crystalline deuterium chloride salt of deuterium-enriched (R)-pioglitazone.
Figure 4B:
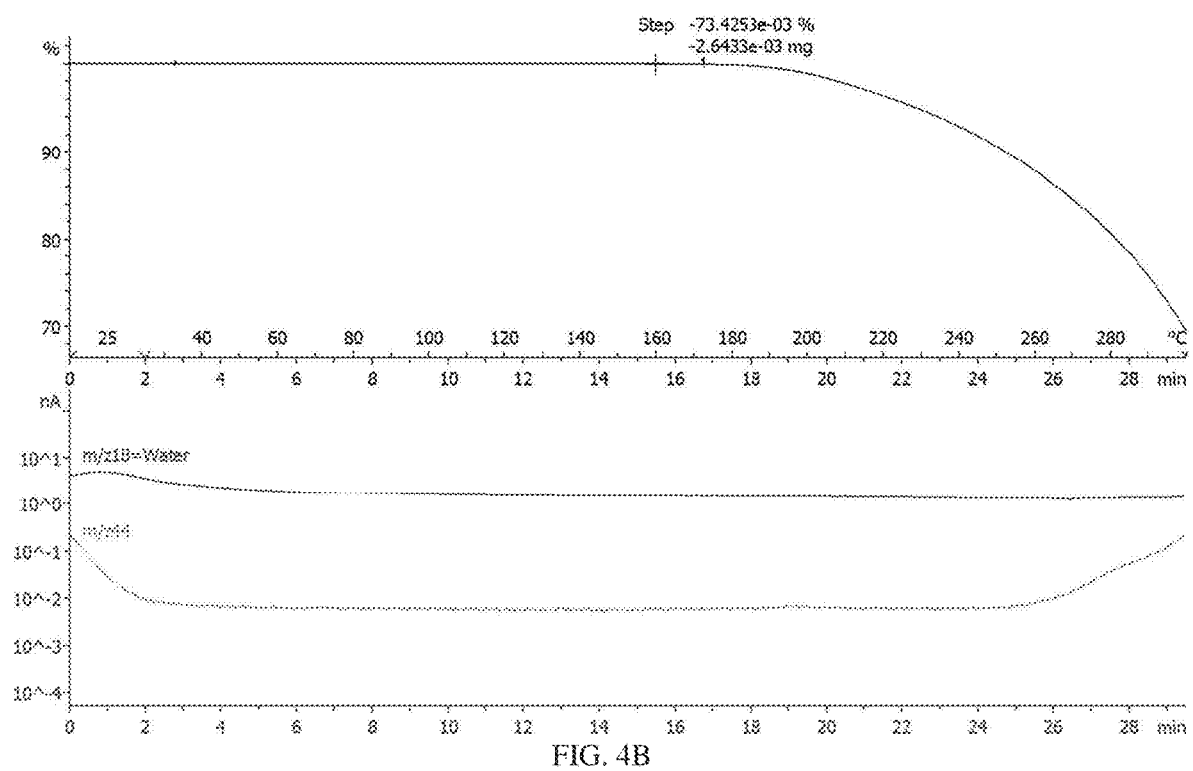
FIG. 4B is an exemplary thermal gravimetric mass spectrometry (TGMS) plot of the crystalline deuterium chloride salt of deuterium-enriched (R)-pioglitazone.

Characterization by Thermogravimetric Analysis and Thermal Gravimetric Mass Spectrometry Thermogravimetric analysis (TGA) and thermal gravimetric mass spectrometry (TGMS) data for the crystalline DCl salt form of deuterium-enriched (R)-pioglitazone are provided in FIG. 4A and FIG. 4B, respectively. TGA data were collected using a TGA/DSC 3+ STARe system (Mettler-Toledo GmbH, Switzerland) calibrated for temperature using samples of indium and aluminum. Samples were weighed in to 100 μL aluminum crucibles and sealed. The seals were pin-holed, and the crucibles heated from 25° C. to 300° C. at a heating rate of 10° C. During measurement dry N$_2$ gas was used for purging. The volatiles produced by the TGA samples upon heating were analyzed by an Omnistar GSD 301 T2 (Pfeiffer Vacuum GmbH, Germany) mass spectrometer. The TGA and TGMS data showed that the crystalline DCl salt form of deuterium-enriched (R)-pioglitazone is anhydrous, with a mass loss of 0.07% between 40° C. and 170° C., and that thermal decomposition occurred above 190° C.

Figure 5:
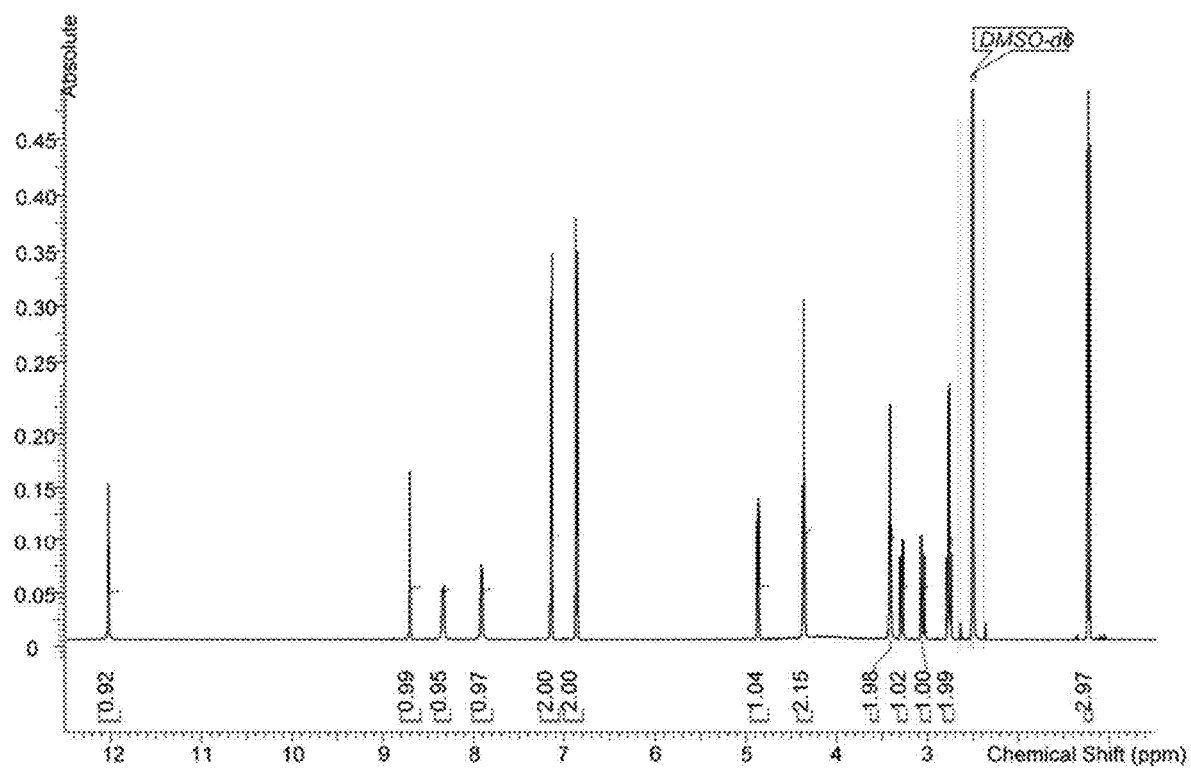
FIG. 5 is an exemplary proton nuclear magnetic resonance ($^1$H-NMR) spectrum of the crystalline deuterium chloride salt of deuterium-enriched (R)-pioglitazone.

Characterization by NMR Spectroscopy $^1$H-NMR spectra for the crystalline DCl salt form of deuterium-enriched (R)-pioglitazone were collected at room temperature on a 500 MHz Bruker instrument using standard pulse sequences. Samples of the crystalline DCl salt form of deuterium-enriched (R)-pioglitazone were dissolved in DMSO-d$_6$. The $^1$H-NMR chemical shifts (ppm) for the crystalline DCl salt form of deuterium-enriched (R)-pioglitazone were as follows: 1.25 (t, 3H), 2.79 (q, 2H), 3.07 (d, 1H), 3.30-3.34 (m, 1H), 3.43 (t, 2H), 4.38 (t, 2H), 6.83-6.93 (m, 2H), 7.11-7.24 (m, 2H), 7.94 (br d, 1H), 8.37 (br d, 1H), 8.66-8.80 (m, 1H), 12.04 (s, 1H). A representative $^1$H-NMR spectrum of the crystalline DCl salt is provided in FIG. 5.

Example 3: Preparation and Characterization of the Crystalline HCl Salt Form of Deuterium-Enriched (R)-Pioglitazone 2.2 g of deuterium-enriched (R)-pioglitazone L-dibenzoyl tartrate salt (as prepared in Example 1), 11 mL of MeOH and 37% HCl in H$_2$O (0.308 g, 2.9 equiv.) was heated to 40° C. Subsequently, 40 mL of ethyl acetate was added to the slightly turbid solution and the mixture was allowed to cool to 20° C. After stirring for 2 hours at this temperature the HCl salt form of deuterium-enriched (R)-pioglitazone was isolated by filtration (P-4 Büchner funnel with a filter paper) and washed thoroughly with ethyl acetate (5×20 mL). After drying overnight at 50° C. in vacuo 1.1 g (Y=90.9%) of white crystalline material was obtained. The enantiomeric excess was found to be 97.2% (HPLC) and the D-content >98% ($^1$H-NMR). Note: Deuterium content by $^2$H-NMR indicated about 1 deuterium on the molecule which was confirmed to be on the chiral center by $^1$H-NMR.

Chiral HPLC method: Samples were run on a 250 mm×4.6 mm, 3 μm Chiralpak IC or equivalent. The mobile phase was an isocratic elution system with 70:30 (v/v) Hexane/IPA. Flow rate was 1.0 mL/min; run time, 30 min; and detector wavelength, 225 nm.

$^1$H-NMR method: About 5 to 10 mg sample were dissolved in DMSO D6 for $^1$H-NMR analysis. $^1$H-NMR analysis was performed using a Bruker Avance 300 MHz or higher spectrometer.

Characterization by Powder X-Ray Diffraction

An X-ray powder diffractogram of the crystalline HCl salt form of deuterium-enriched (R)-pioglitazone is provided in FIG. 6. X-ray powder diffraction data were collected as described in Example 2. Tabulated characteristics of the X-ray powder diffractogram in FIG. 6 are provided below in Table 6, which lists diffraction angle 2θ, inter-planar distances d, and relative intensity (expressed as a percentage with respect to the most intense peak).

TABLE 6

X-ray Powder Diffractogram Data of the Crystalline HCl Salt Form of Deuterium-Enriched (R)-Pioglitazone

| 2θ (°) | d value (Å) | Intensity (%) |
|---|---|---|
| 8.6 | 10.27 | 32 |
| 8.8 | 10.08 | 31 |
| 12.8 | 6.93 | 30 |
| 12.9 | 6.87 | 27 |
| 15.9 | 5.59 | 6 |
| 18.7 | 4.73 | 25 |
| 18.9 | 4.70 | 12 |
| 19.7 | 4.51 | 29 |
| 20.0 | 4.45 | 80 |
| 20.8 | 4.26 | 50 |
| 21.2 | 4.19 | 18 |
| 22.1 | 4.02 | 14 |
| 22.8 | 3.89 | 100 |
| 23.7 | 3.75 | 4 |
| 25.6 | 3.47 | 6 |
| 26.0 | 3.43 | 36 |

TABLE 6-continued

X-ray Powder Diffractogram Data of the Crystalline
HCl Salt Form of Deuterium-Enriched (R)-Pioglitazone

| 2θ (°) | d value (Å) | Intensity (%) |
|---|---|---|
| 26.7 | 3.34 | 9 |
| 27.3 | 3.26 | 15 |
| 28.1 | 3.17 | 30 |
| 29.8 | 3.00 | 9 |
| 31.3 | 2.86 | 19 |
| 32.1 | 2.79 | 13 |
| 32.3 | 2.77 | 7 |
| 33.4 | 2.68 | 3 |
| 33.6 | 2.66 | 3 |
| 34.4 | 2.61 | 5 |
| 36.0 | 2.50 | 5 |

Characterization by Optical Microscopy

Figure 7:
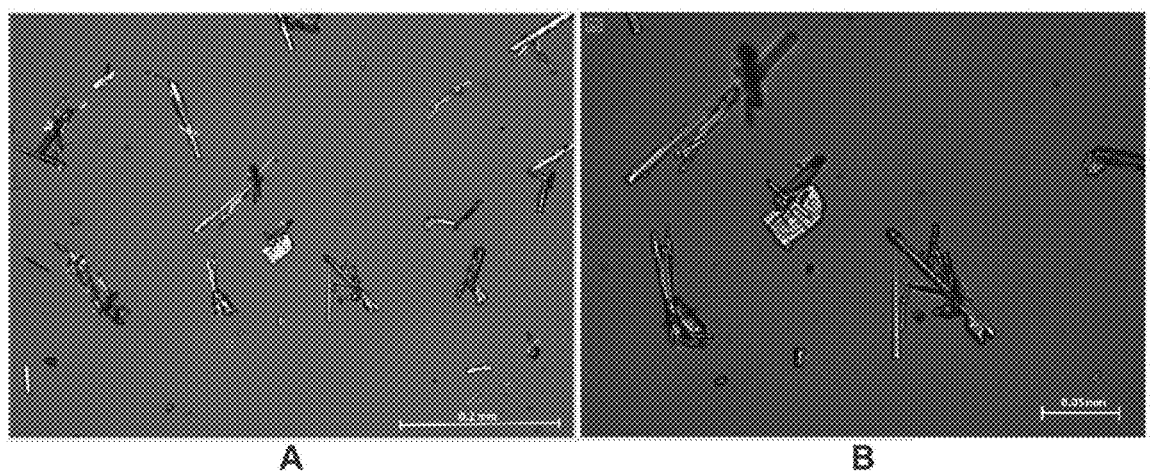
FIG. 7 is an exemplary optical micrograph of the crystalline hydrochloride salt of deuterium-enriched (R)-pioglitazone at (A) 10× magnification and (B) 20× magnification.

An optical micrograph of the crystalline HCl salt of deuterium-enriched (R)-pioglitazone is shown in FIG. 7. Optical micrographs were obtained using a Leica DM 2500M optical microscope. The crystals exhibited both hexagonal and rod-like crystal shapes.

Characterization by Differential Scanning Calorimetry

A differential scanning calorimetry (DSC) curve of the crystalline HCl salt form of deuterium-enriched (R)-pioglitazone is provided in FIG. 8. DSC data were collected using the method described in Example 2. The DSC curve displayed an endothermic event, corresponding to the melting of the crystalline HCl salt form of deuterium-enriched (R)-pioglitazone, with onset and peak values at about 190° C. and about 200° C., respectively.

Figure 9A:
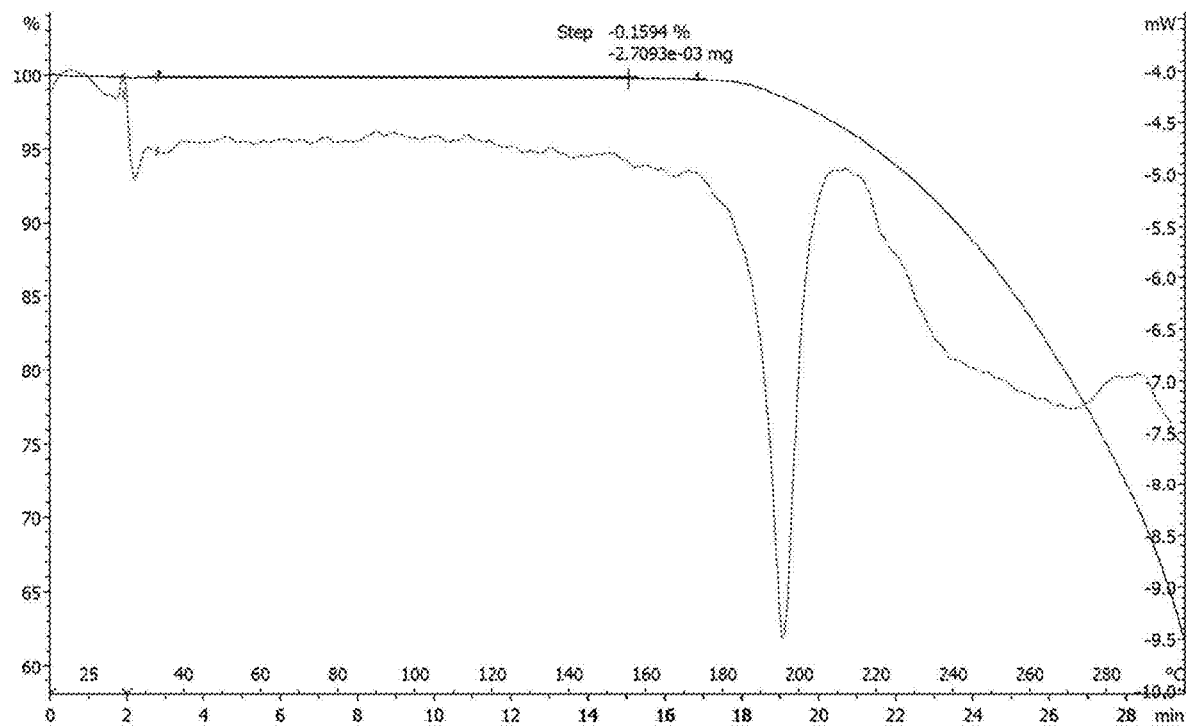
FIG. 9A is an exemplary thermogravimetric analysis (TGA) curve of the crystalline hydrochloride salt of deuterium-enriched (R)-pioglitazone.
Figure 9B:
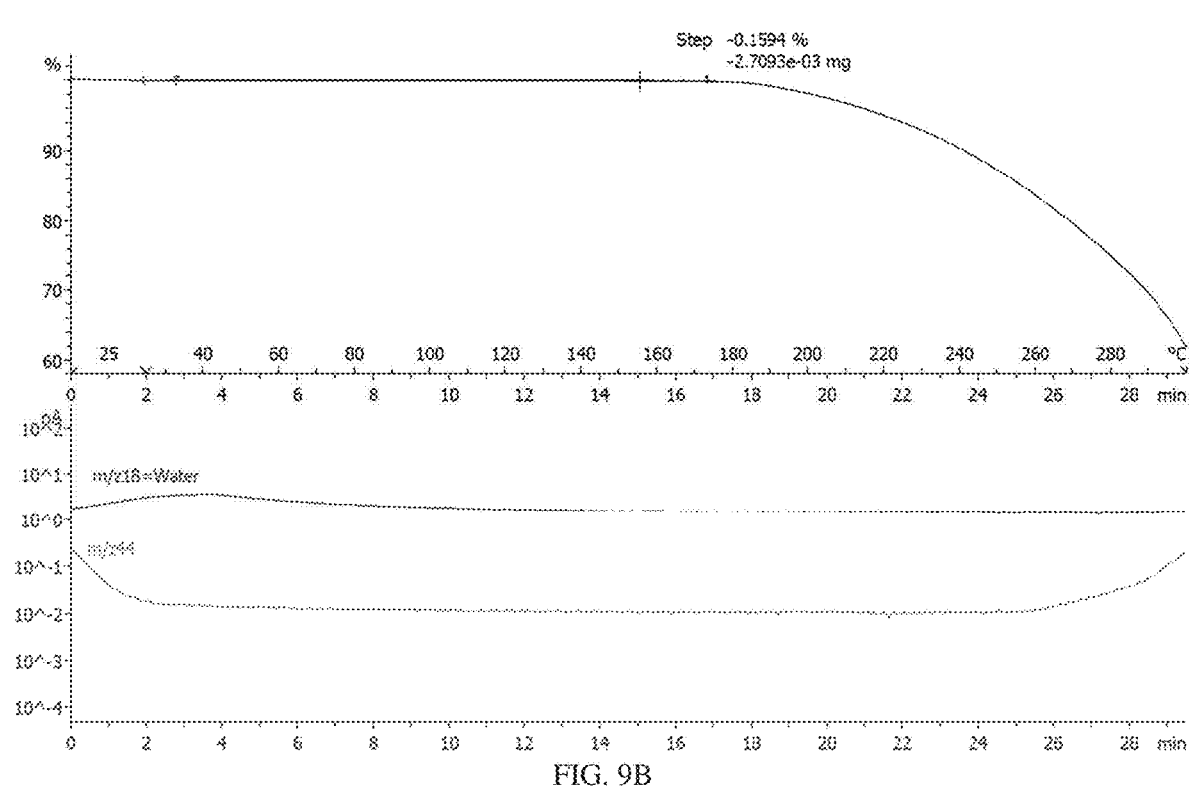
FIG. 9B is an exemplary thermal gravimetric mass spectrometry (TGMS) plot of the crystalline hydrochloride salt of deuterium-enriched (R)-pioglitazone.

Characterization by Thermogravimetric Analysis Simultaneous Difference Thermal Analysis and Thermal Gravimetric Mass Spectrometry Thermogravimetric analysis (TGA) and thermal gravimetric mass spectrometry (TGMS) data for the crystalline HCl salt form of deuterium-enriched (R)-pioglitazone are provided in FIG. 9A and FIG. 9B, respectively. TGA and TGMS data were collected using the methods described in Example 2. The TGA and TGMS data showed that the crystalline HCl salt form of deuterium-enriched (R)-pioglitazone is anhydrous, with a mass loss of 0.2% between 40° C. and 180° C., and that thermal decomposition occurred above 220° C.

Figure 10:
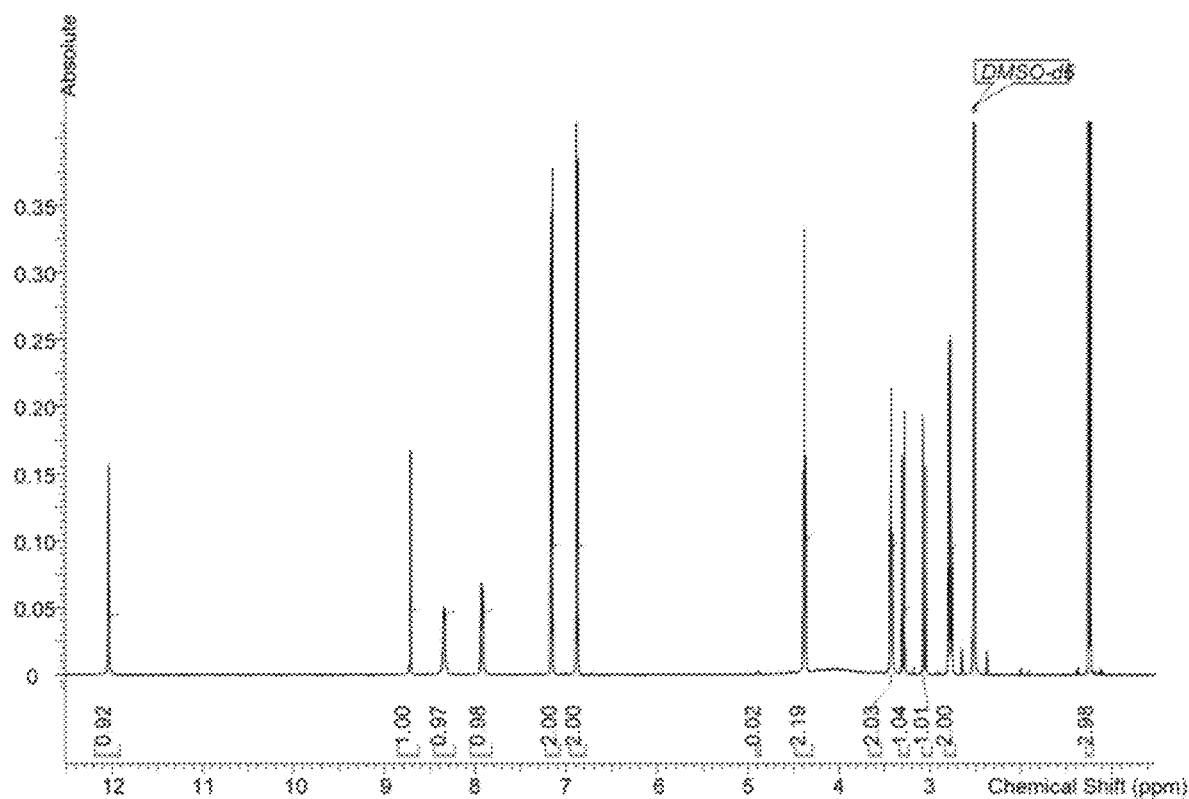
FIG. 10 is an exemplary $^1$H-NMR spectrum of the crystalline hydrochloride salt of deuterium-enriched (R)-pioglitazone.

Characterization by NMR Spectroscopy $^1$H-NMR spectra for the crystalline HCl salt form of deuterium-enriched (R)-pioglitazone were collected as described in Example 2. Samples of the crystalline HCl salt form of deuterium-enriched (R)-pioglitazone were dissolved in DMSO-$d_6$. The $^1$H-NMR chemical shifts (ppm) for the crystalline HCl salt form of deuterium-enriched (R)-pioglitazone were as follows: 1.25 (t, 3H), 2.79 (q, 2H), 3.07 (d, 1H), 3.30-3.34 (m, 1H), 3.43 (t, 2H), 4.38 (t, 2H), 6.83-6.93 (m, 2H), 7.11-7.24 (m, 2H), 7.94 (br d, 1H), 8.37 (br d, 1H), 8.66-8.80 (m, 1H), 12.04 (s, 1H). A representative $^1$H-NMR spectrum of the crystalline HCl salt is provided in FIG. 10.

Example 4: Preparation and Characterization of the Crystalline Free-Base Form of Deuterium-Enriched (R)-Pioglitazone The free-base form of deuterium-enriched R-Pioglitazone was prepared by incubating the crystalline DCl salt of deuterium-enriched R-Pioglitazone from Example 2 in water at 50° C. for 2 weeks.

The enantiomeric access, as measured by HPLC, was determined to be 43%. The HPLC method used is described in Examples 2 and 3.

The D-content on the chiral center, as measured by $^1$H-NMR, was determined to be about 66%. The $^1$H-NMR method used is described in Examples 2 and 3.

Characterization by Powder X-Ray Diffraction

Figure 11:
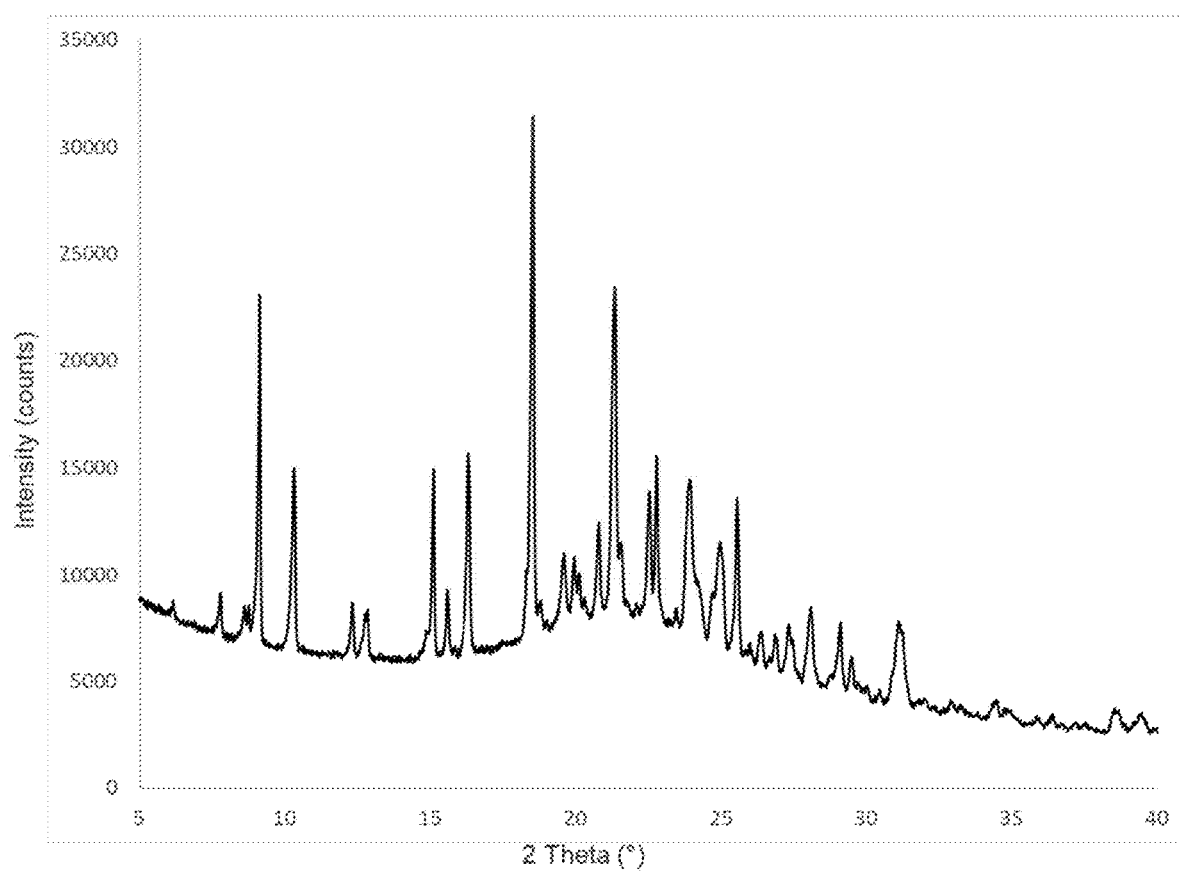
FIG. 11 an exemplary X-ray powder diffraction (XRPD) pattern of the crystalline free base of deuterium-enriched (R)-pioglitazone.

An X-ray powder diffractogram of the crystalline free-base form of deuterium-enriched R-pioglitazone is provided in FIG. 11. X-ray powder diffraction data were collected as described in Example 2. Representative diffraction peaks from the X-ray powder diffractogram in FIG. 11, expressed in terms diffraction angle (2θ), are provided below in Table 7.

TABLE 7

X-ray Powder Diffractogram Data of the Crystalline
Free-Base Form of Deuterium-Enriched R-Pioglitazone

| 2θ (°) |
|---|
| 6.2 |
| 7.8 |
| 8.6 |
| 8.8 |
| 9.2 |
| 10.3 |
| 12.4 |
| 12.9 |
| 15.1 |
| 15.6 |
| 16.3 |
| 18.6 |
| 19.6 |
| 20.0 |
| 20.8 |
| 21.4 |
| 22.6 |
| 22.8 |
| 24.0 |
| 25.0 |
| 25.6 |
| 26.4 |
| 26.9 |
| 27.4 |
| 28.1 |
| 29.1 |
| 29.5 |
| 31.1 |

Characterization by Differential Scanning Calorimetry

Figure 12:
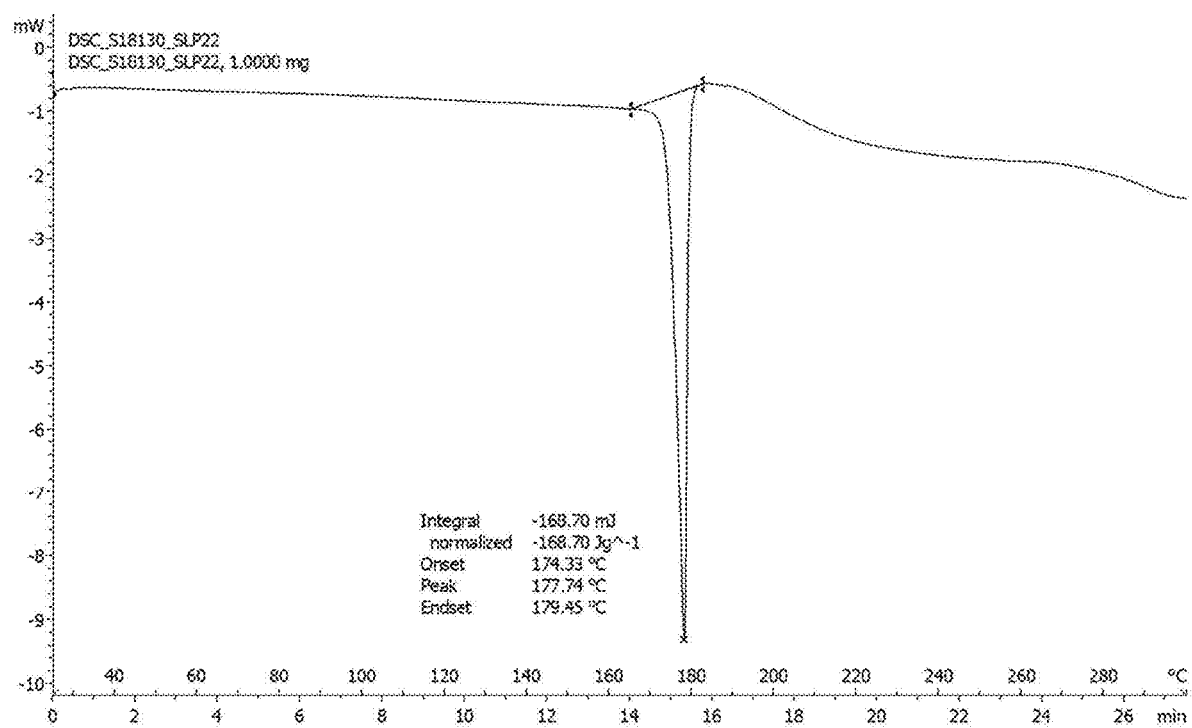
FIG. 12 is an exemplary differential scanning calorimetry (DSC) curve of the crystalline free-base form of deuterium-enriched (R)-pioglitazone.

A differential scanning calorimetry (DSC) curve of the crystalline free-base form of deuterium-enriched R-pioglitazone is provided in FIG. 12. DSC data were collected using the method described in Example 2. The DSC curve displayed an endothermic event, corresponding to the melting of the crystalline free-base form of deuterium-enriched R-pioglitazone, with onset and peak values at about 174° C. and about 178° C., respectively.

Figure 13A:
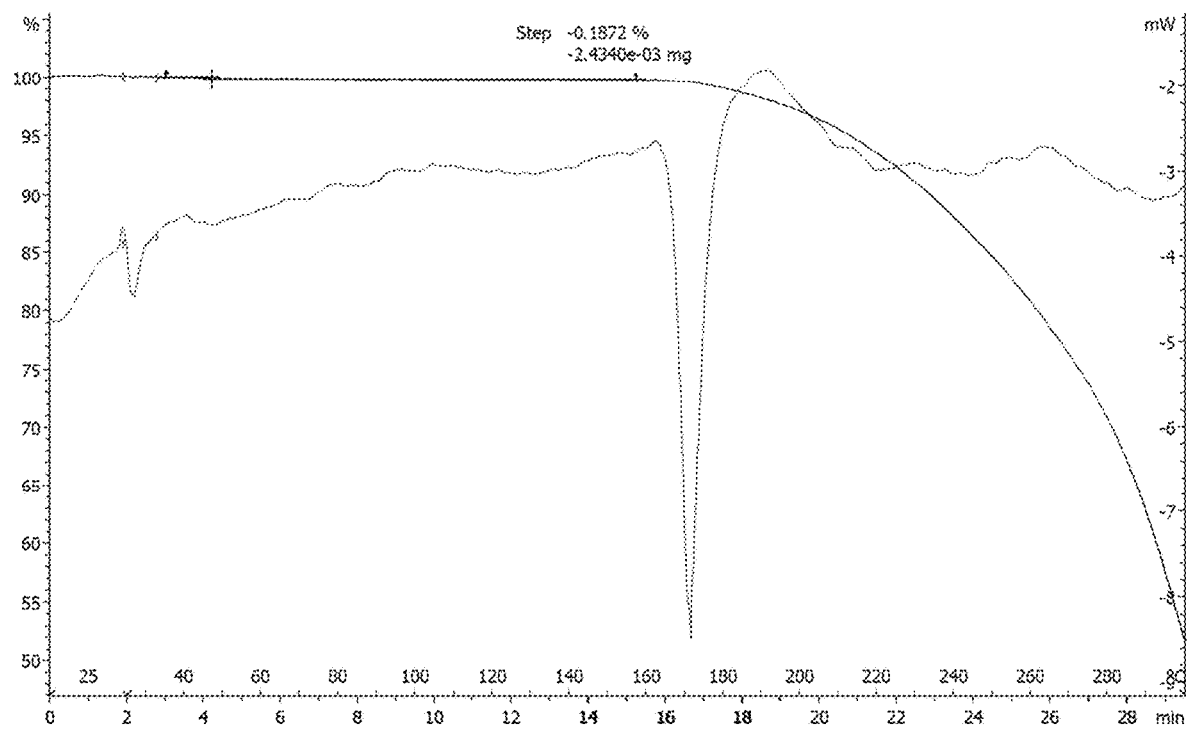
FIG. 13A is an exemplary thermogravimetric analysis (TGA) curve of the crystalline free-base form of deuterium-enriched (R)-pioglitazone.
Figure 13B:
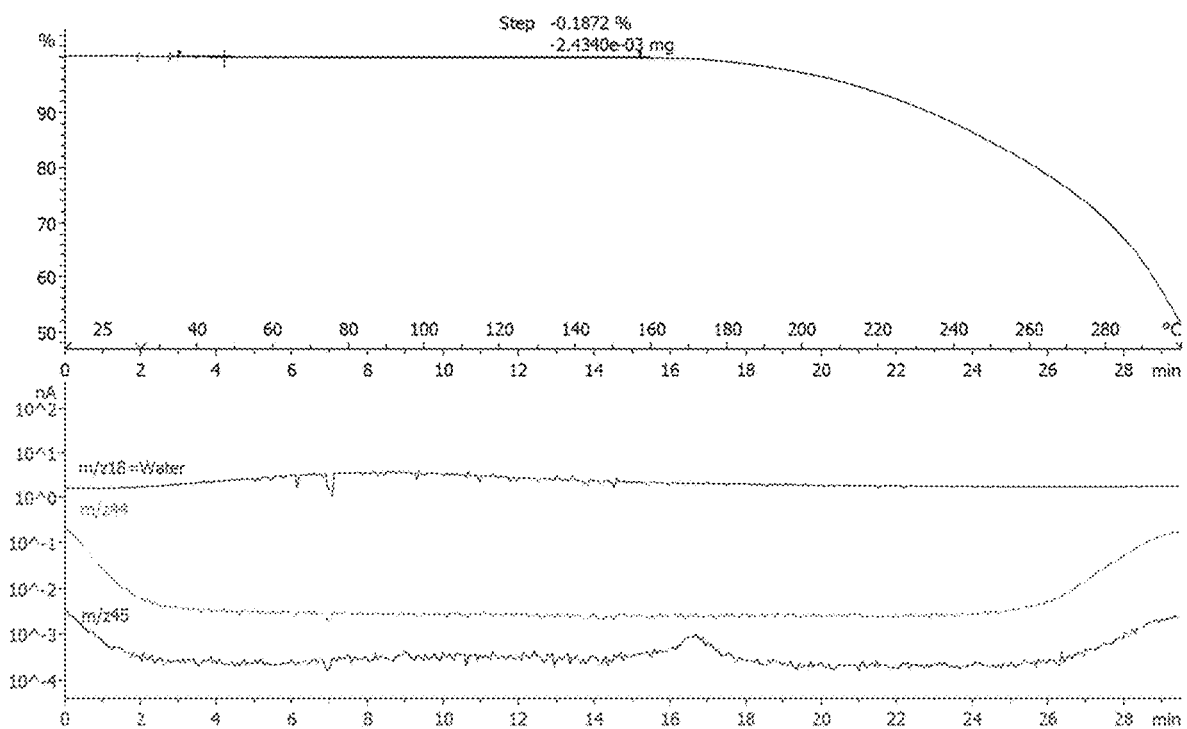
FIG. 13B is an exemplary thermal gravimetric mass spectrometry (TGMS) plot of the crystalline free-base form of deuterium-enriched (R)-pioglitazone.

Characterization by Thermogravimetric Analysis Simultaneous Difference Thermal Analysis and Thermal Gravimetric Mass Spectrometry Thermogravimetric analysis (TGA) and thermal gravimetric mass spectrometry (TGMS) data for crystalline free-base form of deuterium-enriched R-pioglitazone are provided in FIG. 13A and FIG. 13B, respectively. TGA and TGMS data were collected using the methods described in Example 2. The TGA and TGMS data showed that the crystalline free-base form of deuterium-enriched R-pioglitazone is anhydrous, with thermal decomposition occurring above 160° C.

Characterization by NMR Spectroscopy $^1$H-NMR spectra for the crystalline free-base form of deuterium-enriched (R)-pioglitazone were collected as described in Example 2. Samples of the crystalline free-base form of deuterium-enriched (R)-pioglitazone were dissolved in DMSO-$d_6$. The $^1$H-NMR chemical shifts (ppm) for the crystalline free-base form of deuterium-enriched (R)-pioglitazone were as follows: 1.20 (t, 3H), 2.56-2.70 (m, 2H), 3.06 (d, 1H), 3.17 (t, 2H), 3.24-3.33 (m, 1H), 4.32 (t, 2H), 4.88 (dd, 1H), 6.80-6.93 (m, 2H), 7.15 (m, 2H), 7.35 (br d, 1H), 7.66 (br d, 1H), 8.41 (s, 1H), 12.03 (s, 1H).

Example 5: Solubility of the Crystalline DCl and HCl Salts of Deuterium-Enriched (R)-Pioglitazone in Various Organic Solvents Crystalline DCl salt of deuterium-enriched (R)-pioglitazone: suspensions of the crystalline material in ethanol, methanol, 3-pentanone, 2-propanol, DMSO, tert-butyl methyl ether, N,N-dimethylformamide, ethyl acetate, acetone, water, tetrahydrofuran, and chloroform were prepared and incubated for 24 hours at room temperature (about 21° C. to about 23° C.). Aliquots of the mother liquor were then taken from each suspension and analyzed by HPLC to determine the concentration of deuterium-enriched (R)-pioglitazone in the different solvents. HPLC methods are shown in Table 8.

TABLE 8

HPLC Method

HPLC system:

| | |
|---|---|
| Instrument: | Agilent 1200 |
| Detector 1: | DAD set at 265 nm |
| Detector 2: | HP1100 LC/MSD in positive scan mode |

HPLC conditions:

| | | | |
|---|---|---|---|
| Auto sampler temp.: | 15° C. | | |
| Column: | Waters Sunfire C18 (100 × 4.6 mm; 3.5 µm) | | |
| Column temp.: | 35° C. | | |
| Flow cell: | 10 mm path | | |
| Gradient: | Mobile phase A: | 10 mM ammonium acetate | |
| | Mobile phase B: | acetonitrile LC/MS grade | |
| Flow: | 1.0 mL/min | | |
| Gradient: | Time [min]: | Eluent A: | Eluent B: |
| | 0 | 90% | 10% |
| | 1 | 90% | 10% |
| | 6 | 10% | 90% |
| | 9 | 10% | 90% |
| | 12 | 90% | 10% |
| Run time: | 13 min | | |

Sample:

| | |
|---|---|
| Concentration: | ca. 1 mg/mL |
| Solvent: | 10 mM ammonium acetate:acetonitrile (50:50 v/v) |
| Injection volume: | 5 µL |
| Retention time: | 6.2 min |

Crystalline HCl salt of deuterium-enriched (R)-pioglitazone: Qualitative testing: (i) About 5 mg of the crystalline HCl salt was added to 1 mL of each solvent (DMSO, N,N-dimethylformamide, methanol, water, ethanol, tetrahydrofuran, ethyl acetate, toluene, and dichloromethane); (ii) the resulting mixtures were then stirred at ambient temperature (about 21° C. to about 23° C.) for 5-10 minutes; (iii) the mixtures were then visually inspected to determine if the crystalline HCl salt had completely dissolved; (iv) if the crystalline HCl salt had not completely dissolved more solvent was added until complete dissolution occurred. Quantitative testing: (i) 100 mg of crystalline HCl salt was added to 4 vol. of each solvent (0.4 mL) dimethylformamide, methanol and DMSO; (ii) the resulting mixtures were then stirred at ambient temperature (about 20° C. to about 25° C.) for 5-10 minutes; (iii) the mixtures were then visually inspected to determine if the crystalline HCl salt had completely dissolved; (iv) if the crystalline HCl salt had not completely dissolved more solvent was added until complete dissolution occurred.

The solubilities were then calculated using the total quantity of crystalline HCl salt and solvent used for each solvent.

Solubility data for the crystalline DCl and HCl salts of deuterium-enriched (R)-pioglitazone in various organic solvents are shown in Table 9 and Table 10, respectively.

TABLE 9

Solubility of the Crystalline DCl Salt Form of Deuterium-Enriched (R)-Pioglitazone in Various Organic Solvents

| Solvent | Solubility (mg/mL) |
|---|---|
| DMSO | 225.9 |
| N,N-dimethylformamide | 46.4 |
| Methanol | 45.0 |
| Water | 7.7 |
| Ethanol | 4.4 |
| Chloroform | 2.0 |
| Tetrahydrofuran | 1.8 |
| 3-pentanone | 0.5 |
| 2-propanol | 0.5 |
| Acetone | 0.5 |
| tert-butyl methyl ether | <0.1 |
| Ethyl acetate | <0.1 |

TABLE 10

Solubility of the Crystalline HCl Salt Form of Deuterium-Enriched (R)-Pioglitazone in Various Organic Solvents

| Solvent | Solubility (mg/mL) |
|---|---|
| DMSO | >50 |
| N,N-dimethylformamide | ~50 |
| Methanol | ~50 |
| Ethyl acetate | <5-10 |
| Ethanol | <5-10 |
| Toluene | <5-10 |
| Tetrahydrofuran | <5-10 |
| Dichloromethane | <5-10 |
| Water | <5-10 |

Example 6: Effect of pH on the Solubility of the Crystalline DCl and HCl Salts of Deuterium-Enriched (R)-Pioglitazone and Crystalline Pioglitazone HCl The pH-dependent solubility profiles of the crystalline DCl salt form of deuterium-enriched (R)-pioglitazone, and crystalline pioglitazone HCl were determined at room temperature (about 21° C. to about 23° C.) in the pH range of 0.3-7.6. For the crystalline HCl salt form of deuterium-enriched (R)-pioglitazone, the pH-dependent solubility profile was measured at room temperature (about 21° C. to about 23° C.) in the pH range of 0.3-3.5.

For the crystalline DCl salt form of deuterium-enriched pioglitazone, the pH-dependent solubility profile was measured at room temperature (about 21° C. to about 23° C.) in the pH range of 0.7-3.5.

Suspensions of the three crystalline forms were prepared in water or USP buffer solutions. The pH of the suspensions was adjusted through the addition of 0.1 M HCl or 0.1 M NaOH. For the preparation of suspensions with a pH of 0.5 or lower, the pH was adjusted using 1 M HCL.

The suspensions were then allowed to equilibrate at room temperature (about 21° C. to about 23° C.) for 48 hours. After equilibration the solid phases were separated from the liquid phases by centrifugation, subsequently dried and then analyzed by XRPD. The concentration of deuterium-enriched (R)-pioglitazone or pioglitazone in the liquid phases (mother liquors) was determined by HPLC (see HPLC method described in Example 5).

Figure 14:
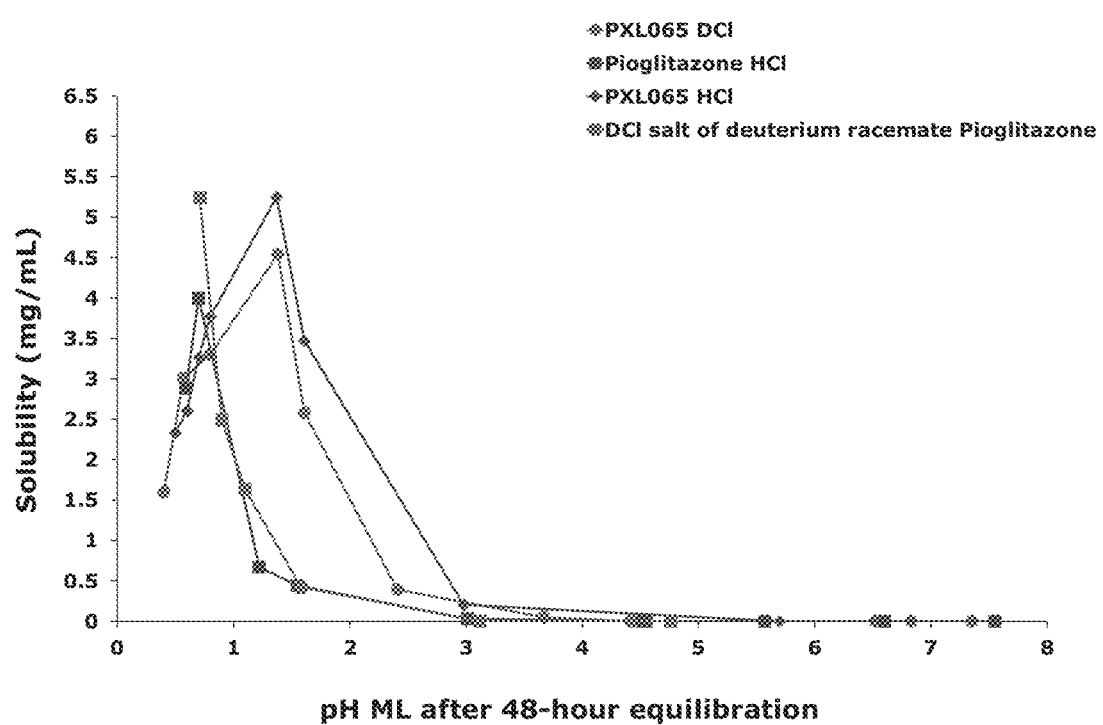
FIG. 14 is an overlay of pH-dependent solubility profiles of the crystalline DCl and HCl salts of deuterium-enriched (R)-pioglitazone, of the crystalline DCl salt of deuterium-enriched pioglitazone and of the crystalline HCl salt of pioglitazone.

The solubility data collected for the four crystalline forms is shown in Table 11 and an overlay of the pH-dependent solubility profiles of the crystalline DCl and HCl salt forms of deuterium-enriched (R)-pioglitazone, crystalline DCl salt form of deuterium-enriched pioglitazone and crystalline pioglitazone HCl is presented in FIG. 14.

The crystalline DCl and HCl salts of deuterium-enriched (R)-pioglitazone exhibited a similar pH-dependent solubility profile: the solubility was higher at very low pH values—0.4-1.4, the maximum solubility was reach at pH 1.4 (4.54 mg/mL and 5.25 mg/mL for the DCl and HCl salts, respectively). A decrease in solubility was observed by increasing the pH thereafter. At pH 1.6, the solubility decreased to 2.58 mg/mL for the crystalline DCl salt of deuterium-enriched (R)-pioglitazone, and to 3.47 mg/mL for the crystalline HCl salt of deuterium-enriched (R)-pioglitazone. At pH values of 2.4 and 3.0 the observed decrease in solubility was more significant (0.39 mg/mL and 0.20 mg/mL for the DCl and HCl salts, respectively). It was observed that both salts were practically insoluble above pH 4.

In contrast, the maximum solubility for pioglitazone HCl was determined to be 4.00 mg/mL at pH 0.7. The solubility of pioglitazone HCl was found to decrease as the pH of the solution was increased: pH 0.6-2.88 mg/mL and pH 1.2-0.67 mg/mL. Further decreases in solubility were observed at higher pH values. Pioglitazone HCl was observed to be practically insoluble at pH values of greater than 3. The crystalline DCl salt form of deuterium-enriched pioglitazone presents behavior similar to that of pioglitazone HCl.

For all four solid forms, in the pH range 0.3-0.8 there was no observed change in the solid form after equilibration. In the pH range 1.2-1.4, all three solid forms were observed to either partially or completely covert to the respective free-base form.

TABLE 11 pH-Dependent Solubility Data for the Crystalline DCl and HCl Salt Forms of Deuterium-Enriched (R)-Pioglitazone and Crystalline Pioglitazone HCl

| Solvent | Initial Suspension pH | pH After Acid/Base Addition | Filtered Mother Liquor pH | Solubility (mg/mL) | Solid Phase After Equilibration |
|---|---|---|---|---|---|
| Deuterium-Enriched (R)-Pioglitazone DCl Salt | | | | | |
| Water | — | 0.3 | 0.4 | 1.60 | deuterium-enriched (R)-pioglitazone DCl salt |
| Water | 1.4 | 0.5 | 0.6 | 3.01 | deuterium-enriched (R)-pioglitazone DCl salt |
| Water | — | 0.8 | 0.8 | 3.30 | deuterium-enriched (R)-pioglitazone DCl salt |
| Water | 1.5 | 1.2 | 1.4 | 4.54 | deuterium-enriched (R)-pioglitazone free base |
| Water | 1.4 | 1.5 | 1.6 | 2.58 | deuterium-enriched (R)-pioglitazone free base |
| Water | 1.4 | 2.5 | 2.4 | 0.39 | deuterium-enriched (R)-pioglitazone free base |
| Water | 1.6 | 3.1 | 3.7 | 0.05 | deuterium-enriched (R)-pioglitazone free base |
| Acetate Buffer | 2.0 | 4.5 | 4.4 | <0.05 | deuterium-enriched (R)-pioglitazone free base |
| Water | 1.5 | 5.5 | 6.8 | <0.05 | deuterium-enriched (R)-pioglitazone free base |
| Phosphate Buffer | 2.3 | 6.6 | 6.5 | <0.05 | deuterium-enriched (R)-pioglitazone |
| Phosphate Buffer | 6.5 | 7.6 | 7.4 | <0.05 | deuterium-enriched (R)-pioglitazone free base |
| Deuterium-Enriched (R)-Pioglitazone HCl Salt | | | | | |
| Water | 1.6 | 0.3 | 0.5 | 2.33$^a$ | deuterium-enriched (R)-pioglitazone HCl salt |
| Water | 1.5 | 0.3 | 0.5 | 2.33$^a$ | deuterium-enriched (R)-pioglitazone HCl salt |
| Water | 1.5 | 0.5 | 0.5 | 2.33$^a$ | deuterium-enriched (R)-pioglitazone HCl salt |
| Water | 1.6 | 0.5 | 0.6 | 2.60 | deuterium-enriched (R)-pioglitazone HCl salt |
| Water | — | 0.3 | 0.7 | 3.27$^a$ | deuterium-enriched (R)-pioglitazone HCl salt |
| Water | 1.4 | 0.5 | 0.7 | 3.27$^a$ | deuterium-enriched (R)-pioglitazone HCl salt |
| Water | — | 0.8 | 0.8 | 3.77$^a$ | deuterium-enriched (R)-pioglitazone HCl salt |
| Water | 1.4 | 0.8 | 0.8 | 3.77$^a$ | deuterium-enriched (R)-pioglitazone HCl salt |
| Water | 1.5 | 0.8 | 0.8 | 3.77$^a$ | deuterium-enriched (R)-pioglitazone HCl salt |

TABLE 11-continued pH-Dependent Solubility Data for the Crystalline DCl and HCl Salt Forms
of Deuterium-Enriched (R)-Pioglitazone and Crystalline Pioglitazone HCl

| Solvent | Initial Suspension pH | pH After Acid/Base Addition | Filtered Mother Liquor pH | Solubility (mg/mL) | Solid Phase After Equilibration |
|---|---|---|---|---|---|
| Water | 1.3 | 1.3 | 1.4 | 5.25 | deuterium-enriched (R)-pioglitazone HCl salt |
| Water | 1.5 | 1.5 | 1.6 | 3.47 | deuterium-enriched (R)-pioglitazone HCl salt |
| Water | 1.6 | 2.5 | 3.0 | 0.20 | deuterium-enriched (R)-pioglitazone HCl salt |
| Water | 1.6 | 3.6 | 5.7 | <0.05 | deuterium-enriched (R)-pioglitazone HCl salt |
| Pioglitazone HCl Salt | | | | | |
| Water | 1.3 | 0.5 | 0.6 | 2.88 | pioglitazone HCl salt |
| Water | — | 0.3 | 0.7 | 4.00[a] | pioglitazone HCl salt |
| Water | — | 0.8 | 0.7 | 4.00[a] | pioglitazone HCl salt |
| Water | 1.2 | 1.2 | 1.2 | 0.67 | pioglitazone HCl salt + pioglitazone free base |
| Water | 1.3 | 1.5 | 1.6 | 0.44 | pioglitazone HCl salt + pioglitazone free base |
| Water | 1.2 | 2.5 | 3.0 | 0.03 | pioglitazone free base |
| Water | 1.2 | 3.5 | 4.6 | <0.03 | pioglitazone free base |
| Acetate Buffer | 1.8 | 4.5 | 4.5 | <0.03 | pioglitazone free base |
| Water | 1.2 | 5.5 | 5.6 | <0.03 | pioglitazone free base |
| Phosphate Buffer | 2.0 | 6.6 | 6.6 | <0.03 | pioglitazone free base |
| Phosphate Buffer | 6.0 | 7.6 | 7.6 | <0.03 | pioglitazone free base |
| Crystalline DCl salt form of deuterium-enriched pioglitazone | | | | | |
| Water | 1.4-1.5 | 0.7 | 0.7 | 5.24 | deuterium-enriched pioglitazone HCl salt |
| Water | 1.4-1.5 | 1.0 | 0.9 | 2.49 | deuterium-enriched pioglitazone HCl salt + deuterium-enriched pioglitazone free base |
| Water | 1.4-1.5 | 1.2 | 1.1 | 1.63 | deuterium-enriched pioglitazone HCl salt + deuterium-enriched pioglitazone free base |
| Water | 1.4-1.5 | 1.5 | 1.6 | 0.42 | deuterium enriched pioglitazone free base |
| Water | 1.4-1.5- | 3.0 | 3.1 | <0.03 | deuterium-enriched pioglitazone free base |
| Water | 1.4-1.5 | 4.5 | 4.8 | <0.03 | deuterium-enriched pioglitazone free base |

[a]Averaged solubility value.

Example 7: Determination of Particle Size Distribution for the Crystalline DCl and HCl Salts of Deuterium-Enriched (R)-Pioglitazone The particle size distribution of the crystalline DCl and HCl salts of deuterium-enriched (R)-pioglitazone prepared using the methods described in Examples 2 and 3, respectively, were measured using a laser diffraction method. Samples of the crystalline DCl and HCl salts (100 mg-200 mg) were wetted and dispersed in 30 mL of heptane. The experimental details are given in Table 12.

Representative particle size distributions for the HCl (before and after milling) and DCl salts are given in Table 13.

The crystalline HCl salt was milled using a fluidized air jet mill system or equivalent.

TABLE 12

Particle Size Distribution Analysis—Laser Diffraction Method

| Materials and Equipment Used | |
|---|---|
| Equipment: | Beckman Coulter LS 13320 |
| Dispersant: | Heptane and dispersant like Span 80 (2 drops) if needed |
| Operational Parameters: | |
| Optical model: | Fraunhofer approximation |
| Refractive index of dispersant: | 1.39 |
| Measures: | |
| Time of measure: | 10-30 seconds |
| Speed agitation: | 50 ± 2% |
| Time measure of the background: | 30 seconds |
| Obscuration range: | 1-25% |

TABLE 13

Representative Particle Size Distributions of the Crystalline
DCl and HCl Salts of Deuterium-Enriched (R)-Pioglitazone

| Crystalline DCl salt | D10 = 64 μm |  |
|---|---|---|
|  | D50 = 211 μm |  |
|  | D90 = 662 μm |  |
| Crystalline HCl salt | Before Milling | After Milling |
|  | D10 = 97 μm | D10 = 27 μm |
|  | D50 = 323 μm | D50 = 139 μm |
|  | D90 = 792 μm | D90 = 441 μm |

Example 8: A Study to Assess the Impact on Processability of Particle Size Distributions of the Crystalline HCl Salt of Deuterium-Enriched (R)-Pioglitazone (API)

Study was conducted on the 15 mg strength PXL065 tablets

TABLE 14

Particle Size Distribution of 3
Micronized Batches of PXL065 Used in the Study:

|  | d10 | d50 | d90 |
|---|---|---|---|
| Batch #1 with D90 <10 μm | 1 μm | 3 μm | 7 μm |
| Batch #2 with D90 <20 μm | 1 μm | 6 μm | 18 μm |
| Batch #3 with D90 <100 μm | 2 μm | 17 μm | 57 μm |

The tablet includes 15 mg of PXL065, as well as lactose, carmellose calcium, hyprolose, and magnesium stearate. The manufacturing process involves the steps of blending, lubrication, and compression. The particle size distributions of the 3 batches are shown in Table 14.

Flowability

Blend manufactured with API with D90<10 μm is stickier.

Blend Uniformity

TABLE 15

Blend Uniformity

| Batch | Before lubrication | After lubrication |
|---|---|---|
| LF21026 (D90 <10 μm) | 96.2% (SD = 0.6) | 96.2% (SD = 4.5) |
| LF21027 (D90 <20 μm) | 98.4% (SD = 0.7) | 99.6% (SD = 0.5) |
| LF21028 (D90 <100 μm) | 99.1% (SD = 0.8) | 100.1% (SD = 0.5) |

Conclusion

Blend uniformity (shown in Table 15) is compliant (acceptance criteria=90-110%) for all three batches. However, a lower uniformity value is obtained for blend manufactured with API with D90<10 μm. Some losses during manufacture due to stickiness of the API might have occurred.

Mean content uniformity values are <97% for batch LF21026, whereas >97% for batches LF21027 and LF21028, which is consistent with the blend uniformity results.

Extensometric Study

Objective: assess the evolution of tablet hardness (Critical Quality Attributes=CQA) depending on compression force and speed. Tablet hardness is shown in Table 16.

Conclusions

Figure 15:
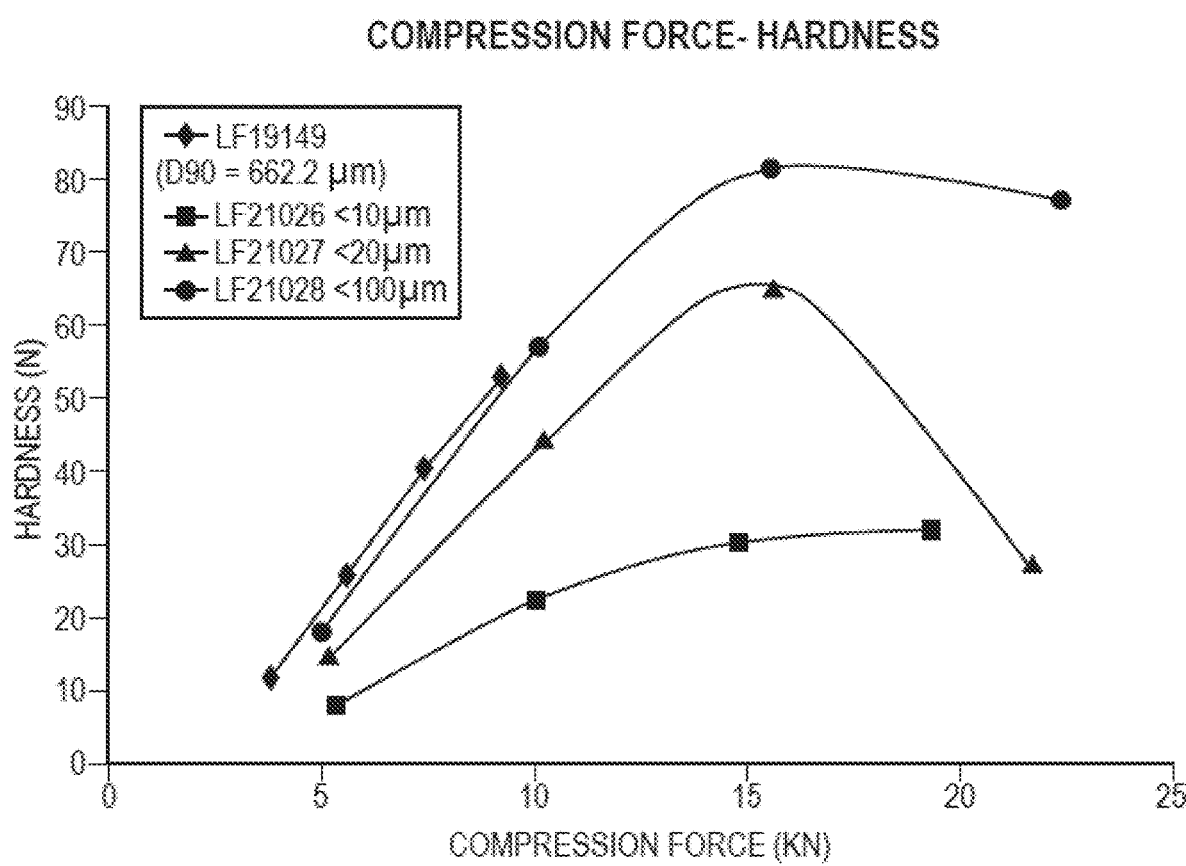
FIG. 15 is an exemplary plot of tablet hardness (N) vs compression force (kN) for active pharmaceutical ingredient (API) batches with varying particle size distribution (PSD) in µm.

As shown in FIG. 15, The lower the PSD of the API, the lower maximal hardness. Tablet hardness is not specified, and is analyzed for information at release.

Figure 16:
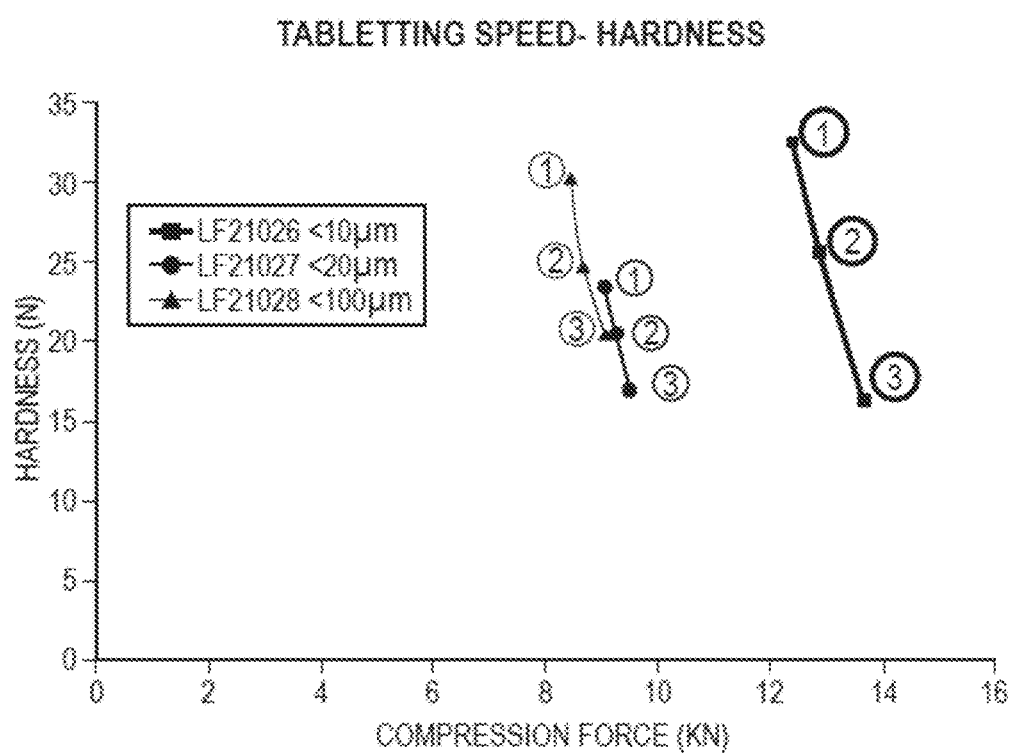
FIG. 16 is an exemplary plot of tablet hardness (N) vs compression force (kN) for API batches with varying particle size distribution (PSD) in µm at different tableting speeds.

As shown in FIG. 16, Tablets produced from blend with API with D90<10 μm are more affected by variation of the tableting speed.

TABLE 16

Tablet Hardness in Newtons

| LF21026 <10 μm |  | LF21027 <20 μm |  | LF21028 <100 μm |  |
|---|---|---|---|---|---|
| Dwell-time (ms) 25 rpm | 41 | Dwell-time (ms) 25 rpm | 39 | Dwell-time (ms) 25 rpm | 38 |
| Dwell-time (ms) 50 rpm | 10 | Dwell-time (ms) 50 rpm | 8 | Dwell-time (ms) 50 rpm | 8 |
| Dwell-time (ms) 100 rpm | 4 | Dwell-time (ms) 100 rpm | 4 | Dwell-time (ms) 100 rpm | 4 |

Example 9. Dog Pharmacokinetic (PK) Study

The objective of the study was to evaluate and compare the pharmacokinetic profiles of the deuterium-enriched (R)- and (S)-enantiomers of pioglitazone (PXL064 and PXL065) to deuterium-enriched pioglitazone (PXL061) after single administration by the oral route (capsule). The 3 Beagle male dogs were fasted before dosing. Then all test drugs were administered by the oral route using API in a capsule. The dosing schedule is shown in Table 17.

TABLE 17

Administration of Test Drugs for Dog PK Study

| Day | Administration | Dose (mg/kg) |
|---|---|---|
| 1 | PXL065 | 5 |
| 4 | PXL064 | 5 |
| 8 | PXL061 | 10 |

Food was given no sooner than one hour after dose administration on the days of treatment. Each administration was separated by a wash-out period of at least 2 days. Blood collection was performed for analysis of plasma concentrations and area under the curve (AUC) of the d-R-pioglitazone, d-S-pioglitazone, h-R-pioglitazone and h-S-pioglitazone quantification at: Predose (just before dosing) and then T(0.25 h, T0.5 h, T1 h, T2 h, T4 h, T8 h, T12 h and T24 h after dosing.

TABLE 18

Mean Plasma PK Parameters of Total Pioglitazone and
Pioglitazone Enantiomers Following Single Oral Administration
of PXL065, PXL064, PXL061 or Pioglitazone in Dogs

|  |  | $T_{max}$ (h) | $C_{max}$ (ng/mL) | $AUC_{0\text{-}24}$ (ng · h/mL) | $T_{1/2}z$ (h) |
|---|---|---|---|---|---|
| PXL065 | Total R-pio | 1 [1-12] | 1330 ± 676 | 5770 ± 2500 | 1.43$^a$ (1.42;1.43) |
|  | Total S-pio | 2 [2-12] | 227 ± 56.7 | 1240 ± 665 | 1.62$^a$ (1.58 ;1.65) |

TABLE 18-continued

Mean Plasma PK Parameters of Total Pioglitazone and Pioglitazone Enantiomers Following Single Oral Administration of PXL065, PXL064, PXL061 or Pioglitazone in Dogs

|  |  | $T_{max}$ (h) | $C_{max}$ (ng/mL) | $AUC_{0-24}$ (ng · h/mL) | $T_{1/2}z$ (h) |
|---|---|---|---|---|---|
|  | Total Pio | 1 [1-12] | 1520 ± 696 | 7000 ± 3150 | 1.46$^a$ (1.45 ;1.56) |
| PXL064 | Total R-pio | 2 [2-2] | 54.0 ± 48.9 | 203 ± 169 | 1.91$^a$ (1.55 ;2.26) |
|  | Total S-pio | 2 [0.5-2] | 538 ± 391 | 1200 ± 852 | 1.75 ± 1.20 |
|  | Total Pio | 2 [1-2] | 588 ± 441 | 1410 ± 1020 | 1.73 ± 0.949 |
| PXL061 | Total R-pio | 1 [0.5-2] | 638 ± 849 | 2650 ± 3690 | 2.78 ± 0.669 |
|  | Total S-pio | 1 [0.25-2] | 683 ± 844 | 2150 ± 3090 | 3.61 ± 1.32 |
|  | Total Pio | 1 [0.25-2] | 1310 ± 1700 | 4800 ± 6780 | 4.03 ± 1.75 |

$AUC_{0-24}$ = area under the plasma concentration-time curve from 0 to 24 hours; Cmax = maximum plasma concentration; pio = pioglitazone; SD = standard deviation; $t_{1/2}z$ = terminal elimination phase half-life; $t_{max}$ = time to maximum plasma concentration
Note:
Table shows exposure to total pioglitazone (sum of deuterated and protonated (R)- and (S)-enantiomers of pioglitazone),
Note:
Unless indicated otherwise, data are presented as mean ± SD values, except for $t_{max}$, which is presented as median [minimum, maximum] values.
Note:
Data are shown for n = 3, unless indicated otherwise.
$^a$Data are presented for n = 2, instead of n = 3. Data are presented as mean (individual animal values).

Figure 17:
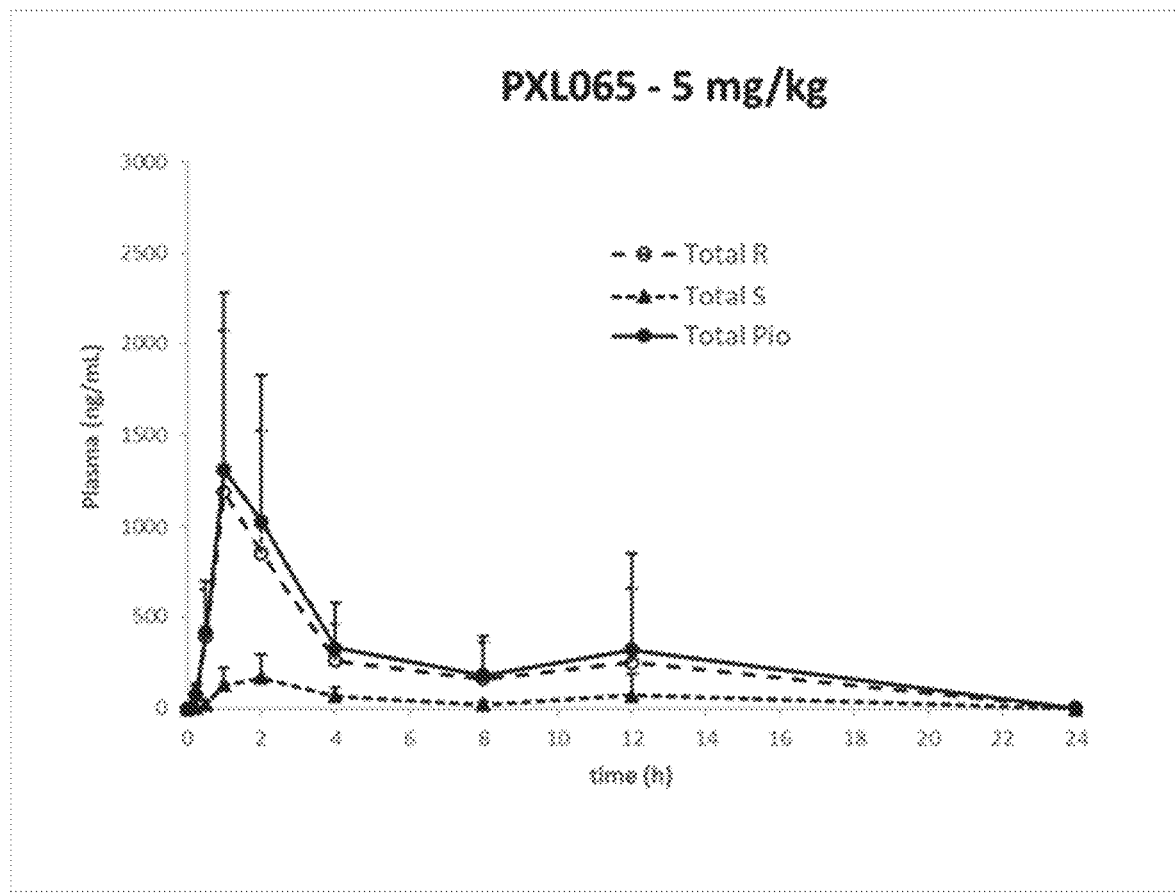
FIG. 17 is an exemplary plot of plasma levels of total pioglitazone (sum of deuterated and protonated (R)- and (S)-enantiomers) over time for doses of PXL065 (deuterium-enriched (R) pioglitazone) in dogs.
Figure 18:
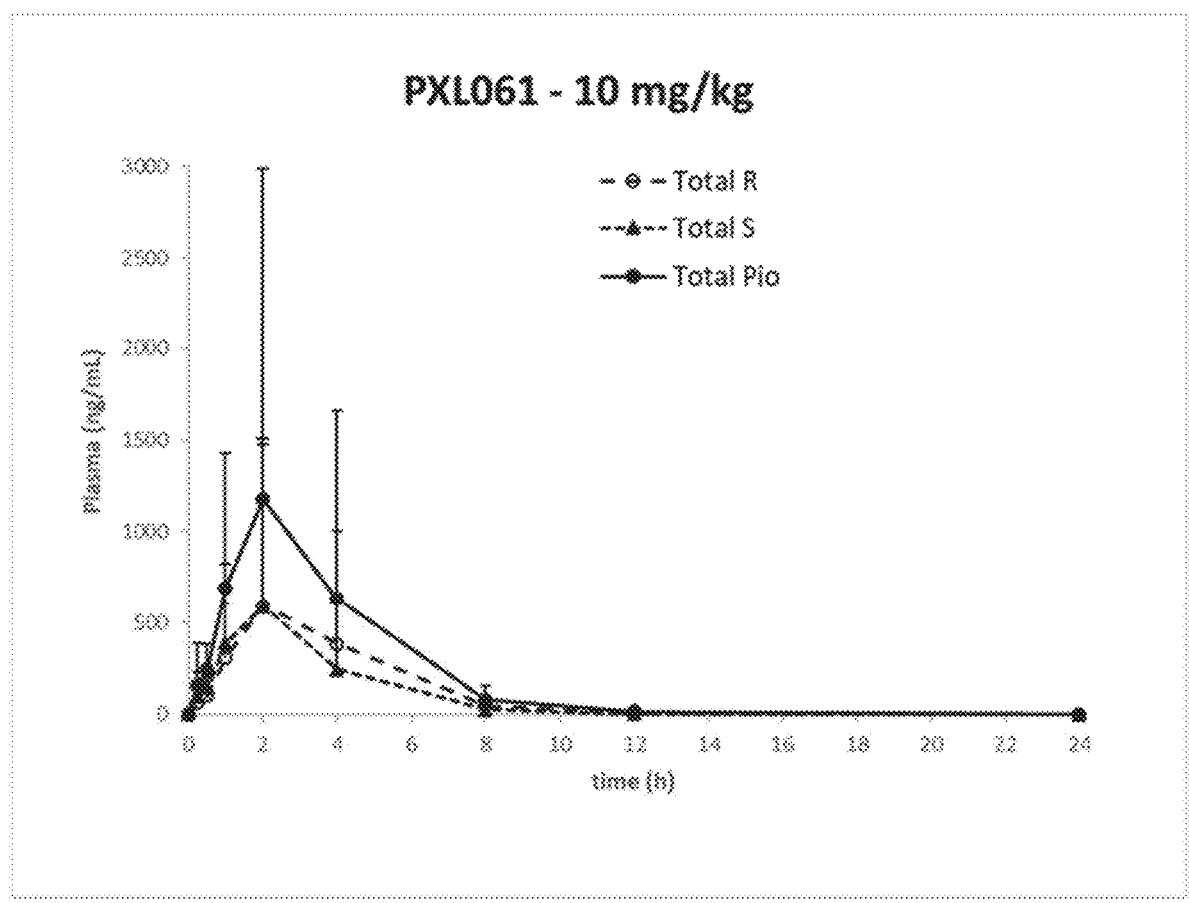
FIG. 18 is an exemplary plot of plasma levels of total pioglitazone (sum of deuterated and protonated (R)- and (S)-enantiomers) over time for doses of PXL061 (deuterium-enriched pioglitazone) in dogs.
Figure 19:
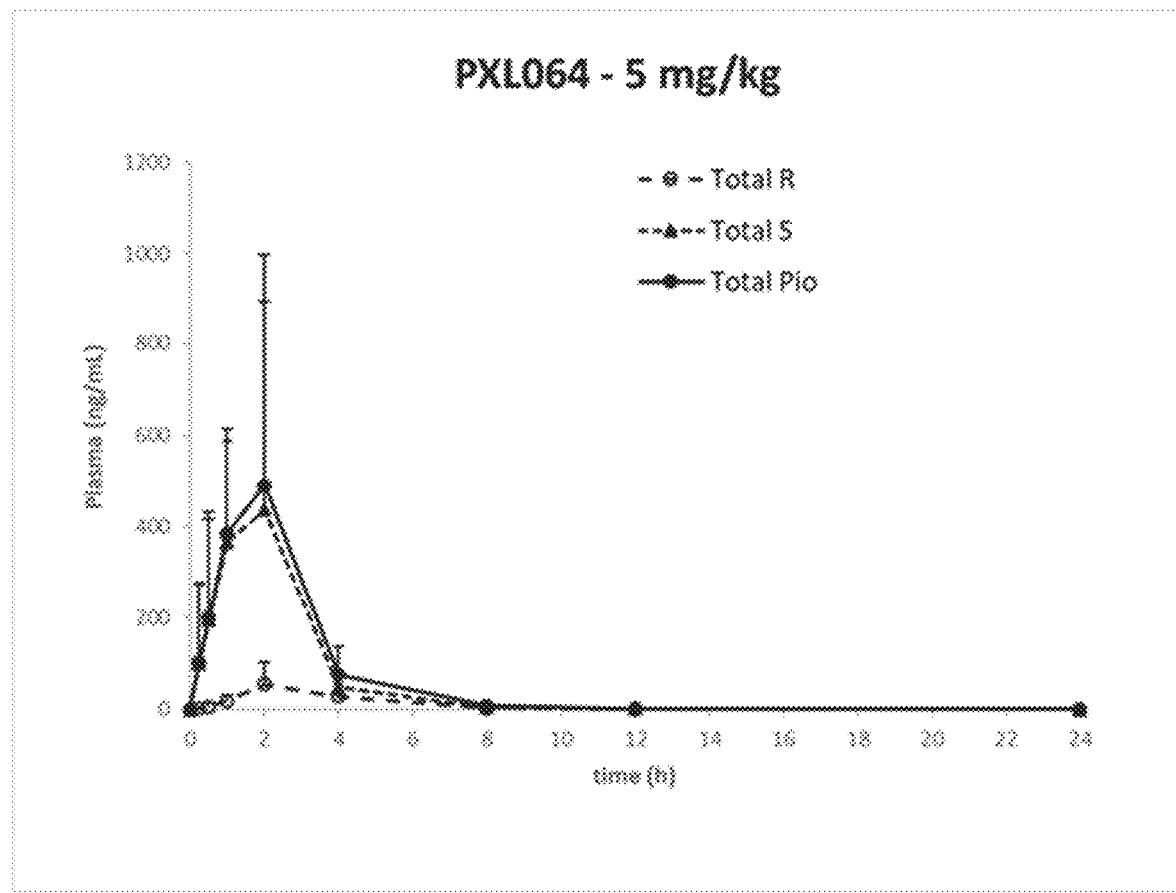
FIG. 19 is an exemplary plot of plasma levels over time of total pioglitazone (sum of deuterated and protonated (R)- and (S)-enantiomers) for doses of PXL064 (deuterium-enriched (S)-pioglitazone) in dogs.

Mean plasma PK parameters are shown in Table 18, and plasma exposures and relative bioavailability are shown in Table 19.
The plasma PK profiles over time are shown in FIGS. 17-19.

TABLE 19

Plasma Exposure ($AUC_{0-24}$) in Dogs of Total Pioglitazone and Relative Bioavailability of Deuterium-enriched (R)-Pioglitazone (PXL065) and Deuterium-enriched (S)-Pioglitazone (PXL064) Compared to Deuterium-Enriched Pioglitazone (PXL061)

| Total Pioglitazone | Animal No. | PXL065 5 mg/kg | PXL064 5 mg/kg | PXL061 10 mg/kg |
|---|---|---|---|---|
| $AUC_{0-24}$ (ng · h/mL) | 1001 | 3904 | 1034 | 12617 |
|  | 1002 | 6904 | 2561 | 684 |
|  | 1003 | 10193 | 625 | 1084 |
|  | Mean | 7000 | 1410 | 4800 |
| Frel vs PXL061 | 1001 | 0.619 | 0.164 | 1 |
|  | 1002 | 20.2 | 7.48 | 1 |
|  | 1003 | 18.8 | 1.15 | 1 |
|  | Geo Mean | 6.17 | 1.12 | 1 |

$AUC_{0-24}$ = area under the plasma concentration-time curve from 0 to 24 hours; Frel = relative oral bioavailability; geo = geometric; total pioglitazone (sum of deuterated and protonated (R)- and (S)-enantiomers of pioglitazone)

The results from these studies support the fact that the increase in total pioglitazone (sum of protonated and deuterated (R)- and (S)-enantiomers) bioavailability seen with PXL065 compared to the deuterium-enriched pioglitazone (PXL061) and not seen with the deuterium-enriched (S)-enantiomer (PXL064), indicates that the enhanced bioavailability of PXL065 is not due to the presence of deuterium.

Example 10. 13-Week Dog Toxicology Study

The objective of the study was to evaluate the potential toxicity and the toxicokinetics of deuterium-enriched (R)-pioglitazone (PXL065) following daily oral administration (capsule) to beagle dogs for 13 weeks in comparison to pioglitazone. Four groups of beagle dogs each comprising three or five animals/sex, were administered 0 (empty capsule), 1.5, 5 or 15 mg/kg/day of PXL065 orally (API in one capsule/day) for 13 weeks; one other group was given 10 mg/kg/day of pioglitazone (API in one capsule/day). Blood was collected for toxicokinetic evaluations at various timepoints (pre-dose, 0.25, 0.5, 1, 2, 4, 8, 12 and 24 hours post-dose) during the dosing period in order to determine the plasma concentrations of d-R-pioglitazone, d-S-pioglitazone, h-R-pioglitazone and h-S-pioglitazone.

Figure 20:
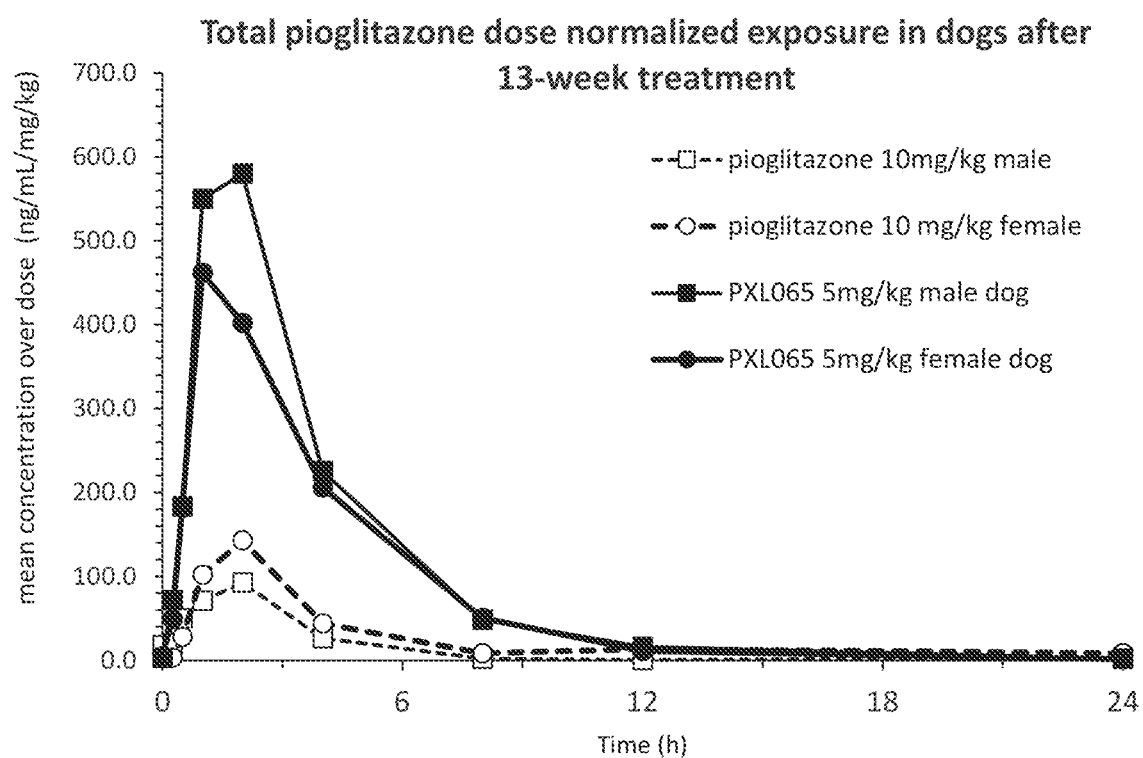
FIG. 20 is an exemplary plot of plasma levels of total pioglitazone (sum of deuterated and protonated (R)- and (S)-enantiomers) over time for doses of pioglitazone and PXL065 in dogs.

The full toxicological evaluation is not presented here, but relative bioavailability data based on total pioglitazone plasma concentrations at day 91 is shown in Table 20 and FIG. 20.

TABLE 20

Mean Total Pioglitazone Exposure in Dogs on Day 91

| Total pioglitazone exposure in dogs | $AUC_{0-24}$, ss (ng · h/mL) | $AUC_{0-24}$, ss dose normalized (ng · h/mL) | Relative Bioavailability (%) |
|---|---|---|---|
| Pioglitazone 10 mg/kg | 2970 (M) 5620 (F) | 297 562 |  |
| PXL065 5 mg/kg | 10900 (M) 8710 (F) | 2180 1762 | 734 310 |

$AUC_{0-24}$, ss = area under the plasma concentration-time curve from 0 to 24 hours at steady state; total pioglitazone (sum of deuterated and protonated (R)- and (S)-enantiomers of pioglitazone)

The results from these studies show that there is an increased bioavailability to total pioglitazone (sum of protonated and deuterated (R)- and (S)-enantiomers) with PXL065 compared to pioglitazone.

Example 11: A Phase Ta Study to Assess the Safety, Tolerability, and Pharmacokinetics of Repeated Doses of the Crystalline HCl Salt of Deuterium-Enriched (R)-Pioglitazone (PXL065) in Healthy Human Subjects Compared to Pioglitazone HCl (Actos®)

Objectives

The primary objective of this study was to assess the safety and tolerability, in healthy subjects, of single oral doses of PXL-065 (7.5 mg, 22.5, and 30 mg as capsules). A secondary objective of this study was to assess the PK of PXL065 in healthy subjects after single doses of PXL065 compared to Actos®, 45 mg, with a specific focus on assessing the exposures to both deuterated and protonated (R)- and (S)-pioglitazone to determine the extent, if any, of interconversion of PXL065 to the protonated (R)- and (S)-enantiomers.

Study Methodology

This study was conducted in two parts. Part 1 utilized an open-label, parallel-group design. Within 21 days of screening, eligible subjects were admitted to the clinical study unit. On Study Day 1, subjects were randomly allocated to receive a single dose of PXL065 22.5 mg (6 subjects) or a single dose of Actos® 45 mg (6 subjects). Doses of study medication were administered at approximately 8 AM on Day 1 in a fasted state. Subjects remained in the clinical unit for 36 hours post-dose administration. Subjects returned to the clinic as out-patients on Days 4 and 7 for follow-up assessments. Following a review of safety and tolerability of PXL065 in Part 1 by a Data Review Committee (DRC) and determination of comparative PK exposure to enantiomers, 6 healthy subjects were enrolled into Part 2.

Part 2 utilized an open-label design in which a single dose of PXL065 7.5 mg was administered in the morning of Day 1 in a fasted state. Subjects remained in the clinical unit for at least 36 hours post-dose and returned to the clinic as out-patients on Days 4 and 7 for follow-up assessments. Following review of safety, tolerability, and PK data from the PXL065 7.5 mg dose group, an additional treatment group (PXL065 30 mg) of 6 healthy subjects was evaluated. Before dosing the additional group, a review of the safety and tolerability from the preceding group was performed by the DRC.

Diagnosis and Criteria for Inclusion

Subjects were healthy adult male or female, 18-40 years of age (inclusive), with a body mass index (BMI) of ≥17 to ≤32 kg/m². Female subjects were not pregnant or breast-feeding.

Test Product, Dose, and Mode of Administration

PXL065, orally administered. Dose=1×7.5 mg capsule, 1×22.5 mg capsule, or 1×30 mg capsule. The PXL065 capsule includes 7.5 mg, 22.5 mg, or 30 mg of PXL065, as well as lactose.

Control Product, Dose, and Mode of Administration

Actos®, orally administered. Dose=1×45 mg, tablet. Actos® was purchased as the branded product. A 45 mg tablet includes 45 mg pioglitazone HCl salt, lactose, carmellose calcium, hyprolose, and magnesium stearate Duration of Treatment In Part 1, a single dose of PXL065 22.5 mg or a single dose of Actos® 45 mg was administered to each subject and they were evaluated for 7 days postdose. In Part 2, a single dose of PXL065 7.5 mg or 30 mg was administered to each subject and they were evaluated for 7 days postdose. The total duration of the study from the time of confinement (Day −1) through the end of study visit is 8 days.

Criteria for Evaluation

Safety: The Investigator evaluated safety using the following assessments: physical examinations, electrocardiograms (ECGs), vital sign measurements, clinical laboratory evaluations, and reported or observed adverse events (AEs). Subjects were monitored for any AEs from the beginning of confinement through the end of the study.

Pharmacokinetics: Plasma PK parameters including, but not limited to $t_{1/2}$, $t_{max}$, $C_{max}$, $AUC_{0-last}$ and $AUC_{0-inf}$ were calculated for the deuterated and protonated forms of (R)- and (S)-pioglitazone.

Statistical Methods

In general, all data were summarized with descriptive statistics (number of subjects, means, standard deviations, minimums, medians, and maximums) for continuous endpoints, and frequency and percentage for categorical endpoints. Within each part of the clinical study, data was presented separately for each cohort and by treatment group within each cohort.

Safety and tolerability: All safety and tolerability data were listed. In the case of continuous variables, descriptive statistics was used to summarize the results and changes from baseline by treatment and time point.

The values of categorical assessments were tabulated. Adverse Events (AEs) were coded according to MedDRA.

Results

Figure 21:
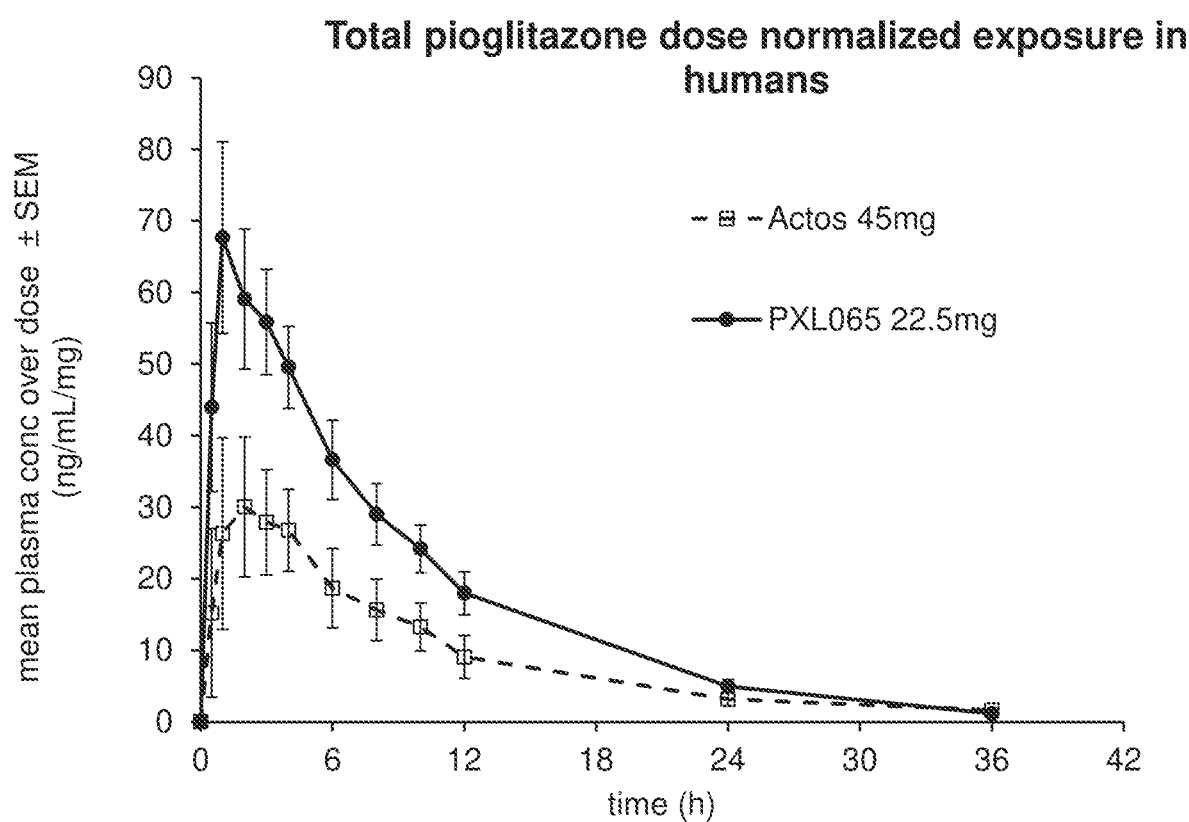
FIG. 21 is an overlay of total pioglitazone (sum of deuterated and protonated (R)- and (S)-enantiomers) dose normalized exposure curves for the crystalline hydrochloride salt of deuterium-enriched (R)-pioglitazone (22.5 mg dose) and Actos® (pioglitazone HCl, 45 mg dose) in humans, as further described in Example 11.

As shown in Table 21 and FIG. 21, PXL065 has improved bioavailability after single dose administration in healthy human subjects compared to Actos®.

TABLE 21

Total Pioglitazone Exposure in Phase Ia Study in Humans

| | AUCinf (h · ng/mL) | AUCinf dose normalized (h · ng/mL/mg) | Relative bioavailability (%) |
|---|---|---|---|
| Actos® 45 mg | 15981 | 355 | |
| PXL065 22.5 mg | 13896 | 618 | 174 |

$AUC_{inf}$ = area under the plasma concentration-time curve from time 0 to infinity; total pioglitazone (sum of deuterated and protonated (R)- and (S)-enantiomers of pioglitazone)

Example 12 A Phase Ib Study to Assess the Safety, Tolerability, and Pharmacokinetics of Repeated Doses of the Crystalline HCl Salt of Deuterium-Enriched (R)-Pioglitazone (PXL065) in Healthy Human Subjects Compared to Pioglitazone HCl (Actos®)

Objectives

The primary objective of this study was to assess the safety and tolerability in healthy subjects of repeated administrations of different doses of PXL065 compared to Pioglitazone HCl (Actos®) 45 mg.

A secondary objective of this study was to assess the PK of PXL065 in healthy subjects after single and multiple administrations compared to Actos®, 45 mg, with a specific focus on assessing the exposures to both deuterated and protonated (R)- and (S)-enantiomers of pioglitazone to determine the extent, if any, of interconversion of PXL065 to the protonated (R)- and (S)-enantiomers.

Study Methodology

Subjects were screened within 28 days before their first dose of study medication. They stayed in the clinic from 1 day before dosing (Day −1) until at least 48 hours after their final dose of trial medication (Day 11). Subjects returned to the clinic for outpatient assessments and/or PK sampling on Day 12 (approximately 72 hours postdose), Day 13 (approximately 96 hours postdose), Day 14 (approximately 120 hours postdose), Day 15 (approximately 144 hours post-dose), and for a follow up visit at 10 days (±2 days) after their final dose.

Up to 30 healthy subjects were enrolled in this trial:
Three (3) PXL065 dose groups: 8 subjects (6 on active and 2 on placebo) in each dose group. Each dose group was composed of 4 males and 4 females in a 3:1 active/placebo ratio.
One (1) Actos® group: 6 subjects (3 males and 3 females) were given Actos®. Placebo was not given to any subjects in this group.

The dose levels in Groups 1-4 were as follows (Table 22):

TABLE 22

Dose Levels in Groups 1-4

| Group | PXL065 | Actos® |
|---|---|---|
| 1 | — | 45 |
| 2 | 7.5 mg | — |
| 3 | 15 mg | — |
| 4 | 30 mg | — |

Subjects received a single oral dose of study drug (7.5, 15, or 30 mg tablets of PXL065 or matching placebo tablets, or 45 mg Actos® tablets), under fasting conditions on Day 1.

They then received repeated administrations of each study drug for 7 days from Day 3 to Day 9. All study drugs were dosed in fasting conditions.

The PXL065 PK parameters of the three single oral doses on Day 1 and after seven daily administrations on Day 9 were compared to the Actos® PK parameters on Day 1 and after seven daily administrations on Day 9.

Diagnosis and Criteria for Inclusion

Subjects were healthy adult male or female, 18-45 years of age (inclusive), with a body mass index (BMI) of ≥18.5 to ≤32 kg/m² and a body weight of ≥60 kg at screening. Female subjects were not pregnant or breastfeeding.

Test Product, Dose, and Mode of Administration

PXL065, orally administered. Dose=1×7.5 mg tablet, 1×15 mg tablet, or 1×30 mg tablet.

The PXL065 tablet include 7.5 mg, 15 mg, or 30 mg of PXL065, as well as lactose, carmellose calcium, hyprolose, and magnesium stearate.

Control Product, Dose, and Mode of Administration

Actos®, orally administered. Dose=1×45 mg tablet.

Actos® was purchased as the branded product. A 45 mg tablet includes 45 mg pioglitazone HCl salt, lactose, carmellose calcium, hyprolose, and magnesium stearate.

Duration of Treatment

One single oral administration of PXL065 or matching placebo or Actos® was given on Day 1 in fasting conditions followed by once daily multiple oral administrations of PXL065 or matching placebo or Actos® from Day 3 to Day 9 (7 days) in fasting conditions.

Criteria for Evaluation

Pharmacokinetics: Plasma samples were analyzed using a validated assay. The samples from all evaluable subjects were analyzed. Samples from subjects who experienced emesis within 4 hours of dosing were not analyzed.

Plasma PK parameters included, but were not limited to:
Following single dose on Day 1 and Day 3 (for PXL065 groups): $t_{max}$, $t_{lag}$, $C_{max}$, $AUC_{0-last}$, $AUC_{0-24}$, $AUC_{0-inf}$, $\lambda_z$, $t_{1/2}$, $\% AUC_{ext}$, CL/F, Vz/F, $C_{max}$/Dose, $AUC_{0-last}$/Dose, $AUC_{0-inf}$/Dose and MRT each calculated using compartmental or non-compartmental methods as appropriate for the deuterated and protonated (R)- and (S)-enantiomers of pioglitazone.

Day 4 to Day 9: $C_{trough}$ for the deuterated and protonated (R)- and (S)-enantiomers of pioglitazone; and Following repeated doses on Day 9: $t_{max}$, $C_{max}$, $C_{avg}$, $t_{lag}$, $AUC_{0-last}$, $AUC_{0-24}$, $AUC_{0-inf}$, $\lambda_z$, $t_{1/2}$, $\% AUC_{ext}$, $CL_{ss}/F$, $Vz_{ss}/F$, MRT, PTF, $R_{ac}(AUC_{0-24})$, $R_{ac}(C_{max})$ SR(AUC), $C_{max}$/Dose, $AUC_{0-last}$/Dose, $AUC_{0-inf}$/Dose, $AUC_{0-24}$/Dose.

Safety

The Investigator evaluated safety using the following assessments: physical examinations, vital sign measurements, clinical laboratory evaluations, electrocardiograms, and reported or observed adverse events (AEs). Subjects were monitored for any AEs from the signing of the informed consent through the end of the study.

Statistical Methods

In general, all data was summarized with descriptive statistics (number of subjects, means, standard deviations, minimums, medians, and maximums) for continuous endpoints, and frequency and percentage for categorical endpoints. Within each part of the clinical study, data was presented separately for each cohort and by treatment group within each cohort.

Safety and tolerability: all safety and tolerability data were listed. In the case of continuous variables, descriptive statistics was used to summarize the results and changes from baseline by treatment and time point. The values of categorical assessments were tabulated. Adverse Events (AEs) were coded according to MedDRA.

Results

Pharmacokinetic results: the relative bioavailability in humans of PXL065 increased by 55%-65% compared to Actos® (see Table 23 and FIG. 18).

TABLE 23

Pharmacokinetic Parameters for PXL065 and Actos® in Humans

| Total Pioglitazone Exposure in Humans | $AUC_{0-24}$,ss (h*ng/mL) | $AUC_{0-24}$,ss dose normalized (h*ng/mL/mg) | Relative Bioavailability (%) |
|---|---|---|---|
| Actos ® 45 mg | 12567 | 279 | — |
| PXL065 15 mg | 6505 | 434 | 155 |
| PXL065 30 mg | 13802 | 460 | 165 |

Figure 22:
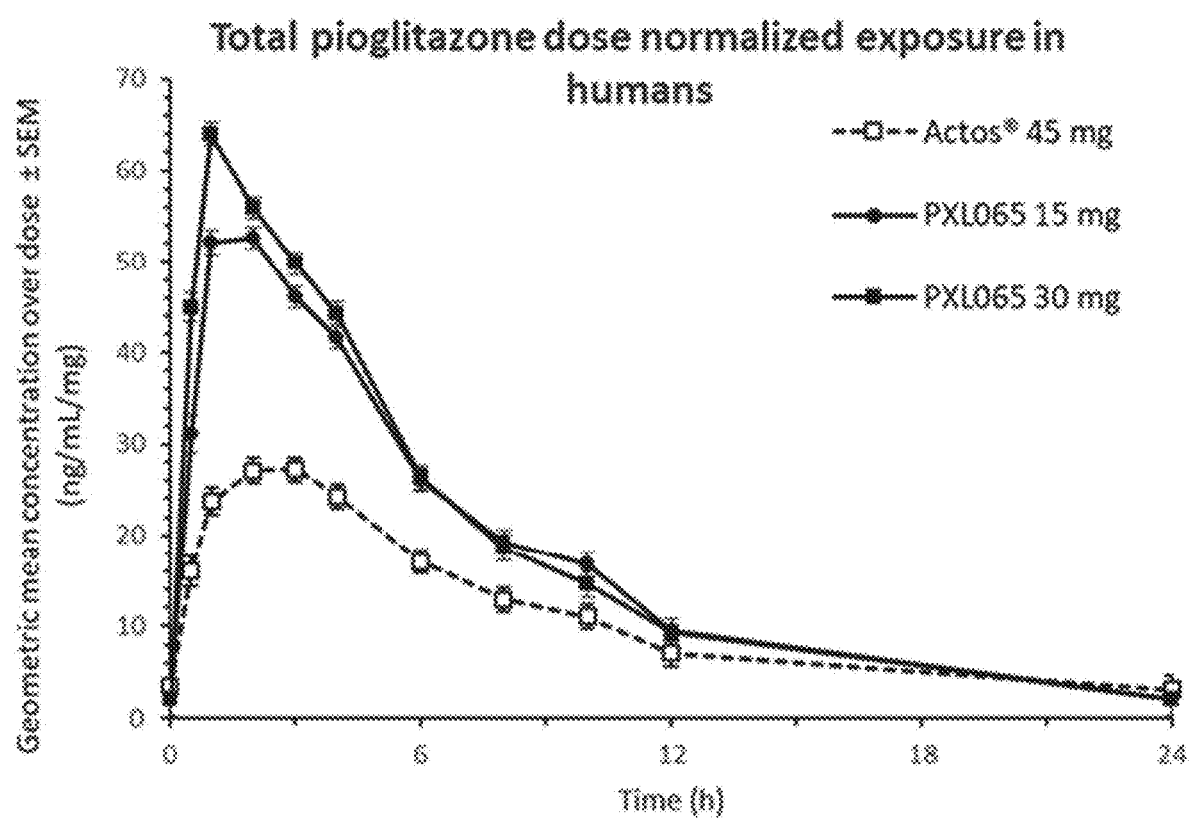
FIG. 22 is an overlay of total pioglitazone (sum of deuterated and protonated (R)- and (S)-enantiomers) dose normalized exposure curves for the crystalline hydrochloride salt of deuterium-enriched (R)-pioglitazone (15 mg and 30 mg doses) and Actos® (pioglitazone HCl, 45 mg dose) in humans, as further described in Example 12.

As shown in Table 23 and FIG. 22, PXL065 has improved bioavailability after repeated dose administrations in healthy human subjects compared to Actos®.

Combined, the results from the two dog and two human PK studies described above in Examples 9-12 show that bioavailability to total pioglitazone (sum of protonated and deuterated (R)- and (S)-enantiomers) with PXL065 compared to pioglitazone is independent of the formulation (capsule or tablet).

INCORPORATION BY REFERENCE

This application refers to various issued patents, published patent applications, journal articles, and other publications, all of which are incorporated herein by reference. If there is a conflict between any of the incorporated references and the instant specification, the specification shall control. In addition, any particular embodiment of the present disclosure that falls within the prior art may be explicitly excluded from any one or more of the claims. Because such embodiments are deemed to be known to one of ordinary skill in the art, they may be excluded even if the exclusion is not set forth explicitly herein. Any particular embodiment of the disclosure can be excluded from any claim, for any reason, whether or not related to the existence of prior art.

EQUIVALENTS

The invention may be embodied in other specific forms without departing from the spirit or essential characteristics thereof. The foregoing embodiments are therefore to be considered in all respects illustrative rather than limiting the invention described herein. Scope of the invention is thus indicated by the appended claims rather than by the foregoing description, and all changes that come within the meaning and range of equivalency of the claims are intended to be embraced therein.

We claim:

1. A crystalline hydrochloride salt of a compound of formula (I-A):

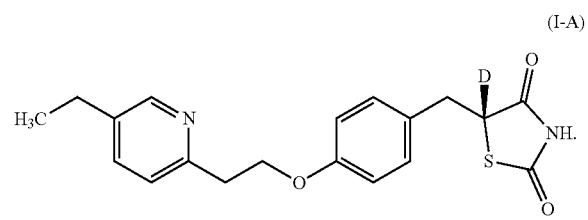 [SMILES: [2H][C@]1(Cc2ccc(OCCc3ccc(CC)cn3)cc2)SC(=O)NC1=O]

(I-A)

wherein the crystalline hydrochloride salt is characterized by an X-ray powder diffraction pattern comprising peaks at the following diffraction angles (2θ): 15.8°±0.2°, 22.8°±0.2°, and 26.0°±0.2°.

2. The crystalline hydrochloride salt of claim 1, wherein the crystalline hydrochloride salt is characterized by an X-ray powder diffraction pattern comprising peaks at the following diffraction angles (2θ): 15.8°±0.2°, 20.0°±0.2°, 20.8°±0.2°, 22.8°±0.2°, and 26.0°±0.2°.

3. The crystalline hydrochloride salt of claim 1, wherein the crystalline hydrochloride salt is characterized by an X-ray powder diffraction pattern comprising peaks at the following diffraction angles (2θ): 8.6°±0.2° 8.8°±0.2°, 12.8°±0.2°, 12.9°±0.2° 15.8°±0.2°, 18.8°±0.2°, 19.7°±0.2°, 20.0°±0.2°, 20.8°±0.2°, 22.8°±0.2°, 26.0°±0.2°, 28.1°±0.2°, and 31.3°±0.2°.

4. The crystalline hydrochloride salt of claim 1, wherein the crystalline hydrochloride salt is characterized by an X-ray powder diffraction pattern substantially the same as shown in FIG. 6.

5. The crystalline hydrochloride salt of claim 1, wherein the crystalline hydrochloride salt has a melting point onset as determined by differential scanning calorimetry at about 190° C. to about 210° C.

6. The crystalline hydrochloride salt of claim 1, wherein the crystalline hydrochloride salt is an anhydrous crystalline hydrochloride salt.

7. A pharmaceutical composition comprising a crystalline hydrochloride salt of claim 1, and a pharmaceutically acceptable excipient.

8. A method of treating a metabolic disorder in a patient in need thereof, the method comprising administering to the patient an effective amount of a crystalline hydrochloride salt of claim 1.

9. The method of claim 8, wherein the metabolic disorder is polycystic ovary syndrome.

10. A method of treating diabetes mellitus type 2 in a patient in need thereof, the method comprising administering to the patient an effective amount of a crystalline hydrochloride salt of claim 1.

11. A method of treating nonalcoholic steatohepatitis in a patient in need thereof, the method comprising administering to the patient an effective amount of a crystalline hydrochloride salt of claim 1.

12. A method of treating nonalcoholic fatty liver disease in a patient in need thereof, the method comprising administering to the patient an effective amount of a crystalline hydrochloride salt of claim 1.

13. A method of treating a neurological disorder in a patient in need thereof, the method comprising administering to the patient an effective amount of a crystalline hydrochloride salt of claim 1.

14. The method of claim 13, wherein the neurological disorder is adrenoleukodystrophy or adrenomyeloneuropathy.

* * * * *